United States Patent
Langhals et al.

(10) Patent No.: US 8,404,705 B2
(45) Date of Patent: Mar. 26, 2013

(54) NAPHTHALENE AMIDINE IMIDES

(75) Inventors: Heinz Langhals, Ottobrunn (DE);
Harald Jaschke, Jetzendorf (DE);
Thomas Ehlis, Freiburg (DE); Olof Wallquist, Bottmingen (CH)

(73) Assignee: BASF SE, Ludwigshafen (DE)

( * ) Notice: Subject to any disclaimer, the term of this patent is extended or adjusted under 35 U.S.C. 154(b) by 741 days.

(21) Appl. No.: 11/989,163

(22) PCT Filed: Jul. 21, 2006

(86) PCT No.: PCT/EP2006/064531
§ 371 (c)(1),
(2), (4) Date: Mar. 25, 2010

(87) PCT Pub. No.: WO2007/012611
PCT Pub. Date: Feb. 1, 2007

(65) Prior Publication Data
US 2010/0202984 A1     Aug. 12, 2010

(30) Foreign Application Priority Data
Jul. 25, 2005   (DE) .................. 10 2005 034 685

(51) Int. Cl.
*A61K 31/439* (2006.01)
*C07D 471/08* (2006.01)

(52) U.S. Cl. .......................... 514/288; 546/66

(58) Field of Classification Search .............. 514/288; 546/66
See application file for complete search history.

(56) References Cited

U.S. PATENT DOCUMENTS

| | | | |
|---|---|---|---|
| 1,920,406 A | 8/1933 | Kränzlein et al. | 260/124 |
| 5,886,183 A | 3/1999 | Langhals et al. | 546/62 |
| 2003/0153005 A1 | 8/2003 | Schmid et al. | 435/7.1 |
| 2004/0116493 A1* | 6/2004 | Sugimori et al. | 514/389 |

FOREIGN PATENT DOCUMENTS

| | | |
|---|---|---|
| DE | 456236 | 2/1928 |
| DE | 19613671 | 10/1996 |
| JP | 2000-214614 A * | 8/2000 |

OTHER PUBLICATIONS

English language abstract of DE 19613671, Oct. 1996.
Patent Abstracts of Japan Publication No. 2004093791, Mar. 2004.
G. P. Wiederrecht et al., Journal of the American Chemical Society, vol. 118, (1996), pp. 81-88.
Dane G. Hamilton et al., Journal of the Chemical Society Perkin Transactions 1, (1999), pp. 1057-1065.
Howard E. Katz, Journal of the Americal Chemical Society, vol. 122, (2000), pp. 7787-7792.
J. Arient et al, Collection Czechoslov. Chem. Commun., vol. 30, (1965), pp. 3718-3729.
Peter J. Stang et al., Journal of the American Chemical Society, vol. 117, (1995), pp. 6273-6283.
H. E. Fierz-David et al., Helvetica Chimica Acta., vol. 21, (1938), pp. 1466-1489.
Heinz Langhals et al., Chemistry A European Journal, vol. 12, (2006), pp. 2815-2824.

* cited by examiner

*Primary Examiner* — Charanjit Aulakh
(74) *Attorney, Agent, or Firm* — Shiela A. Loggins

(57) ABSTRACT

Disclosed are naphthalinamidinimide of formula

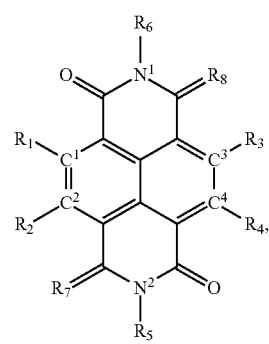

(1)

wherein the substituents $R_1$-$R_8$ are defined herein.

4 Claims, No Drawings

NAPHTHALENE AMIDINE IMIDES

The present invention relates to the compounds of formula

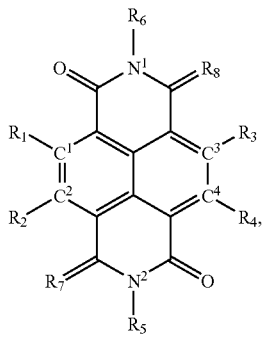

(1)

wherein $R_1$, $R_2$, $R_3$, $R_4$, $R_5$ and $R_6$ independently from each other are hydrogen; or $C_1$-$C_{37}$alkyl; wherein one to 10 of the $CH_2$ units of $C_1$-$C_{37}$alkyl independently from each may be substituted by carbonyl groups; oxygen atoms; sulphur atoms; selenium atoms; tellurium atoms; cis- or trans-CH=CH— groups; acetylenic C≡C— groups; 1,2-, 1,3- or 1,4-substituted phenyl radicals; 2,3-, 2,4-, 2,5-, 2,6-, 3,4- or 3,5-disubstituted pyridine radicals; 2,3-, 2,4-, 2,5- or 3,4-disubstituted thiophene radicals; 1,2-, 1,3-, 1,4-, 1,5-, 1,6-, 1,7-, 1,8-, 2,3-, 2,6- or 2,7-disubstituted 1,2-, 1,3-, 1,4-, 1,5-, 1,6-, 1,7-, 1,8-, 1,9-, 1,10-, 2,3-, 2,6-, 2,7-, 2,9-, 2,10- or 9,10-disubstituted anthracene radicals; wherein one or 2 CH— groups of the CH=CH— groups, the naphthalene radicals and the anthracene radicals may be substituted by nitrogen atoms;

up to 12 single hydrogen atoms of the $CH_2$— groups independently from each other may be substituted at the same carbon atoms by fluorine; chlorine; bromine; or iodine; the cyano group; a linear alkyl chain with up to 18 carbon atoms; cis- or trans-CH=CH— groups; acetylenic C≡C— groups; 1,2-, 1,3- or 1,4-substituted phenyl radicals; 2,3-, 2,4-, 2,5-, 2,6-, 3,4- or 3,5-disubstituted pyridine radicals; 2,3-, 2,4-, 2,5- or 3,4-disubstituted thiophene radicals; 1,2-, 1,3-, 1,4-, 1,5-, 1,6-, 1,7-, 1,8-, 2,3-, 2,6- or 2,7-disubstituted naphthalene radicals; 1,2-, 1,3-, 1,4-, 1,5-, 1,6-, 1,7-, 1,8-, 1,9-, 1,10-, 2,3-, 2,6-, 2,7-, 2,9-, 2,10- or 9,10-disubstituted anthracene radicals; wherein up to 6 $CH_2$-units in the alkyl chain independently from each other may be substituted by carbonyl groups, oxygen atoms, sulphur atoms, selenium atoms, tellurium atoms and up to 12 single hydrogen atoms of the $CH_2$— groups of the alkyl radicals each independently from each other may also be substituted at the same C-atoms by fluorine, chlorine, bromine or iodine or cyano groups or linear alkyl chains with up to 18 carbon atoms, wherein one to 6 $CH_2$-units independently from each other may be substituted by carbonyl groups, oxygen atoms, sulphur atoms, selenium atoms, tellurium atoms, cis- or trans-CH=CH— groups, wherein one CH-unit may also be substituted by a nitrogen atom, by acetylenic C≡C— groups, 1,2-, 1,3- or 1,4-substituted phenyl radicals, 2,3-, 2,4-, 2,5-, 2,6-, 3,4- or 3,5-disubstituted pyridine radicals, 2,3-, 2,4-, 2,5- or 3,4-disubstituted thiophene radicals, 1,2-, 1,3-, 1,4-, 1,5-, 1,6-, 1,7-, 1,8-, 2,3-, 2,6- or 2,7-disubstituierte naphthalene radicals, wherein one or two carbon atoms may be substituted by nitrogen atoms, by 1,2-, 1,3-, 1,4-, 1,5-, 1,6-, 1,7-, 1,8-, 1,9-, 1,10-, 2,3-, 2,6-, 2,7-, 2,9-, 2,10- or 9,10-di-substituierte anthracene radicals, wherein one or two carbon atoms may be substituted by nitrogen atoms; or instead of substituents the free valencies of the methine- or quarternary carbon atoms may be linked pairwise forming rings like cyclohexane rings; or are an amino radical, if $R_1$ and $R_2$ together with the carbon atoms $C^1$ and $C^2$ or $R_3$ and $R_4$ together with the carbon atoms $C^3$ and $C^4$ form a 6-membered radical;

$R_7$ and $R_8$, independently from each other are =O; or =NH—, if =NH— together with the nitrogen atom $N^1$ (for $R_6$) or together with the nitrogen atom $N^2$ (for $R_7$) forms a five-membered radical.

Alkyl ist for example methyl, ethyl, n-propyl, isopropyl, n-butyl, sec-butyl, isobutyl, tert.-butyl, n-pentyl, 2-pentyl, 3-pentyl, 2,2-dimethylpropyl, n-hexyl, n-octyl, 1,1,3,3-tetramethylbutyl, 2-ethylhexyl, nonyl, decyl, n-octadecyl, eicosyl or dodecyl.

Examples for branched alkyl are 1-methylpropyl; 1,3-dimethylbutyl; 2-methylbutyl; 1,1,3,3-tetramethylbutyl; 3-methylbutyl; 7-methyloctyl; 2-ethylhexyl; or 4-methylcyclohexyl.

Cycloalkyl is for example, cyclopentyl, trimethylcyclohexyl, cyclooctyl or preferably cyclohexyl.

Preferred are compounds of formula

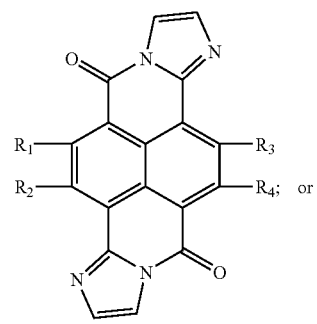

(2)

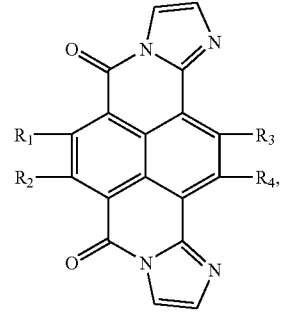

(3)

worin $R_1$, $R_2$, $R_3$ and $R_4$ are defined as in formula (1).

More preferred are also compounds of formula

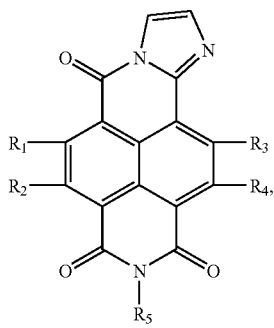

(4)

wherein
R$_1$, R$_2$, R$_3$, R$_4$ and R$_5$ are defined as in formula (1).

More preferred are naphthalene amidines of formula

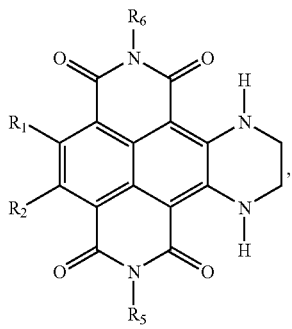

(5)

wherein
R$_1$, R$_2$, R$_5$ and R$_6$ are defined as in claim 1.

Also preferred are naphthalene amidines of formula

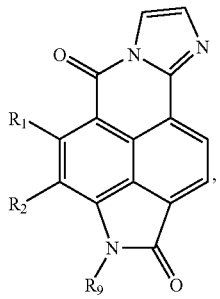

(6)

wherein
R$_1$, R$_2$ and R$_9$ independently from each other are hydrogen; or C$_1$-C$_{37}$alkyl; wherein
1 to 10 der CH$_2$-units of C$_1$-C$_{37}$alkyl may be replaced by carbonyl groups; —O—; —S—; —Se—; —Te—; cis- or trans-CH═CH— groups; acetylenic C≡C— groups; 1,2-, 1,3- or 1,4-substituted phenyl radicals; 2,3-, 2,4-, 2,5-, 2,6-, 3,4- or 3,5-disubstituted Pyridine radicals; 2,3-, 2,4-, 2,5- or 3,4-disubstituted Thiophene radicals; 1,2-, 1,3-, 1,4-, 1,5-, 1,6-, 1,7-, 1,8-, 2,3-, 2,6- or 2,7-disubstituted, 1,2-, 1,3-, 1,4-, 1,5-, 1,6-, 1,7-, 1,8-, 1,9-, 1,10-, 2,3-, 2,6-, 2,7-, 2,9-, 2,10- or 9,10-disubstituted anthracene radicals; wherein one or 2 CH— groups of the CH═CH— groups of the Naphthalene radicals and the anthracene radicals may be replaced by nitrogen atoms;
up to 12 single hydrogen atoms of the CH$_2$— groups independently from each other may be substituted at the same carbon atoms by fluorine; chlorine; bromine; or iodine; the cyano group; a linear alkyl chain with up to 18 carbon atoms; cis- or trans-CH═CH— groups; acetylenic C≡C— groups; 1,2-, 1,3- or 1,4-substituted phenyl radicals; 2,3-, 2,4-, 2,5-, 2,6-, 3,4- or 3,5-disubstituted pyridine radicals; 2,3-, 2,4-, 2,5- or 3,4-disubstituted thiophene radicals; 1,2-, 1,3-, 1,4-, 1,5-, 1,6-, 1,7-, 1,8-, 2,3-, 2,6- or 2,7-disubstituted naphthalene radicals; 1,2-, 1,3-, 1,4-, 1,5-, 1,6-, 1,7-, 1,8-, 1,9-, 1,10-, 2,3-, 2,6-, 2,7-, 2,9-, 2,10- or 9,10-disubstituted anthracene radicals; wherein up to 6 CH$_2$-units in the alkyl chain independently from each other may be substituted by carbonyl groups, oxygen atoms, sulphur atoms, selenium atoms, tellurium atoms and up to 12 single hydrogen atoms of the CH$_2$— groups of the alkyl radicals each independently from each other may also be substituted at the same C-atoms by fluorine, chlorine, bromine or iodine or cyano groups or linear alkyl chains with up to 18 carbon atoms, wherein one to 6 CH$_2$-units independently from each other may be substituted by carbonyl groups, oxygen atoms, sulphur atoms, selenium atoms, tellurium atoms, cis- or trans-CH═CH— groups, wherein one CH-unit may also be substituted by a nitrogen atom, by acetylenic C≡C— groups, 1,2-, 1,3- or 1,4-substituted phenyl radicals, 2,3-, 2,4-, 2,5-, 2,6-, 3,4- or 3,5-disubstituted pyridine radicals, 2,3-, 2,4-, 2,5- or 3,4-disubstituted thiophene radicals, 1,2-, 1,3-, 1,4-, 1,5-, 1,6-, 1,7-, 1,8-, 2,3-, 2,6- or 2,7-disubstituierte naphthalene radicals, wherein one or two carbon atoms may be substituted by nitrogen atoms, by 1,2-, 1,3-, 1,4-, 1,5-, 1,6-, 1,7-, 1,8-, 1,9-, 1,10-, 2,3-, 2,6-, 2,7-, 2,9-, 2,10- or 9,10-disubstituierte anthracene radicals, wherein one or two carbon atoms may be substituted by nitrogen atoms; or
instead of substituents the free valencies of the methine- or quarternary carbon atoms may be linked pairwise forming rings like cyclohexane rings.

Mostly preferred are naphthalene amidines which correspond to the formula

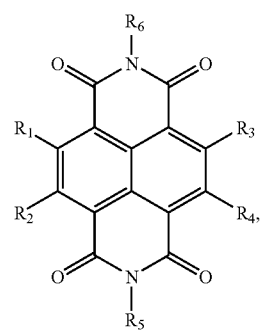

(7)

wherein
R$_1$, R$_2$, R$_3$, R$_4$, R$_5$ and R$_6$ independently from each other are hydrogen; or C$_1$-C$_{12}$alkyl; and even more preferred are naphthalene which correspond to the formulae

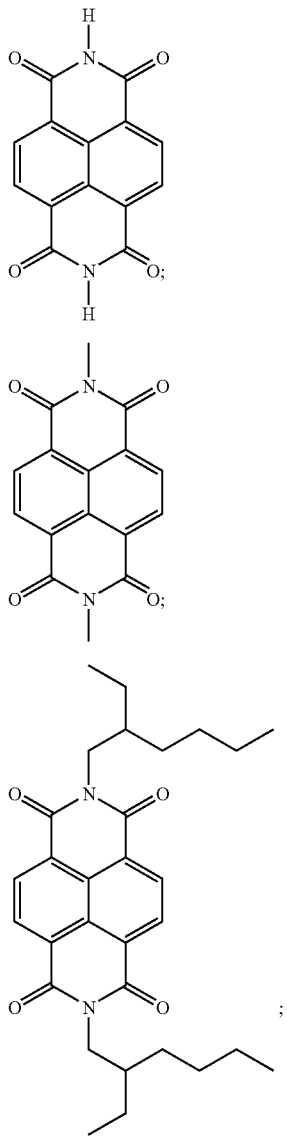

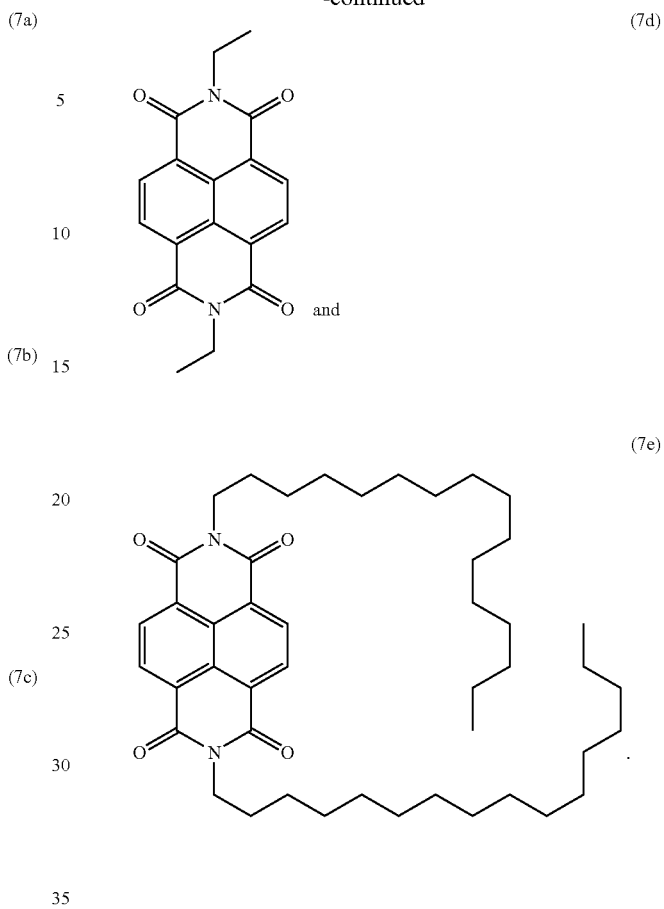

The compounds of formulae (7a), (7b) and (7d) are sparingly soluble compounds and are therefore suitable as micronized UV filters.

By introduction of longer alkyl chains UV absorbers are obtained which are soluble in cosmetic oils. Example of these compounds are (7c) and (7e).

Further examples of naphthalene amidinimides according to the present invention are listed below:

| | |
|---|---|
| NA-01 | 2,7-Bis-(1-methylpropyl)benzo[lmn][3,8]phenanthrolin-1,3,6,8-tetron |
| NA-02 | 2,7-Bis-(2-methyl-2-propylpentyl)benzo[lmn][3,8]phenanthrolin-1,3,6,8-tetron |
| NA-03 | 2,7-Bis-(2,2-dimethylheptyl)benzo[lmn][3,8]phenanthrolin-1,3,6,8-tetron |
| NA-04 | 2,7-Bis-(2,2-dihexyloctyl)benzo[lmn][3,8]phenanthrolin-1,3,6,8-tetron |
| NA-05 | 2,7-Bis-(1-ethylcyclohexylmethyl)benzo[lmn][3,8]phenanthrolin-1,3,6,8-tetron |
| NA-06 | 2,7-Bis-(1-proplcyclohexylmethyl)benzo[lmn][3,8]phenanthrolin-1,3,6,8-tetron |
| NA-07 | 2,7-Bis-(2-ethyl-2-phenylbutyl)benzo[lmn][3,8]phenanthrolin-1,3,6,8-tetron |
| NA-08 | 2,7-Bis-(2-butyl-2-phenylhexyl)benzo[lmn][3,8]phenanthrolin-1,3,6,8-tetron |
| NA-09 | 2,7-Bis-(2,3-dimethylphenyl)benzo[lmn][3,8]phenanthrolin-1,3,6,8-tetron |
| NA-10 | 2,7-Bis-(2,5-dimethylphenyl)benzo[lmn][3,8]phenanthrolin-1,3,6,8-tetron |
| NA-11 | 2,7-Bis-(5-tert-butyl-2-methyl)benzo[lmn][3,8]phenanthrolin-1,3,6,8-tetron |
| NA-12 | 2,7-Bis-(2-tert-butylphenyl)benzo[lmn][3,8]phenathrolin-1,3,6,8-tetron |
| NA-13 | 2,7-Bis-(4-tert-butylphenyl)benzo[lmn][3,8]phenanthrolin-1,3,6,8-tetron |
| NA-14 | 2,7-Bis-(2,5-di-tert-butylphenyl)-benzo[lmn][3,8]phenanthrolin-1,3,6,8-tetron |
| NA-15 | 2-(1-Methylpropyl)-benzo[lmn]imidazolo[1,2-j][3,8]phenanthrolin-1,3,6-trion |
| NA-16 | 2-(1-Methylbutyl)-benzo[lmn]imidazolo[1,2-j][3,8]phenanthrolin-1,3,6-trion |
| NA-17 | 2-(1-Hexylpentyl)-benzo[lmn]imidazolo[1,2-j][3,8]phenanthrolin-1,3,6-trion |
| NA-18 | 2-Cyclohexylbenzo[lmn]imidazolo[1,2-j][3,8]phenanthrolin-1,3,6-trion |
| NA-19 | 2-(2-Hydroxyethyl)benzo[lmn]imidazolo[1,2-j][3,8]phenanthrolin-1,3,6-trion |
| NA-20 | 2-(2-Hydroxypropyl)benzo[lmn]imidazolo[1,2-j][3,8]phenanthrolin-1,3,6-trion |
| NA-21 | 2-(4-tert-Butylphenyl)benzo[lmn]imidazolo[1,2-j][3,8]phenanthrolin-1,3,6-trion |
| NA-22 | N,N'-Di-(4-tert-butylphenyl)piperazino[2,3-l]naphthalin-1,8:4,5-bis-(dicarboximid) |

-continued

| | |
|---|---|
| NA-23 | 2-(2,5-Di-tert-butylphenyl)benzo[lmn]imidazolo[1,2-j][3,8]phenanthrolin-1,3,6-trion |
| NA-24 | N,N'-Di-(2,5-di-tert-butylphenyl)piperazino[2,3-l]naphthalin-1,8:4,5-bis-(dicarboximid) |
| NA-25 | 2-(2,5-Dimethylphenyl)benzo[lmn]imidazolo[1,2-j][3,8]phenanthrolin-1,3,6-trion |
| NA-26 | N,N'-Di-(2,5-dimethylphenyl)piperazino[2,3-l]naphthalin-1,8:4,5-bis-(dicarboximid) |
| NA-27 | N,N'-Di-(1-methylpropyl)piperazino[2,3-l]naphthalin-1,8:4,5-bis-(dicarboximid) |

The preparation of the compounds of formula (1) may be carried out according to known methods of the prior art as described in Chem. Eur. J. 2006, 2815-2824.

Naphthalene-1,8:4,5-tetracarboxylic bisimides of the general formula (1a) are preparatively easily accessible from the bisanhydride of formula (1b) according to the following reaction scheme and are formally the lower analogues of the well-known perylene dyes.

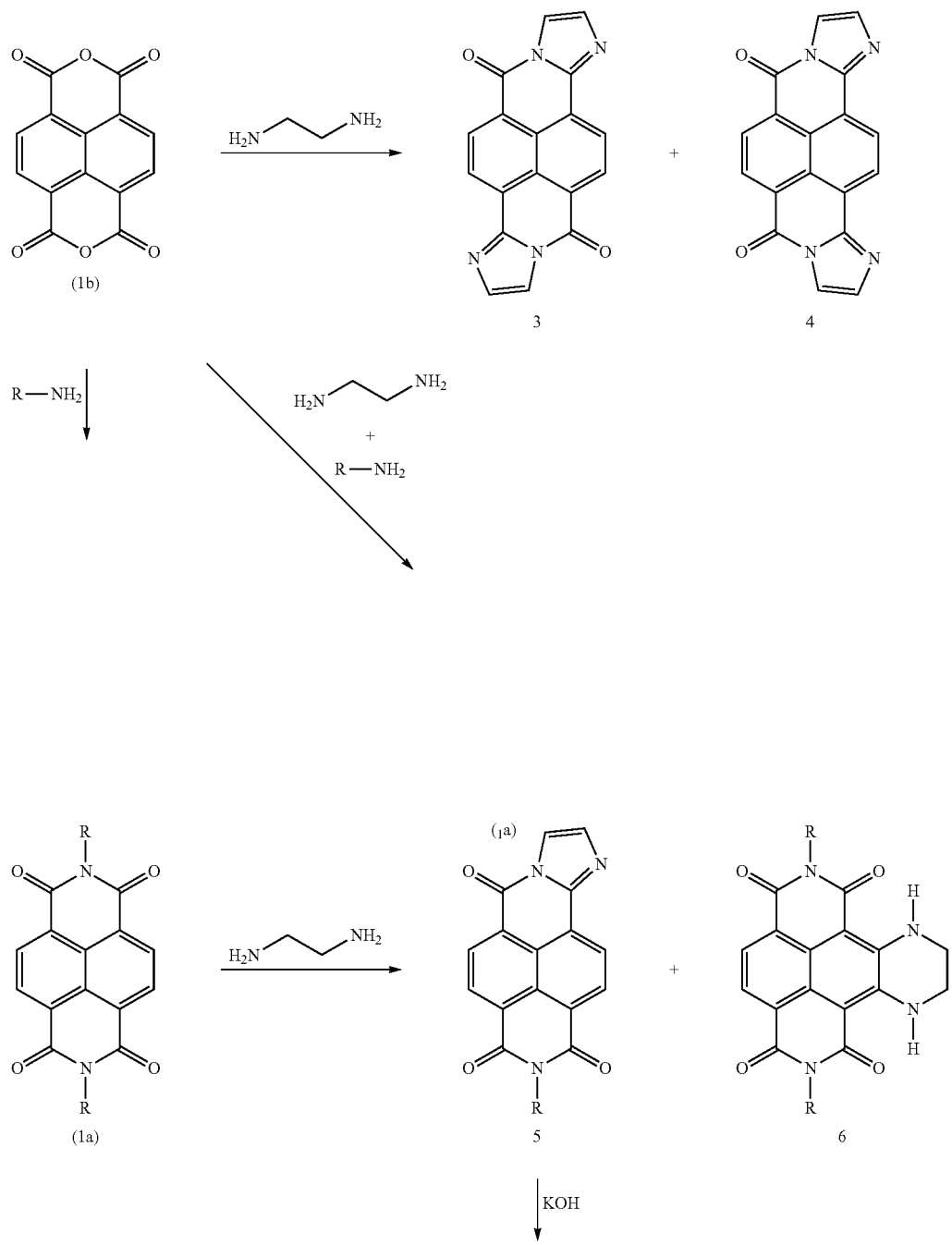

-continued

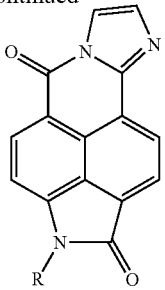

7

The compounds of the formula (1) according to the present invention are particularly suitable as UV filters, i.e. for protecting ultraviolet-sensitive organic materials, in particular the skin and hair of humans and animals, from the harmful effects of UV radiation. These compounds are therefore suitable as sunscreens in cosmetic, pharmaceutical and veterinary medical preparations. These compounds can be used either in the dissolved state (soluble organic filters, solubilised organic filters) or in the micronised state (nanoscalar organic filters, particulate organic filters, UV-absorber pigments).

Any known process suitable for the preparation of micropartides can be used for the preparation of the micronised UV absorbers, for example:

wet-milling (low viscous micronisation process for pumpable dispersions), with a hard grinding medium, for example zirconium silicate balls in a ball mill and a protective surfactant or a protective polymer in water or in a suitable organic solvent;

wet-kneading (high viscous micronisation process non pump-able pastes) using a continuous or discontinuous (batch) kneader. For a wet-kneading process a solvent (water or cosmetically acceptable oils), a grinding-aid (surfactant, emulsifier) and a polymeric grinding aid may be used.

Both processes may be used respectively spray-drying from a suitable solvent, for example aqueous suspensions or suspensions containing organic solvents, or true solutions in water, ethanol, dichloroethane, toluene or N-methylpyrrolidone etc.

by the expansion according to the RESS process (Rapid Expansion of Supercritical Solutions) of supercritical fluids (e.g. $CO_2$) in which the UV filter or filters is/are dissolved, or the expansion of fluid carbon dioxide together with a solution of one or more UV filters in a suitable organic solvent;

by reprecipitation from suitable solvents, including supercritical fluids (GASR process=Gas Anti-Solvent Recrystallisation/PCA process=Precipitation with Compressed Anti-solvents).

As milling apparatus for the preparation of the micronised organic UV absorbers there may be used, for example, a jet mill, ball mill, vibratory mill or hammer mill, preferably a high-speed mixing mill. Even more preferably used are modern ball mills; manufactures of these mill-types are for example Netzsch (LMZ-mill), Drais (DCP-viscoflow or cosmo), Bühler AG (centrifugal mills) or Bachhofer. The grinding is preferably carried out with a grinding aid. As kneading apparatus for the preparation of the micronised organic UV absorbers examples are typically sigma-hook batch kneaders but also serial batch kneaders (IKA-Werke) or continuous kneaders (Contiuna from Werner and Pfleiderer).

Useful low molecular weight grinding aids for all the above micronizing processes are surfactants and emulsifies as disclosed below in the chapters "emulsifiers" and "surfactants" and "fatty alcohols".

Useful polymeric grinding aids for water dispersion are cosmetically acceptable water soluble polymers with Mn>500 g/mol for example acrylates (Salcare types), modified or non-modified polysaccharides, polyglucosides or xanthan gum. Furthermore an alkylated vinylpyrrolidone polymer, a vinylpyrrolidone/vinyl acetate copolymer, an acyl glutamate, an alkyl polyglucoside, ceteareth-25 or a phospholipid may be used. Oil dispersions may contain cosmetically acceptable waxy polymers or natural waxes as polymeric grinding aid in order to adjust viscosity during and after processing. Examples of other useful polymeric grinding aids are disclosed below in the chapter "polymers".

Useful solvents for the grinding process are water, brine, (poly-)ethylenglycol, glycerine or cosmetically acceptable oils. Other useful solvents are disclosed below in the chapters "esters of fatty acids", "natural and synthetic triglycerides including glyceryl esters and derivatives", "pearlescent waxes", "hydrocarbon oils" and "silicones or siloxanes".

The micronised UV absorbers so obtained usually have an average particle size from 0.02 to 2, preferably from 0.03 to 1.5, and more especially from 0.05 to 1.0 micrometer.

The UV absorbers according to the present invention can also be used as dry substrates in powder form. For that purpose the UV absorbers are subjected to known grinding methods, such as vacuum atomization, countercurrent spray-drying etc. Such powders have a particle size from 0.1 micrometer to 2 micrometer. In order to avoid the occurrence of agglomeration, the UV absorbers may be coated with a surface-active compound prior to the pulverization process, for example with an anionic, non-ionic or amphoteric surfactant, e.g. a phospholipid or a known polymer, such as PVP, an acrylate etc.

The UV absorbers according to the present invention can also be used in specific carriers for cosmetics, for example in solid lipid nanoparticles (SLN) or in inert sol-gel microcapsules wherein the UV absorbers are encapsulated (Pharmazie, 2001 (56), p. 783-786).

Lipid nanoparticles (CLN, =Crystalline Lipid Nanoparticles) as described in Internat. J. Pharmaceutics, 2002, 242, P. 373-375 can be used as active carrier for UV filter according to the invention (for example the compound of formula 6).

The cosmetic formulations or pharmaceutical compositions according to the present invention may additionally contain one or more than one further UV filter as listed in tables 1-3.

The cosmetic or pharmaceutical preparations can be prepared by physically mixing the UV absorber(s) with the adjuvant using customary methods, for example by simply stirring together the individual components, especially by making use of the dissolution properties of already known cosmetic UV absorbers, like octyl methoxy cinnamate, salicylic acid isooctyl ester, etc. The UV absorber can be used, for example, without further treatment, or in the micronised state, or in the form of a powder.

Cosmetic or pharmaceutical preparations contain from 0.05-40% by weight, based on the total weight of the composition, of one UV absorber or UV absorber mixtures.

Preference is given to the use of mixing ratios of the UV absorber of formula (1) according to the present invention and optionally further light-protective agents (as described in table 1-3) from 1:99 to 99:1, preferably from 1:95 to 95:1 and most preferably from 10:90 to 90:10, based on weight. Of special interest are mixing ratios of from 20:80 to 80:20, preferably from 40:60 to 60:40 and most preferably approximately 50:50. Such mixtures can be used, inter alia, to improve the solubility or to increase UV absorption.

The UV absorbers of formula (1) according to the present invention or combinations of UV filters are useful to protect skin, hair and/or natural or artificial hair color.

TABLE 1

Suitable UV filter substances which can be additionally used with the UV absorbers according to the present invention p-aminobenzoic acid derivatives, for example 4-dimethylaminobenzoic acid 2-ethylhexyl ester;
salicylic acid derivatives, for example salicylic acid 2-ethylhexyl ester;
benzophenone derivatives, for example 2-hydroxy-4-methoxybenzophenone and its 5-sulfonic acid derivative;
dibenzoylmethane derivatives, for example 1-(4-tert-butylphenyl)-3-(4-methoxyphenyl)-propane-1,3-dione;
diphenylacrylates, for example 2-ethylhexyl 2-cyano-3,3-diphenylacrylate, and 3-(benzofuranyl) 2-cyanoacrylate;
3-imidazol-4-ylacrylic acid and esters;
benzofuran derivatives, especially 2-(p-aminophenyl)benzofuran derivatives, described in EP-A-582 189, U.S. Pat. No. 5,338,539, U.S. Pat. No. 5,518,713 and EP-A-613 893;
polymeric UV absorbers, for example the benzylidene malonate derivatives described in EP-A-709 080;
cinnamic acid derivatives, for example the 4-methoxycinnamic acid 2-ethylhexyl ester and isoamyl ester or cinnamic acid derivatives described in U.S. Pat. No. 5,601,811 and WO 97/00851;
camphor derivatives, for example 3-(4'-methyl)benzylidene-bornan-2-one, 3-benzylidene-bornan-2-one, N-[2(and 4)-2-oxyborn-3-ylidene-methyl)-benzyl]acrylamide polymer, 3-(4'-trimethylammonium)-benzylidene-bornan-2-one methyl sulfate, 3,3'-(1,4-phenylenedimethine)-bis(7,7-dimethyl-2-oxo-bicyclo[2.2.1]heptane-1-methanesulfonic acid) and salts, 3-(4'-sulfo)benzylidene-bornan-2-one and salts; camphorbenzalkonium methosulfate;
hydroxyphenyltriazine compounds, for example 2-(4'-methoxyphenyl)-4,6-bis(2'-hydroxy-4'-n-octyloxyphenyl)-1,3,5-triazine; 2,4-bis{[4-(3-(2-propyloxy)-2-hydroxy-propyloxy)-2-hydroxy]-phenyl}-6-(4-methoxyphenyl)-1,3,5-triazine; 2,4-bis{[4-(2-ethyl-hexyloxy)-2-hydroxy]-phenyl}-6-[4-(2-methoxyethyl-carboxyl)-phenylamino]-1,3,5-triazine; 2,4-bis{[4-(tris(trimethylsilyloxy-silylpropyloxy)-2-hydroxy]-phenyl}-6-(4-methoxyphenyl)-1,3,5-triazine; 2,4-bis{[4-(2''-methylpropenyloxy)-2-hydroxy]-phenyl}-6-(4-methoxyphenyl)-1,3,5-triazine; 2,4-bis{[4-(1',1',1',3',5',5',5'-heptamethyltrisilyl-2''-methyl-propyloxy)-2-hydroxy]-phenyl}-6-(4-methoxyphenyl)-1,3,5-triazine; 2,4-bis{[4-(3-(2-propyloxy)-2-hydroxy-propyloxy)-2-hydroxy]-phenyl}-6-[4-ethylcarboxy)-phenylamino]-1,3,5-triazine;
benzotriazole compounds, for example 2,2'-methylene-bis(6-(2H-benzotriazol-2-yl)-4-(1,1,3,3-tetramethylbutyl)-phenol;
trianilino-s-triazine derivatives, for example 2,4,6-trianiline-(p-carbo-2'-ethyl-1'-oxy)-1,3,5-triazine and the UV absorbers disclosed in U.S. Pat. No. 5,332,568, EP-A-517 104, EP-A-507 691, WO 93/17002 and EP-A-570 838;
2-phenylbenzimidazole-5-sulfonic acid and salts thereof;
menthyl o-aminobenzoates;
physical sunscreens coated or not as titanium dioxide, zinc oxide, iron oxides, mica, MnO, $Fe_2O_3$, $Ce_2O_3$, $Al_2O_3$, $ZrO_2$. (surface coatings: polymethylmethacrylate, methicone (methylhydrogenpolysiloxane as described in CAS 9004-73-3), dimethicone, isopropyl titanium triisostearate (as described in CAS 61417-49-0), metal soaps as magnesium stearate (as described in CAS 4086-70-8), perfluoroalcohol phosphate as C9-15 fluoroalcohol phosphate (as described in CAS 74499-44-8; JP 5-86984, JP 4-330007)). The primary particle size is an average of 15 nm-35 nm and the particle size in dispersion is in the range of 100 nm-300 nm.
aminohydroxy-benzophenone derivatives disclosed in DE 10011317, EP 1133980 and EP 1046391
phenyl-benzimidazole derivatives as disclosed in EP 1167358
the UV absorbers described in "Sunscreens", Eds. N.J. Lowe, N.A. Shaath, Marcel Dekker, Inc., New York and Basle or in Cosmetics & Toiletries (107), 50ff (1992) also can be used as additional UV protective substances.

TABLE 2

Suitable UV filter substances which can be additionally used with the UV absorbers according to the present invention

| | |
|---|---|
| DE 10013318 | T 1 pp 8-9, all Examples pp 10-13, T 2 pp 13-14, all Examples p 14, Ex A, B, C, D, E, F pp 19-20 |
| DE102004038485A1 | Formula 1 on p 2; Ex 1-4 on p 13; |
| DE102004039281A1 | Formulas I-II on p 1; Ex Ia-Iae on pp 7-12; Ex IIa-IIm on pp 14-15; Ex 1-25 on pp 42-56; |
| DE 10206562 A1 | Ex 1-3 p 10, Ex 4-7 p 11, Ex 8-15 pp 12-14 |
| DE 10238144 A1 | Ex on pp 3-5; |
| DE 10331804 | T 1 p 4, T 2 + 3 p 5 |
| DE 19704990 A1 | Ex 1-2 on pp 6-7; |
| EP 613 893 | Ex 1-5 + 15, T 1, pp 6-8 |
| EP 0 998 900 A1 | Ex on pp 4-11 |
| EP 1 000 950 | Comp. In Table 1, pp 18-21 |
| EP 1 005 855 | T 3, p 13 |
| EP 1 008 586 | Ex 1-3, pp 13-15 |
| EP 1 008 593 | Ex 1-8, pp 4-5 |
| EP 1 027 883 | Compound VII, p 3 |
| EP 1 027 883 | Comp I-VI, p3 |
| EP 1 028 120 | Ex 1-5, pp 5-13 |
| EP 1 059 082 | Ex 1; T 1, pp 9-11 |
| EP 1 060 734 | T 1-3, pp 11-14 |
| EP 1 064 922 | Compounds 1-34, pp 6-14 |
| EP 1 077 246 A2 | Ex 1-16 on pp 5-11; |
| EP 1 081 140 | Ex 1-9, pp 11-16 |
| EP 1 103 549 | Compounds 1-76, pp 39-51 |
| EP 1 108 712 | 4,5-Dimorpholino-3-hydroxypyridazine |
| EP 1 123 934 | T 3, p 10 |
| EP 1 129 695 | Ex 1-7, pp 13-14 |
| EP 1 167 359 | Ex 1, p 11 and Ex 2, p 12 |
| EP 1 232 148 B1 | Ex 4-17 on pp 3-5; |
| EP 1 258 481 | Ex 1, pp 7, 8 |
| EP 1 310 492 A1 | Ex 1-16 on pp 22-30 |
| EP 1 371 654 A1 | Ex on pp 5-7 |
| EP 1 380 583 A2 | Ex 1, p 6; |
| EP 1 423 351 A2 | Ex 1-16 on pp 31-37; |
| EP 1 423 371 A1 | T 1 on pp 4-8, Ex on p 9, Ex 1-9 on pp 36-42; |
| EP 1 454 896 A1 | Ex 1-5 on pp 10-13, Examples on pp 4-5; |
| EP 1 471 059 A1 | Ex 1-5 on pp 4-5; |
| EP 1484051 A2 | Formula III-VII on pp18-19, Ex 7-14 on pp 7-9, Ex 18-23 on pp 11-12, Ex 24-40 on pp 14-17; |
| EP 1648849 A2 | Formula 1 on p 4; Ex 1-2 on pp 13-17; Ex C10 and O10 on pp15-16; |
| EP 420 707 B1 | Ex 3, p 13 (CAS Reg. No 80142-49-0) |
| EP 503 338 | T 1, pp 9-10 |
| EP 517 103 | Ex 3, 4, 9, 10 pp 6-7 |
| EP 517 104 | Ex 1, T 1, pp 4-5; Ex 8, T 2, pp 6-8 |
| EP 626 950 | all compounds |
| EP 669 323 | Ex 1-3, p 5 |
| EP 743 309 A1 | Ex 1-12 on pp 18-24; |
| EP 780 382 | Ex 1-11, pp 5-7 |
| EP 823 418 | Ex 1-4, pp 7-8 |
| EP 826 361 | T 1, pp 5-6 |
| EP 832 641 | Ex 5 + 6 p 7; T 2, p 8 |
| EP 832 642 | Ex 22, T 3, pp 10-15; T 4, p 16 |
| EP 848944 A2 | Formulas I and II on p 1; Ex on p 8; Examples on p 10; |
| EP 852 137 | T 2, pp 41-46 |
| EP 858 318 | T 1, p 6 |
| EP 863 145 | Ex 1-11, pp 12-18 |
| EP 878 469 A1 | T 1, pp 5-7; |
| EP 895 776 | Comp. In rows 48-58, p 3; R 25 + 33, p 5 |
| EP 911 020 | T 2, pp 11-12 |
| EP 916 335 | T 2-4, pp 19-41 |
| EP 924 246 | T 2, p 9 |
| EP 933 376 | Ex 1-15, pp 10-21 |
| EP 944 624 | Ex 1 + 2, pp 13-15 |
| EP 945 125 | T 3 a + b, pp 14-15 |
| EP 95 097 | Ex 1, p 4 |
| EP 967 200 | Ex 2; T 3-5, 17-20 |
| EP 969 004 | Ex 5, T 1, pp 6-8 |
| FR 2842806 A1 | Ex I p 10, Ex II p 12 |
| FR 2861075 A1 | Ex 1-3 on pp 12-14; |
| FR 2862641 | Formula 3 on p4; Ex A-J on pp 7-9; |
| FR 2869907 A1 | Formula 1 on p 6; T 1 on p 7-8; Ex 4-39 on pp 12-35; |
| KR 2004025954 | all kojyl benzoate derivatives |
| JP 06135985 A2 | Formula 1 on p 2; Ex 1-8 on pp 7-8; |
| JP 2000319629 | CAS Reg Nos. 80142-49-0, 137215-83-9, 307947-82-6 |
| JP 2003081910 A | Ex on p 1; |
| JP 2005289916 A | Formula I on p 1; Ex Ia-Id on pp 2-3; |
| JP 2005290240 A | Formulas I on p 2, Ex II on p 2; |

TABLE 2-continued

Suitable UV filter substances which can be additionally used with the UV absorbers according to the present invention

| | |
|---|---|
| US 2003/0053966A1 | Ex on pp 3-6 |
| US 2004057912 A1 | Ex on p 7-9, Ex 1 on p 10; |
| US 2004057914 A1 | Ex on p 8-12, Ex 1 on p 12; |
| US 2004/0057911A1 | Formula I and II on p 1; formula III and IV on p3; Ex 1-3 on pp 5-6; |
| US 2004/0071640A1 | Ex 1-12 on pp 4-7; |
| US 2004/0091433A1 | Ex 1-6 on pp 14-16; |
| US 2004/0136931A1 | Ex 1-3 on p 7; |
| US 2004/0258636A1 | Ex 1-11 on pp 9-15; |
| US 2005/0019278A1 | Ex 1-9 on 6-8; |
| US 2005/0136012A1 | Formula 1 on p 2; |
| US 2005/0136014A1 | Formula a-c on 2; Examples on p 3; |
| US 2005/0201957A1 | Formula 1 on p1; Ex A, B, C, D, E, F, G on pp 2-3; |
| US 2005/0249681A1 | all compounds on pp 2-3, Ex 1 on p 6; |
| US 2005186157A1 | Formula 1 on p 1; Ex 1-6 on pp 2-4; |
| US 2005260144A1 | Formula I on p1; Formula II on p 3; Ex 1-10 on pp 8-11; |
| US 2006018848A1 | Ex a-p on pp 3-4; |
| US 2006045859A1 | Formula 1 on p 1; Ex 1-10 on pp 2-4; |
| U.S. Pat. No. 5,635,343 | all compounds on pp 5-10 |
| U.S. Pat. No. 5,332,568 | Ex 1, p 5, T 1 + 2, pp 6-8 |
| U.S. Pat. No. 5,338,539 | Ex 1-9, pp 3 + 4 |
| U.S. Pat. No. 5,346,691 | Ex 40, p 7; T 5, p 8 |
| U.S. Pat. No. 5,801,244 | Ex 1-5, pp 6-7 |
| U.S. Pat. No. 6,613,340 | Ex I, II pp 9-11, Examples on rows 28-53 p 6 |
| U.S. Pat. No. 6,800,274 B2 | Formulas I-VI and IX-XII on pp 14-18; |
| U.S. Pat. No. 6,890,520 B2 | Ex 1-10 on pp 6-9; |
| U.S. Pat. No. 6,926,887 B2 | Ex A on pp5/6; Formulas I-VIII on pp 27-29; |
| U.S. Pat. No. 6,936,735 B2 | Formulas 1-2 on p 2; formula 3-4 on p 6; |
| U.S. Pat. No. 6,962,692 B2 | Formulas VII and VIII on p 6; Formulas I, II, IV-VI, IX, X on pp 14-16; Formula III on p 19; |
| WO 0149686 | Ex 1-5, pp 16-21 |
| WO 0168047 | Tables on pp 85-96 |
| WO 0181297 | Ex 1-3, pp 9-11 |
| WO 0191695 | Formula I on p 4, T on p 8 |
| WO 0202501 A1 | Ex Ia-c, p 5 |
| WO 02069926 A1 | Ex on p 9, Ex on pp 17-23 |
| WO 02072583 | T on pp 68-70 |
| WO 02080876 | Ex 1 on pp 7-9 |
| WO 0238537 | All compounds p 3, compounds on rows 1-10 p 4 |
| WO 03004557 A1 | Ex A1-A29 on pp 36-57; |
| WO 03007906 | Ex I-XXIII, pp 42-48 |
| WO 03086341 A2 | Formula 2-21, pp 4-6; |
| WO 03092643 A1 | T on pp 34-35, compounds listed on p 16 |
| WO 03097577 A1 | Ex on pp 6-8; Ex 1-3 on pp 15-18; |
| WO 03104183 A1 | Formula I-IV on p 1; Ex 1-5 on pp 27-28; |
| WO 04000256 A1 | Ex 1-10 on p 18-24 |
| WO 04020398 A1 | Ex 1-3 on pp 14-17 |
| WO 04020398 A1 | Formulas I-VI on pp 21-24, Formula IX on p 25; |
| WO 04075871 | Ex 1-3 on pp 17-18; Ex 7-9 on pp 21-22; |
| WO 05009938 A2 | Formula I on p 1; Ex 1-2 on pp 14-15; |
| WO 05065154 A2 | Formula a-c on pp 5-6; |
| WO 05080341 A1 | Formula 1 on p 3; Examples on pp 9-13; |
| WO 05107692 A1 | Formula 1 on p 2; Ex 1-9 on pp 27-29; |
| WO 05118562 A1 | Formula I on p 4; Ex Ia-Ig on p 5; |
| WO 05121108 A1 | Formula I on p 3; Formula Ia on p 5; T 1 on p 7; Ex 3-22 on pp 11-23; |
| WO 06009451 | T 1 on pp 5-8; Formulas III and UV0 on p 9; |
| WO 06016806 | T 1 on pp 6-7; T 2 on p 10; T 3 on p 11;T 4 on p 15; |
| WO 06032741 | Formulas 1-3 on p 1; Ex a-k on pp 5-7; Ex 1-4 on pp 18-20; |
| WO 9217461 | Ex 1-22, pp 10-20 |
| WO 9220690 | Polymeric Comp in Examples 3-6 |
| WO 9301164 | T 1 + 2, pp 13-22 |
| WO 9714680 | Ex 1-3, p 10 |

(Abbreviations T: Table, R: row, Comp: compound, Ex: compound(s) of Patent Example, p: page; the generic scope of the UV absorbers is described in the left-hand column; specific compounds are indicated in the right-hand column)

TABLE 3

Suitable UV filter substances and adjuvants which can be additionally used with the UV absorbers according to the present invention

| No. | Chemical Name | CAS No. |
|---|---|---|
| 1 | (+/−)-1,7,7-trimethyl-3-[(4-methylphenyl)methylene]bicyclo-[2.2.1]heptan-2-one; p-methyl benzylidene camphor | 36861-47-9 |
| 2 | 1,7,7-trimethyl-3-(phenylmethylene)bicyclo[2.2.1]heptan-2-one; benzylidene camphor | 15087-24-8 |

TABLE 3-continued

Suitable UV filter substances and adjuvants which can be additionally used with the UV absorbers according to the present invention

| No. | Chemical Name | CAS No. |
|---|---|---|
| 3 | (2-Hydroxy-4-methoxyphenyl)(4-methylphenyl)methanone | 1641-17-4 |
| 4 | 2,4-dihydroxybenzophenone | 131-56-6 |
| 5 | 2,2',4,4'-tetrahydroxybenzophenone | 131-55-5 |
| 6 | 2-Hydroxy-4-methoxy benzophenone; | 131-57-7 |
| 7 | 2-Hydroxy-4-methoxy benzophenone-5-sulfonic acid | 4065-45-6 |
| 8 | 2,2'-dihydroxy-4,4'-dimethoxybenzophenone | 131-54-4 |
| 9 | 2,2'-Dihydroxy-4-methoxybenzophenone | 131-53-3 |
| 10 | Alpha-(2-oxoborn-3-ylidene)toluene-4-sulphonic acid and its salts; Mexoryl SL | 56039-58-8 |
| 11 | 1-[4-(1,1-dimethylethyl)phenyl]-3-(4-methoxyphenyl)propane-1,3-dione; avobenzone | 70356-09-1 |
| 12 | Methyl N,N,N-trimethyl-4-[(4,7,7-trimethyl-3-oxobicyclo[2,2,1]-hept-2-ylidene)methyl]anilinium sulphate; Mexoryl SO | 52793-97-2 |
| 22 | 3,3,5-Trimethyl cyclohexyl-2-hydroxy benzoate; homosalate | 118-56-9 |
| 23 | Isopentyl p-methoxycinnamate; isoamyl methoxy cinnamate | 71617-10-2 |
| 27 | Menthyl-o-aminobenzoate | 134-09-8 |
| 28 | Menthyl salicylate | 89-46-3 |
| 29 | 2-Ethylhexyl 2-cyano,3,3-diphenylacrylate; octocrylene | 6197-30-4 |
| 30 | 2-ethylhexyl 4-(dimethylamino)benzoate | 21245-02-3 |
| 31 | 2-ethylhexyl 4-methoxycinnamate; octyl methoxy cinnamate | 5466-77-3 |
| 32 | 2-ethylhexyl salicylate | 118-60-5 |
| 33 | Benzoic acid,4,4',4''-(1,3,5-triazine-2,4,6-triyltriimino)tris-,tris(2-ethylhexyl)ester; 2,4,6-Trianilino-(p-carbo-2'-ethylhexyl-1'-oxi)-1,3,5-triazine; octyl triazone | 88122-99-0 |
| 34 | 4-aminobenzoic acid | 150-13-0 |
| 35 | Benzoic acid, 4-amino-, ethyl ester, polymer with oxirane | 113010-52-9 |
| 38 | 2-phenyl-1H-benzimidazole-5-sulphonic acid; phenylbenzimidazolsulfonic acid | 27503-81-7 |
| 39 | 2-Propenamide, N-[[4-[(4,7,7-trimethyl-3-oxobicyclo[2.2.1]hept-2-ylidene)methyl]phenyl]methyl]-, homopolymer | 147897-12-9 |
| 40 | Triethanolamine salicylate | 2174-16-5 |
| 41 | 3,3'-(1,4-phenylenedimethylene)bis[7,7-dimethyl-2-oxo-bicyclo[2.2.1]heptane-1 methanesulfonic acid]; Cibafast H | 90457-82-2 |
| 42 | Titanium dioxide | 13463-67-7 |
| 44 | Zinc oxide | 1314-13-2 |
| 45 | 2,2'-Methylene-bis-[6-(2H-benzotriazol-2-yl)-4-(1,1,3,3-tetramethylbutyl)-phenol]; Tinosorb M | 103597-45-1 |
| 46 | Bis-Ethylhexyloxyphenol Methoxyphenyl Triazine (Tinosorb S) | 187393-00-6 |
| 47 | 1H-Benzimidazole-4,6-disulfonic acid, 2,2'-(1,4-phenylene)bis-, disodium salt | 180898-37-7 |
| 48 | Benzoic acid, 4,4'-[[6-[[4-[[(1,1-dimethylethyl)amino]carbonyl]-phenyl]amino]1,3,5-triazine-2,4-diyl]diimino]bis-, bis(2-ethyl-hexyl)ester; diethylhexyl butamido triazone; Uvasorb HEB | 154702-15-5 |
| 49 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane; Mexoryl XL | 155633-54-8 |
| 50 | Dimethicodiethylbenzalmalonate; Polysilicone 15; Parsol SLX | 207574-74-1 |
| 51 | Benzenesulfonic acid, 3-(2H-benzotriazol-2-yl)-4-hydroxy-5-(1-methylpropyl)-, monosodium salt; Tinogard HS | 92484-48-5 |
| 52 | Benzoic acid, 2-[4-(diethylamino)-2-hydroxybenzoyl]-, hexyl ester; Uvinul a plus | 302776-68-7 |
| 53 | 1-Dodecanaminium, N-[3-[[4-(dimethylamino)benzoyl]amino]-propyl]N,N-dimethyl-, salt with 4-methylbenzenesulfonic acid (1:1); Escalol HP610 | 156679-41-3 |
| 54 | 1-Propanaminium, N,N,N-trimethyl-3-[(1-oxo-3-phenyl-2-propenyl)amino]-, chloride | 177190-98-6 |
| 55 | 1H-Benzimidazole-4,6-disulfonic acid, 2,2'-(1,4-phenylene)bis- | 170864-82-1 |
| 56 | 1,3,5-Triazine, 2,4,6-tris(4-methoxyphenyl)- | 7753-12-0 |
| 57 | 1,3,5-Triazine, 2,4,6-tris[4-[(2-ethylhexyl)oxy]phenyl]- | 208114-14-1 |
| 58 | 1-Propanaminium, 3-[[3-[3-(2H-benzotriazol-2-yl)-5-(1,1-dimethylethyl)-4-hydroxyphenyl]-1-oxopropyl]amino]-N,N-diethyl-N-methyl-, methyl sulfate (salt) | 340964-15-0 |
| 59 | 2-Propenoic acid, 3-(1H-imidazol-4-yl)- | 104-98-3 |
| 60 | Benzoic acid, 2-hydroxy-, [4-(1-methylethyl)phenyl]methyl ester | 94134-93-7 |
| 61 | 1,2,3-Propanetriol, 1-(4-aminobenzoate); glyceryl PABA | 136-44-7 |
| 62 | Benzeneacetic acid, 3,4-dimethoxy-a-oxo- | 4732-70-1 |
| 63 | 2-Propenoic acid, 2-cyano-3,3-diphenyl-, ethyl ester | 5232-99-5 |
| 64 | Anthralinic acid, p-menth-3-yl ester | 134-09-8 |
| 65 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, |
| 66 | 1,3,5-Triazine-2,4,6-triamine, N,N'-bis[4-[5-(1,1-dimethylpropyl)-2-benzoxazolyl]phenyl]-N''-(2-ethylhexyl)- or Uvasorb K2A | 288254-16-0 |
| 67 | Merocyanine derivatives as described in WO 2004006878 and in IPCOM000022279D | |

TABLE 3-continued

Suitable UV filter substances and adjuvants which can be additionally used with the UV absorbers according to the present invention

| No. | Chemical Name | CAS No. |
|-----|---------------|---------|
| 68  | 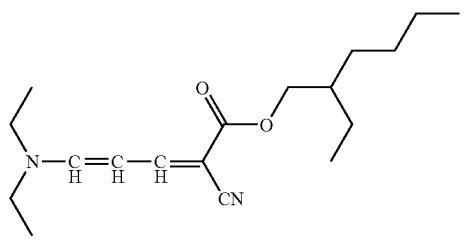 [SMILES: CCCCC(CC)COC(=O)C(C#N)=CC=CN(CC)CC] | |
| 68  | sterols (cholesterol, lanosterol, phytosterols), as described in WO0341675 | |
| 69  | mycosporines and/or mycosporine-like amino acids as described in WO2002039974, e.g. Helioguard 365 from Milbelle AG, isolated mycosporine like amino acids from the red alga porphyra umbilicalis (INCI: Porphyra Umbilicalis) that are encapsulated into liposomes,) | |
| 70  | alpha-lipoic-acid as described in DE 10229995 | |
| 71  | synthetic organic polymers as described in EP 1371358, [0033]-[0041] | |
| 72  | phyllosilicates as described in EP 1371357 [0034]-[0037] | |
| 73  | silica compounds as described in EP1371356, [0033]-[0041] | |
| 74  | inorganic particles as described in DE10138496 [0043]-[0055] | |
| 75  | latex particles as described in DE10138496 [0027]-[0040] | |
| 76  | 1H-Benzimidazole-4,6-disulfonic acid, 2,2'-(1,4-phenylene)bis-, disodium salt; Bisimidazylate; Neo Heliopan APC | 180898-37-7 |

Preferably, the following UV filter combinations are of special interest:

UV-filter combinations (A) comprising
(a₁) at least one compound of formula (1) and
(a2) at least one aminobenzophenone derivative of formula

wherein $R_1$ and $R_2$ independently from each other are; $C_1$-$C_{20}$alkyl; $C_2$-$C_{20}$alkenyl; $C_3$-$C_{10}$cycloalkyl; $C_3$-$C_{10}$cycloalkenyl; or $R_1$ and $R_2$ together with the linking nitrogen atom form a 5- or 6-membered heterocyclic ring;

$n_1$ is a number from 1 to 4;

when $n_1$=1, $R_3$ is a saturated or unsaturated heterocyclic radical; hydroxy-$C_1$-$C_5$alkyl; cyclohexyl, M optionally substituted with one or more $C_1$-$C_5$alkyl; phenyl optionally substituted with a heterocyclic radical, aminocarbonyl or $C_1$-$C_5$alkylcarboxy;

when $n_1$ is 2, $R_3$ is an alkylene-, cycloalkylene, alkenylene or phenylene radical which is optionally substituted by a carbonyl- or carboxy group; a radical of formula •—$CH_2$—C≡C—$CH_2$—• or $R_3$ together with A forms a bivalent radical of the formula

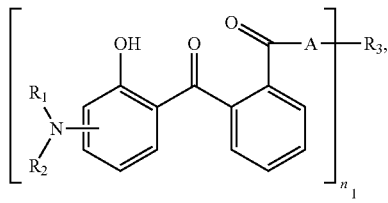

wherein $n_2$ is a number from 1 to 3;

when $n_1$ is 3, $R_3$ is an alkanetriyl radical;

wenn $n_1$ is 4, $R_3$ is an alkanetetrayl radical;

A is —O—; or —N($R_5$)—; and $R_5$ is hydrogen; $C_1$-$C_5$alkyl; or hydroxy-$C_1$-$C_5$alkyl.

UV-filter combinations (B) comprising
(b₁) one compound of formula (1); and
(b₂) at least one aminobenzophenone derivative of the formula

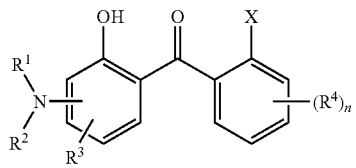

wherein $R^1$ and $R^2$ independently from each other is hydrogen, $C_1$-$C_{20}$alkyl; $C_2$-$C_{20}$alkenyl; $C_3$-$C_{10}$cycloalkenyl; wherein $R^1$ and $R^2$ may form a five- or six-membered ring;

$R^3$ and $R^4$ independently from each other is $C_1$-$C_{20}$alkyl; $C_2$-$C_{20}$alkenyl; $C_3$-$C_{10}$cycloalkenyl, $C_1$-$C_{20}$alkoxy, $C_1$-$C_{20}$alkoxycarbonyl, $C_1$-$C_{20}$alkylamino, di($C_1$-$C_{20}$alkyl)amino, optionally substituted aryl or Heteroaryl;

X is hydrogen; $COOR^5$; or $CONR^6R^7$ $R^5$, $R^6$, $R^7$ independently from each other are hydrogen, $C_1$-$C_{20}$alkyl; $C_2$-$C_{20}$alkenyl; $C_3$-$C_{10}$cycloalkyl; $C_3$-$C_{10}$cycloalkenyl; $(Y-O)_q$—Z; optionally substituted aryl;

Y is —$(CH_2)_2$—; —$(CH_2)_3$—; —$(CH_2)_4$—; —CH($CH_3$)—$CH_2$—;

Z is —$CH_2$—$CH_3$; —$CH_2$—$CH_2$—$CH_3$; —$CH_2$—$CH_2$—$CH_2$—$CH_3$; $CH(CH_3)$—$CH_3$;

m is 0; 1; 2; or 3;

n is 0; 1; 2; 3; or 4; and q is a number from 1 to 20.

UV-filter combinations (C) comprising ($c_1$) at least one compound of formula (1); and ($c_2$) at least one benzotriazole derivative of formula

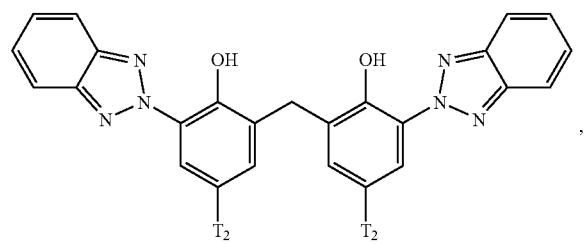

wherein $T_2$ is $C_1$-$C_{10}$alkyl or phenyl-substituted $C_1$-$C_4$alkyl;

UV-filter combinations (D) comprising ($d_1$) one compound of formula (1); and (d2) at least one compound of formula

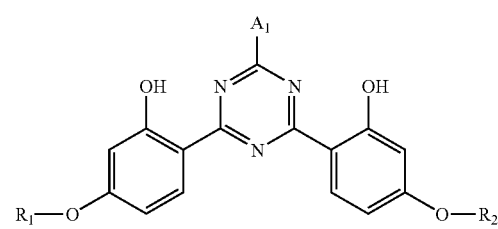

in which $R_1$ and $R_2$, independently of one another, are $C_3$-$C_{18}$alkyl; $C_2$-$C_{18}$alkenyl; a radical of the formula —$CH_2$—CH(—OH)—$CH_2$—O—$T_1$; or $R_1$ and $R_2$ are a radical of the formula

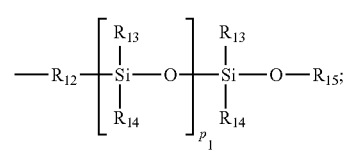

$R_{12}$ is a direct bond; a straight-chain or branched $C_1$-$C_4$alkylene radical or a radical of the formula

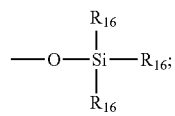

$R_{13}$, $R_{14}$ and $R_{15}$, independently of one another, are $C_1$-$C_{18}$alkyl; $C_1$-$C_{18}$alkoxy or a radical of the formula

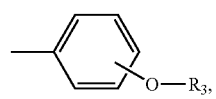

$R_{16}$ is $C_1$-$C_5$alkyl;

$m_1$ and $m_3$, independently of one another, are 1 to 4;

$p_1$ is 0; or a number from 1 to 5;

$A_1$ is a radical of the formula

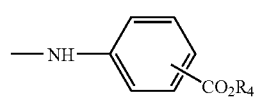

or of the formula

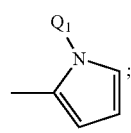

$R_3$ is hydrogen; $C_1$-$C_{10}$alkyl, —$(CH_2CHR_5$—O$)_{n_1}$—$R_4$; or a radical of the formula

—$CH_2$—CH(—OH)—$CH_2$—O-$T_1$;

$R_4$ is hydrogen; M; $C_1$-$C_5$alkyl; or a radical of the formula —$(CH_2)_{m_2}$—O-$T_1$;

$R_5$ is hydrogen; or methyl;

$T_1$ is hydrogen; or $C_1$-$C_8$alkyl;

$Q_1$ $C_1$-$C_{18}$alkyl;

M is a metal cation;

$m_2$ is 1 to 4; and $n_1$ is 1-16.

UV-filter combinations (E) comprising ($e_1$) at least one compound of formula (1); and ($e_2$) at least one hydroxyphenyltriazine compound of formula

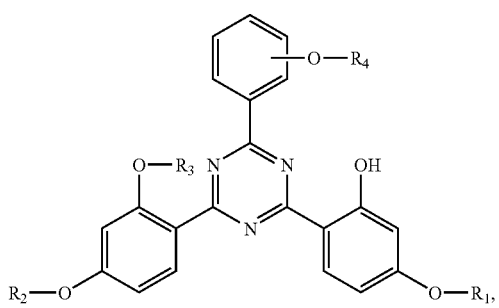

wherein
R₁, R₂ and R₃ are each independently of the others $C_1$-$C_{18}$alkyl; $C_2$-$C_{10}$alkenyl; or phenyl-$C_1$-$C_4$alkyl; and R₄ is hydrogen; or $C_1$-$C_5$alkyl.

UV-filter combinations (F) comprising
(f₁) one compound of formula (1); and
(f₂) at least one dibenzoylmethane derivative of formula

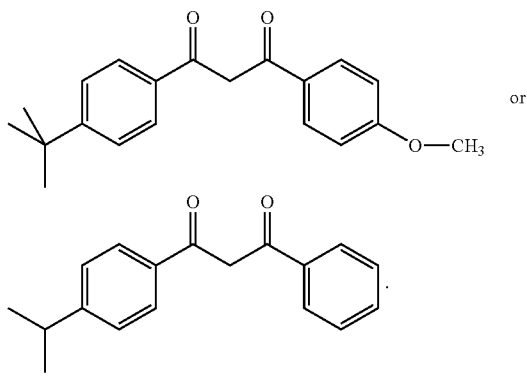

UV-filter combinations (G) comprising
(g₁) one compound of formula (1); and
(g₂) disodium phenyl dibenzimidazole tetrasulfonate (Heliopan AP).

UV-filter combinations (H) comprising
(h₁) one compound of formula (1); and
(h₂) benzoxazole-substituted triazines of formula

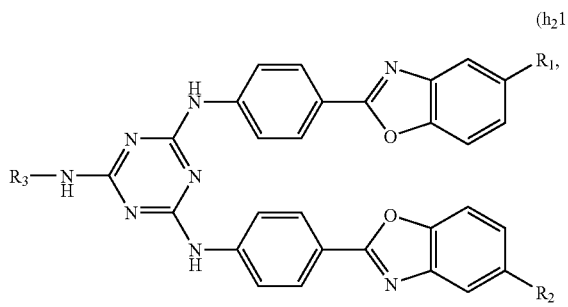

wherein
R₁, R₂ and R₃ independently from each other are branched or unbranched $C_1$-$C_{12}$alkyl.

UV-filter combinations (I) comprising
(i₁) one compound of formula (1), and
(i₂) 2-(2H-benzotriazol-2-yl)-4-methyl-6-[2-methyl-3-[1,3,3,3-tetramethyl-1-[(trimethyl-silyl)oxy]disiloxanyl]propyl]-; (CAS-No. 155633-54-8; Drometrizole Trisiloxane; Mexoryl XL);

UV-filter combinations (K) comprising
(k₁) one compound of formula (1); and
(k₂) siloxanes and silicones, di-Me, 1-[[4-[3-ethoxy-2-(ethoxycarbonyl)-3-oxo-1-propenyl]phenoxy]methyl] ethenyl Me, 3-[4-[3-ethoxy-2-(ethoxycarbonyl)-3-oxo-1-propenyl]-phenoxy]-1-propenyl Me, Me hydrogen (Dimethicodiethylbenzalmalonate; CAS-No. 207574-74-1);

UV-filter combinations (L) comprising
(l₁) one compound of formula (1); and
(l₂) (+/−)-1,7,7-trimethyl-3-[(4-methylphenyl)methylene]bicyclo[2.2.1]heptan-2-one; p-methyl benzylidene camphor;

UV-filter combinations (M) comprising
(m₁) one compound of formula (1); and
(m₂) α-(2-oxoborn-3-ylidene)toluene-4-sulphonic acid and its salts (Mexoryl SL);

UV-filter combinations (N) comprising
(n₁) one compound of formula (1); and
(n₂) methyl N,N,N-trimethyl-4-[(4,7,7-trimethyl-3-oxobicyclo[2,2,1]hept-2-ylidene)methyl]-anilinium sulphate (Mexoryl SO);

UV-filter combinations (O) comprising
(o₁) one compound of formula (1); and
(o₂) 2-ethylhexyl 2-cyano,3,3-diphenylacrylate (Octocrylene);

UV-filter combinations (P) comprising
(p₁) one compound of formula (1); and
(p₂) 2-ethylhexyl 4-methoxycinnamate (octyl methoxy cinnamate);

UV-filter combinations (Q) comprising
(q₁) one compound of formula (1); and
(q₂) benzoic acid, 4,4',4''-(1,3,5-triazine-2,4,6-triyltriimino) tris-, tris(2-ethylhexyl)ester; 2,4,6-Trianilino-(p-carbo-2'-ethylhexyl-1'-oxi)-1,3,5-triazine (Octyl Triazone);

UV-filter combinations (R) comprising
(r₁) one compound of formula (1); and
(r₂) 2-phenyl-1H-benzimidazole-5-sulphonic acid (Phenyl benzimidazolsulfonic Acid);

UV-filter combinations (S) comprising
(s₁) one compound of formula (1); and
(s₂) Diethylhexyl Butamido Triazone (Uvasorb HEB).

The one compound of formula (1) may also be used as an anti-wrinkle perception modifier (see Example 29). This is a further object of the present invention.

Preferably, the following combinations comprising UV absorbersare of special interest:

| No. | A | CAS No. of A | B: UV absorber dispersion prepared according to Example 3, 4 or 5 |
|---|---|---|---|
| Comb 001 | (+/−)-1,7,7-trimethyl-3-[(4-methyl-phenyl)methylene]bicyclo[2.2.1]heptan-2-one; p-methyl benzylidene camphor | 36861-47-9 | X |
| Comb 002 | 1,7,7-trimethyl-3-(phenylmethyllene)-bicyclo[2.2.1]heptan-2-one; benzylidene camphor | 15087-24-8 | X |
| Comb 003 | (2-Hydroxy-4-methoxyphenyl)(4-methyl-phenyl)methanone | 1641-17-4 | X |
| Comb 004 | 2,4-dihydroxybenzophenone | 131-56-6 | X |
| Comb 005 | 2,2',4,4'-tetrahydroxybenzophenone | 131-55-5 | X |
| Comb 006 | 2-Hydroxy-4-methoxy benzophenone; | 131-57-7 | X |
| Comb 007 | 2-Hydroxy-4-methoxy benzophenone-5-sulfonic acid | 4065-45-6 | X |
| Comb 008 | 2,2'-dihydroxy-4,4'-dimethoxybenzo-phenone | 131-54-4 | X |
| Comb 009 | 2,2'-Dihydroxy-4-methoxybenzophenone | 131-53-3 | X |
| Comb 010 | Alpha-(2-oxoborn-3-ylidene)toluene-4-sulphonic acid and its salts; Mexoryl SL | 56039-58-8 | X |
| Comb 011 | 1-[4-(1,1-dimethylethyl)phenyl]-3-(4-methoxyphenyl)propane-1,3-dione; Avobenzone | 70356-09-1 | X |
| Comb 012 | Methyl N,N,N-trimethyl-4-[(4,7,7-trimethyl-3-oxobicyclo[2,2,1]hept-2-ylidene)methyl]-anilinium sulphate; Mexoryl SO | 52793-97-2 | X |
| Comb 013 | 3,3,5-Trimethyl cyclohexyl-2-hydroxy benzoate; homosalate | 118-56-9 | X |
| Comb 014 | Isopentyl p-methoxycinnamate; isoamyl methoxy cinnamate | 71617-10-2 | X |
| Comb 015 | Menthyl-o-aminobenzoate | 134-09-8 | X |
| Comb 016 | Menthyl salicylate | 89-46-3 | X |
| Comb 017 | 2-Ethylhexyl 2-cyano,3,3-diphenyl-acrylate; octocrylene | 6197-30-4 | X |
| Comb 018 | 2-ethylhexyl 4-(dimethylamino)benzoate | 21245-02-3 | X |
| Comb 019 | 2-ethylhexyl 4-methoxycinnamate; octyl methoxy cinnamate | 5466-77-3 | X |
| Comb 020 | 2-ethylhexyl salicylate | 118-60-5 | X |
| Comb 021 | Benzoic acid, 4,4',4"-(1,3,5-triazine-2,4,6-triyltriimino)tris-, tris(2-ethylhexyl)-ester; 2,4,6-Trianilino-(p-carbo-2'-ethyl-hexyl-1'-oxi)-1,3,5-triazine; octyl triazone | 88122-99-0 | X |
| Comb 022 | 4-aminobenzoic acid | 150-13-0 | X |
| Comb 023 | Benzoic acid, 4-amino-, ethyl ester, polymer with oxirane | 113010-52-9 | X |
| Comb 024 | 2-phenyl-1H-benzimidazole-5-sulphonic acid; phenylbenzimidazolsulfonic acid | 27503-81-7 | X |
| Comb 025 | 2-Propenamide, N-[[4-[(4,7,7-trimethyl-3-oxobicyclo[2.2.1]hept-2-ylidene)methyl]-phenyl]methyl]-, homopolymer | 147897-12-9 | X |
| Comb 026 | Triethanolamine salicylate | 2174-16-5 | X |
| Comb 027 | 3,3'-(1,4-phenylenedimethylene)bis[7,7-dimethyl-2-oxo-bicyclo[2.2.1]heptane-1-methanesulfonic acid]; Cibafast H | 90457-82-2 | X |
| Comb 028 | Titanium dioxide | 13463-67-7 | X |
| Comb 029 | Zinc oxide | 1314-13-2 | X |
| Comb 030 | 2,2'-Methylene-bis-[6-(2H-benzotriazol-2-yl)-4-(1,1,3,3-tetramethylbutyl)-phenol]; Tinosorb M | 103597-45-1 | X |
| Comb 031 | Bis-Ethylhexyloxyphenol Methoxyphenyl Triazine (Tinosorb S) | 187393-00-6 | X |
| Comb 032 | 1H-Benzimidazole-4,6-disulfonic acid, 2,2'-(1,4-phenylene)bis-, disodium salt | 180898-37-7 | X |
| Comb 033 | Benzoic acid, 4,4'-[[6-[[4-[[(1,1-dimethyl-ethyl)amino]carbonyl]phenyl]amino]1,3,5-triazine-2,4-diyl]diimino]bis-, bis(2-ethyl-hexyl)ester; diethylhexyl butamido triazone; Uvasorb HEB | 154702-15-5 | |
| Comb 034 | Phenol, 2-(2H-benzotriazol-2-yl)-4-methyl-6-[2-methyl-3-[1,3,3,3-tetramethyl-1-[(trimethylsilyl)oxy]disiloxanyl]propyl]-; drometrizole trisiloxane; Mexoryl XL | 155633-54-8 | X |
| Comb 035 | Dimethicodiethylbenzalmalonate; Poly-silicone 15; Parsol SLX | 207574-74-1 | X |

| No. | A | CAS No. of A | B: UV absorber dispersion prepared according to Example 3, 4 or 5 |
|---|---|---|---|
| Comb 036 | Benzenesulfonic acid, 3-(2H-benzotriazol-2-yl)-4-hydroxy-5-(1-methylpropyl)-, monosodium salt; Tinogard HS | 92484-48-5 | X |
| Comb 037 | Benzoic acid, 2-[4-(diethylamino)-2-hydroxybenzoyl]-, hexyl ester; Uvinul a plus | 302776-68-7 | X |
| Comb 038 | 1-Dodecanaminium, N-[3-[[4-(dimethyl-amino)benzoyl]amino]propyl]N,N-dimethyl-, salt with 4-methylbenzene-sulfonic acid (1:1); Escalol HP610 | 156679-41-3 | X |
| Comb 039 | 1-Propanaminium, N,N,N-trimethyl-3-[(1-oxo-3-phenyl-2-propenyl)amino]-, chloride | 177190-98-6 | X |
| Comb 040 | 1H-Benzimidazole-4,6-disulfonic acid, 2,2'-(1,4-phenylene)bis- | 170864-82-1 | X |
| Comb 041 | 1,3,5-Triazine, 2,4,6-tris(4-methoxy-phenyl)- | 7753-12-0 | X |
| Comb 042 | 1,3,5-Triazine, 2,4,6-tris[4-[(2-ethyl-hexyl)oxy]phenyl]- | 208114-14-1 | X |
| Comb 043 | 1-Propanaminium, 3-[[3-[3-(2H-benzo-triazol-2-yl)-5-(1,1-dimethylethyl)-4-hydroxyphenyl]-1-oxopropyl]amino]-N,N-diethyl-N-methyl-, methyl sulfate (salt) | 340964-15-0 | X |
| Comb 044 | 2-Propenoic acid, 3-(1H-imidazol-4-yl)- | 104-98-3 | X |
| Comb 045 | Benzoic acid, 2-hydroxy-, [4-(1-methyl-ethyl)phenyl]methyl ester | 94134-93-7 | X |
| Comb 046 | 1,2,3-Propanetriol, 1-(4-aminobenzoate); glyceryl PABA | 136-44-7 | X |
| Comb 047 | Benzeneacetic acid, 3,4-dimethoxy-a-oxo- | 4732-70-1 | X |
| Comb 048 | 2-Propenoic acid, 2-cyano-3,3-diphenyl-, ethyl ester | 5232-99-5 | X |
| Comb 049 | Anthralinic acid, p-menth-3-yl ester | 134-09-8 | X |
| Comb 050 | 2,2'-bis(1,4-phenylene)-1H-benzimida-zole-4,6-disulphonic acid mono sodium salt or Disodium phenyl dibenzimidazole tetrasulfonate (Neoheliopan AP) | 349580-12-7, | X |
| Comb 051 | 1,3,5-Triazine-2,4,6-triamine, N,N'-bis[4-[5-(1,1-dimethylpropyl)-2-benzoxazolyl]-phenyl]-N''-(2-ethylhexyl)- or Uvasorb K2A | 288254-16-0 | X |
| Comb 052 | Merocyanine derivatives as described in WO 2004006878 and in IPCOM000022279D | | X |
| Comb 053 | [structure] | | X |
| Comb 054 | sterols (cholesterol, lanosterol, phyto-sterols), as described in WO0341675 | | X |
| Comb 55 | mycosporines and/or mycosporine-like amino acids as described in WO2002039974, e.g. Helioguard 365 from Milbelle AG, isolated mycosporine like amino acids from the red alga porphyra umbilicalis (INCI: Porphyra Umbilicalis) that are encapsulated into liposomes,) | | X |
| Comb 056 | alpha-lipoic-acid as described in DE 10229995 | | X |
| Comb 057 | synthetic organic polymers as described in EP 1371358, [0033]-[0041] | | X |
| Comb 058 | phyllosilicates as described in EP 1371357 [0034]-[0037] | | X |
| Comb 059 | silica compounds as described in EP1371356, [0033]-[0041] | | X |
| Comb 060 | inorganic particles as described in DE10138496 [0043]-[0055] | | X |
| Comb 061 | latex particles as described in DE10138496 [0027]-[0040] | | X |

Furthermore, the following specific UV filter combinations are of specific interest:

| No. | A | CAS No. of A | B: UV absorber dispersion prepared according to Example 3, 4 or 5 |
|---|---|---|---|
| Com 062 | (+/−)-1,7,7-trimethyl-3-[(4-methylphenyl)-methylene]bicyclo[2.2.1]heptan-2-one; p-methyl benzylidene camphor | 36861-47-9 | X |
| Com 063 | 1,7,7-trimethyl-3-(phenylmethylene)bi-cyclo[2.2.1]heptan-2-one; benzylidene camphor | 15087-24-8 | X |
| Comb 064 | (2-Hydroxy-4-methoxyphenyl)(4-methylphenyl)methanone | 1641-17-4 | X |
| Comb 065 | 2,4-dihydroxybenzophenone | 131-56-6 | X |
| Comb 066 | 2,2',4,4'-tetrahydroxybenzophenone | 131-55-5 | X |
| Comb 067 | 2-Hydroxy-4-methoxy benzophenone | 131-57-7 | X |
| Comb 068 | 2-Hydroxy-4-methoxy benzophenone-5-sulfonic acid | 4065-45-6 | X |
| Comb 069 | 2,2'-dihydroxy-4,4'-dimethoxybenzo-phenone | 131-54-4 | X |
| Comb 070 | 2,2'-Dihydroxy-4-methoxybenzophenone | 131-53-3 | X |
| Comb 071 | Alpha-(2-oxoborn-3-ylidene)toluene-4-sulphonic acid and its salts; Mexoryl SL | 56039-58-8 | X |
| Comb 072 | 1-[4-(1,1-dimethylethyl)phenyl]-3-(4-methoxyphenyl)propane-1,3-dione; avo-benzone | 70356-09-1 | X |
| Comb 073 | Methyl N,N,N-trimethyl-[(4,7,7-trimethyl-3-oxobicyclo[2,2,1]hept-2-ylidene)methyl]-anilinium sulphate; Mexoryl SO | 52793-97-2 | X |
| Comb 074 | 3,3,5-Trimethyl cyclohexyl-2-hydroxy benzoate; homosalate | 118-56-9 | X |
| Comb 075 | Isopentyl p-methoxycinnamate; isoamyl methoxy cinnamate | 71617-10-2 | X |
| Comb 076 | Menthyl-o-aminobenzoate | 134-09-8 | X |
| Comb 077 | Menthyl salicylate | 89-46-3 | X |
| Comb 078 | 2-Ethylhexyl 2-cyano,3,3-diphenylacrylate; octocrylene | 6197-30-4 | X |
| Comb 079 | 2-ethylhexyl 4-(dimethylamino)benzoate | 21245-02-3 | X |
| Comb 080 | 2-ethylhexyl 4-methoxycinnamate; octyl methoxy cinnamate | 5466-77-3 | X |
| Comb 081 | 2-ethylhexyl salicytate | 118-60-5 | X |
| Comb 082 | Benzoic acid,4,4',4''-(1,3,5-triazine-2,4,6-triyltriimino)tris-,tris(2-ethylhexyl)ester; 2,4,6-Trianilino-(p-carbo-2'-ethylhexyl-1'-oxi)-1,3,5-triazine; octyl triazone | 88122-99-0 | X |
| Comb 083 | 4-aminobenzoic acid | 150-13-0 | X |
| Comb 084 | Benzoic acid, 4-amino-, ethyl ester, polymer with oxirane | 113010-52-9 | X |
| Comb 085 | 2-phenyl-1H-benzimidazole-5-sulphonic acid; phenylbenzimidazolsulfonic acid | 27503-81-7 | X |
| Comb 086 | 2-Propenamide, N-[[4-[(4,7,7-trimethyl-3-oxobicyclo[2.2.1]hept-2-ylidene)methyl]-phenyl]methyl]-, homopolymer | 147897-12-9 | X |
| Comb 087 | Triethanolamine salicylate | 2174-16-5 | X |
| Comb 088 | 3,3'-(1,4-phenylenedimethylene)bis[7,7-dimethyl-2-oxo-bicyclo[2.2.1]heptane-1-methanesulfonic acid]; Cibafast H | 90457-82-2 | X |
| Comb 089 | Titanium dioxide | 13463-67-7 | X |
| Comb 090 | Zinc oxide | 1314-13-2 | X |
| Comb 091 | 2,2'-Methylene-bis-[6-(2H-benzotriazol-2-yl)-4-(1,1,3,3-tetramethylbutyl)-phenol]; Tinosorb M | 103597-45-1 | X |
| Comb 092 | Bis-Ethylhexyloxyphenol Methoxyphenyl Triazine (Tinosorb S) | 187393-00-6 | X |
| Comb 093 | 1H-Benzimidazole-4,6-disulfonic acid, 2,2'-(1,4-phenylene)bis-, disodium salt | 180898-37-7 | X |
| Comb 094 | Benzoic acid, 4,4'-[[6-[[(1,1-dimethyl-ethyl)amino]carbonyl]phenyl]amino]1,3,5-triazine-2,4-diyl]diimino]bis-, bis(2-ethyl-hexyl)ester; diethylhexyl butamido tria-zone; Uvasorb HEB | 154702-15-5 | X |
| Comb 095 | Phenol, 2-(2H-benzotriazol-2-yl)-4-methyl-6-[2-methyl-3-[1,3,3,3-tetramethyl-1-[(tri-methylsilyl)oxy]disiloxanyl]propyl]-; drometrizole trisiloxane; Mexoryl XL | 155633-54-8 | X |

-continued

| No. | A | CAS No. of A | B: UV absorber dispersion prepared according to Example 3, 4 or 5 |
|---|---|---|---|
| Comb 096 | Dimethicodiethylbenzalmalonate; Polysilicone 15; Parsol SLX | 207574-74-1 | X |
| Comb 097 | Benzenesulfonic acid, 3-(2H-benzotriazol-2-yl)-4-hydroxy-5-(1-methylpropyl)-, monosodium salt; Tinogard HS | 92484-48-5 | X |
| Comb 098 | Benzoic acid, 2-[4-(diethylamino)-2-hydroxy-benzoyl]-, hexyl ester; Uvinul A Plus | 302776-68-7 | X |
| Comb 099 | 1-Dodecanaminium, N-[3-[[4-(dimethyl-amino)benzoyl]amino]propyl]N,N-dimethyl-, salt with 4-methylbenzenesulfonic acid (1:1) (Escalol HP610) | 156679-41-3 | X |
| Comb 100 | 1-Propanaminium, N,N,N-trimethyl-3-[(1-oxo-3-phenyl-2-propenyl)amino]-, chloride | 177190-98-6 | X |
| Comb 101 | 1H-Benzimidazole-4,6-disulfonic acid, 2,2'-(1,4-phenylene)bis- | 170864-82-1 | X |
| Comb 102 | 1,3,5-Triazine, 2,4,6-tris(4-methoxyphenyl)- | 7753-12-0 | X |
| Comb 103 | 1,3,5-Triazine, 2,4,6-tris[4-[(2-ethylhexyl)-oxy]phenyl]- | 208114-14-1 | X |
| Comb 104 | 1-Propanaminium, 3-[[3-[3-(2H-benzo-triazol-2-yl)-5-(1,1-dimethylethyl)-4-hydroxyphenyl]-1-oxopropyl]amino]-N,N-diethyl-N-methyl-, methyl sulfate (salt) | 340964-15-0 | X |
| Comb 105 | 2-Propenoic acid, 3-(1H-imidazol-4-yl)- | 104-98-3 | X |
| Comb 106 | Benzoic acid, 2-hydroxy-, [4-(1-methylethyl)phenyl]methyl ester | 94134-93-7 | X |
| Comb 107 | 1,2,3-Propanetriol, 1-(4-aminobenzoate); glyceryl PABA | 136-44-7 | X |
| Comb 108 | Benzeneacetic acid, 3,4-dimethoxy-a-oxo- | 4732-70-1 | X |
| Comb 109 | 2-Propenoic acid, 2-cyano-3,3-diphenyl-, ethyl ester | 5232-99-5 | X |
| Comb 110 | Anthralinic acid, p-menth-3-yl ester | 134-09-8 | X |
| Comb 111 | 2,2'-bis(1,4-phenylene)-1H-benzimidazole-4,6-disulphonic acid mono sodium salt or Disodium phenyl dibenzimidazole tetrasulfonate or Neoheliopan AP | 349580-12-7, | X |
| Comb 112 | 1,3,5-Triazine-2,4,6-triamine, N,N'-bis[4-[5-(1,1-dimethylpropyl)-2-benzoxazolyl] phenyl]-N''-(2-ethylhexyl)- or Uvasorb K2A | 288254-16-0 | X |
| Comb 113 | Merocyanine derivatives as described in WO 2004006878 and 1PCOM000022279D | | X |
| Comb 114 | (structure shown) | | X |
| Comb 115 | sterols (cholesterol, lanosterol, phyto-sterols), as described in WO0341675 | | X |
| Comb 116 | mycosporines and/or mycosporine-like amino acids as described in WO2002039974, e.g. Helioguard 365 from Milbelle AG, isolated mycosporine like amino acids from the red alga porphyra umbilicalis (INCI: Porphyra Umbilicalis) that are encapsulated into liposomes,) | | X |
| Comb 117 | alpha-lipoic-acid as described in DE 10229995 | | X |
| Comb 118 | synthetic organic polymers as described in EP 1371358, [0033]-[0041] | | X |
| Comb 119 | phyllosilicates as described in EP 1371357 [0034]-[0037] | | X |
| Comb 120 | silica compounds as described in EP1371356, [0033]-[0041] | | X |
| Comb 121 | inorganic particles as described in DE10138496 [0043]-[0055] | | X |
| Comb 122 | latex particles as described in DE10138496 [0027]-[0040] | | X |

Furthermore, the following specific UV filter combinations are of specific interest:

| No. | UV filter (A) | UV filter (B) | UV filter (C) |
|---|---|---|---|
| Comb 124 | 2-ethylhexyl 4-methoxy-cinnamate; octyl methoxy cinnamate | micronized UV absorber of formula (103) | micronized UV absorber of formula (7a), (7b) or (7d) |
| Comb 125 | 2-ethylhexyl 4-methoxycinnamate; octyl methoxy cinnamate | Benzoic acid, 2-[4-(diethyl-amino)-2-hydroxybenzoyl]-, hexyl ester; Uvinul a plus | micronized UV absorber of formula (7a), (7b) or (7d) |
| Comb 126 | 2-ethylhexyl 4-methoxy-cinnamate; octyl methoxy cinnamate | Benzoic acid, 2-[4-(diethyl-amino)-2-hydroxybenzoyl]-, hexyl ester; Uvinul a plus | micronized UV absorber of formula (7a), (7b) or (7d) |
| Comb 127 | 2-ethylhexyl 4-methoxy-cinnamate; octyl methoxy cinnamate | Benzoic acid, 4,4'-[[6-[[4-[[(1,1-dimethylethyl)amino]-carbonyl]phenyl]amino]1,3,5-triazine-2,4-diyl]diimino]bis-, bis(2-ethylhexyl)ester; di-ethylhexyl butamido triazone; Uvasorb HEB | micronized UV absorber of formula (7a), (7b) or (7d) |
| Comb 128 | 2-ethylhexyl 4-methoxy-cinnamate; octyl methoxy cinnamate | 2,2'-bis(1,4-phenylene)-1H-benzimidazole-4,6-disulphonic acid mono sodium salt or Disodium phenyl dibenzimidazole tetrasulfonate or Neoheliopan AP | micronized UV absorber of formula (7a), (7b) or (7d) |
| Comb 129 | 2-ethylhexyl 4-methoxy-cinnamate; octyl methoxy cinnamate | 2-Ethylhexyl 2-cyano,3,3-diphenylacrylate; Octocrylene | micronized UV absorber of formula (7a), (7b) or (7d) |
| Comb 130 | 2-ethylhexyl 4-methoxy-cinnamate; octyl methoxy cinnamate | Benzoic acid, 4,4',4''-(1,3,5-triazine-2,4,6-triyltri-imino)tris-, tris(2-ethyl-hexyl)ester; 2,4,6-Trianilino-(p-carbo-2'-ethylhexyl-1'-oxi)-1,3,5-triazine; octyl triazone | |
| Comb 131 | 2-ethylhexyl 4-methoxy-cinnamate; octyl methoxy cinnamate | 2-phenyl-1H-benzimidazole-5-sulphonic acid; phenylbenzimidazolsulfonic acid | micronized UV absorber of formula (7a), (7b) or (7d) |
| Comb 132 | 2-ethylhexyl 4-methoxy-cinnamate; octyl methoxy cinnamate | 1-[4-(1,1-dimethylethyl)phenyl]-3-(4-methoxyphenyl)-propane-1,3-dione; avobenzone | micronized UV absorber of formula (7a), (7b) or (7d) |
| Comb 133 | 2-ethylhexyl 4-methoxy-cinnamate; octyl methoxy cinnamate | Phenol, 2-(2H-benzotriazol-2-yl)-4-methyl-6-[2-methyl-3-[1,3,3,3-tetramethyl-1-[(tri-methylsilyl)oxy]disiloxanyl]propyl]-; drometrizole trisiloxane; Mexoryl XL | micronized UV absorber of formula (7a), (7b) or (7d) |
| Comb 134 | 2-ethylhexyl4-methoxycinnamate; octyl methoxy cinnamate | Dimethicodiethylbenzalmalonate; Polysilicone 15; Parsol SLX | micronized UV absorber of formula (7a), (7b) or (7d) |
| Comb 135 | 2-ethylhexyl 4-methoxy-cinnamate; octyl methoxy cinnamate | 2,2'-Methylene-bis-[6-(2H-benzotriazol-2-yl)-4-(1,1,3,3-tetramethylbutyl)-phenol]; Tinosorb M | micronized UV absorber of formula (7a), (7b) or (7d) |
| Comb 136 | 2-ethylhexyl 4-methoxy-cinnamate; octyl methoxy cinnamate | Bis-Ethylhexyloxyphenol Methoxyphenyl Triazine (Tinosorb S) | micronized UV absorber of formula (7a), (7b) or (7d) |
| Comb 137 | Bis-Ethylhexyloxyphenol Methoxyphenyl Triazine (Tinosorb S) | 2,2'-Methylene-bis-[6-(2H-benzotriazol-2-yl)-4-(1,1,3,3-tetramethylbutyl)-phenol]; Tinosorb M | micronized UV absorber of formula (7a), (7b) or (7d) |
| Comb 138 | Benzoic acid, 2-[4-(diethylamino)-2-hydroxybenzoyl]-, hexyl ester; Uvinul a plus | 1-[4-(1,1-dimethylethyl)phenyl]-3-(4-methoxyphenyl)-propane-1,3-dione; avobenzone | micronized UV absorber of formula (7a), (7b) or (7d) |
| Comb 139 | Bis-Ethylhexyloxyphenol Methoxyphenyl Triazine (Tinosorb S) | 1-[4-(1,1-dimethylethyl)phenyl]-3-(4-methoxyphenyl)-propane-1,3-dione; avobenzone | micronized UV absorber of formula (7a), (7b) or (7d) |
| Comb 140 | 1-[4-(1,1-dimethylethyl)-phenyl]-3-(4-methoxy-phenyl)propane-1,3-dione; avobenzone | 2,2'-bis(1,4-phenylene)-1H-benzimidazole-4,6-disulphonic acid mono sodium salt or Disodium phenyl di-benzimidazole tetrasulfonate or Neoheliopan AP | micronized UV absorber of formula (7a), (7b) or (7d) |

Combinations of Active Ingredients in Cosmetic or Dermatological Formulations

These formulations comprise at least a water phase and/or an oil-phase. They may be formulated as o/w, w/o, w/o/w, o/w/o or silicone/w, w/silicone emulsions or microemulsions. They may contain low molecular weight emulsifiers selected from non-ionic, cationic, amphoteric and anionic emulsifiers from 0.1 to 20% bw.

The emulsifier in these formulations may be replaced by an associative polymer (0.1 to 10% bw).

The formulation form may be a sun milk, cream, spray or foam application. Also oil-free gel formulations are possible.

Other ingredients of these formulations are water, emollients, thickening agents and others as described in the chapters below.

EXAMPLES

1. Amphiphilic particles<200 nm in an emulsifier free cosmetic formulation combined with 0.1% to 10% of microfine (particle size between 10 nm and 2 μm) naphthalene amidine imide compound

| Example 1.1: | [g] |
|---|---|
| $C_{12-15}$ Alkylbenzoate | 10.00 |
| micronized UV absorber of formula (7a), (7b) or (7d) | 2.50 |
| Octocrylene | 5.00 |
| 4-tert-butyl-4'-methoxydibenzoylmethane (PARSOL 1789) | 2.00 |
| Acrylates/C10-30 Alkyl Acrylate Crosspolymer (Pemulen TR1) | 0.75 |
| Titanium Dioxide | 3.00 |
| EDTA | 0.10 |
| 1,4-benzene[di(3-methylidene-10-camphorsulfonic)] acid (MEXORYL SX) | 0.50 |
| Glycerin | 5.00 |
| Triethanolamine, preservatives pH = 7 | q.s. |
| Demineralized water | ad 100 |

2. Flavon-derivatives combined with 0.1% to 10% of microfine (particle size between 10 nm and 2 μm) naphthalene amidine imide compound

|  | % b.w. |
|---|---|
| Example 2.1: O/W-Emulsion | |
| Stearic Acid | 1.50 |
| Glycerin Monostearate | 3.00 |
| Capric acid/Capric acid glyceride | 10.00 |
| Dicaprylic ether | 5.00 |
| Dimethicone | 2.00 |
| Hydrated polyisobutene | 2.00 |
| Vitamin E Acetate | 0.50 |
| Dioctyl Butamido Triazone | 4.00 |
| Bis-Ethylhexyloxyphenol Methoxyphenyl Triazine (Tinosorb S) | 1.00 |
| 4-Methylbenzylidene Camphor | 4.00 |
| Titanium Dioxide | 1.00 |
| α-Glucosylrutin | 1.00 |
| Preservative | 0.50 |
| Glycerin | 3.00 |
| micronized UV absorber of formula (7a), (7b) or (7d) | 1.00 |
| Xanthan Gum | 0.30 |
| NaOH 45% | 0.50 |
| Water | ad 100.00 |
| Example 2.2: O/W-Emulsion | |
| Sorbitan Stearate | 3.00 |
| Polyglyceryl-3 Methylglucose Distearate | 1.50 |
| Octyldodecanol | 10.00 |
| Dicaprylyl Ether | 5.00 |
| Mineral Oil | 5.00 |
| Ricinus Oil | 2.00 |
| Butylene Glycol Dicaprylate/Dicaprate | 5.00 |
| Vitamin-E Acetate | 0.50 |
| Octyltriazone | 4.00 |
| Octocrylene | 8.00 |
| 4-Methylbenzylidene Camphor | 4.00 |
| Butyl Methoxydibenzoylmethane | 3.00 |
| α-Glucosylrutin | 1.00 |
| Boron Nitride | 2.00 |
| Preservative | 0.50 |
| Glycerin | 10.00 |
| micronized UV absorber of formula (7a), (7b) or (7d) | 1.50 |
| Xanthan Gum | 0.20 |
| Permulen TR1 | 0.10 |
| Phenylbenzimidazole Sulfonic Acid | 2.00 |
| NaOH 45% | 1.20 |
| Water | ad 100.00 |
| Example 2.3: W/O-Emulsion | |
| Polyglyceryl-2-dipolyhydroxystearate | 5.00 |
| Dimethicone | 2.00 |
| Mineral Oil | 5.00 |
| Isohexadecane | 5.00 |
| Butylene Glycol Dicaprylate/Dicaprate | 10;00 |
| $C_{12-15}$ Alkylbenzoate | 7.00 |
| Dioctyl Butamido Triazone | 3.00 |
| 4-Methylbenzylidene Camphor | 2.00 |
| Butyl Methoxydibenzoylmethane | 2.00 |
| Titanium Dioxide | 4.00 |
| α-Glucosylrutin | 0:50 |
| Preservative | 0:50 |
| Glycerin | 5:00 |
| micronized UV absorber of formula (7a), (7b) or (7d) | 4.50 |
| $MgS0_4$ | 1.00 |
| Water | ad 100.00 |
| Example 2.4: W/0-Emulsion | |
| PEG-30 Dipolyhydroxystearate | 4:00 |
| Caprylic Acid/Capric Acid Triglyceride | 5.00 |
| Octyldodecanol | 5.00 |
| Dicaprylyl Ether | 5.00 |
| Mineral Oil | 5.00 |
| Isohexadecane | 2.00 |
| $C_{12-15}$ Alkylbenzoate | 10.00 |
| Hydrated Polyisobutene | 5.00 |
| Vitamin-E-Acetate | 0.50 |
| Dioctyl Butamido Triazone | 1.00 |
| Aerosil R 972 | 0.50 |
| α-Glucosylrutin | 0.20 |
| Preservative | 0.50 |
| Glycerin | 10.00 |
| micronized UV absorber of formula (7a), (7b) or (7d) | 3.00 |
| $MgS0_4$ | 1.00 |
| Water | ad 100.00 |
| Example 2.5: Hydrodispersion | |
| Caprylic Acid/Capric Acid Triglyceride | 10.00 |
| Cetyldodecanol | 5.00 |
| Dicaprylyl Ether | 2.00 |
| Dimethicone | 1.00 |
| Vitamin-E Acetate | 0.50 |
| Octyltriazone | 2.00 |
| 4-Methylbenzylidene Camphor | 4.00 |
| Butyl Methoxydibenzoylmethane | 2.00 |
| Titanium Dioxide | 1.00 |
| α-Glucosylrutin | 0.75 |
| Preservative | 0:50 |
| Glycerin | 3.00 |
| micronized UV absorber of formula (7a), (7b) or (7d) | 2.20 |
| Xanthan Gum | 0.40 |
| Crosslinked Acrylic Acid/($C_{10-30}$) Alkyl Acrylate Copolymer copolymer | 0.40 |
| Water | ad 100.00 |

-continued

| | % b.w. |
|---|---|
| Example 2.07: W/0-Pickering emulsion | |
| Caprylic Acid/Capric Acid Triglyceride | 15:00 |
| Hydrated Polyisobutene | 5.00 |
| $C_{12-15}$ Alkylbenzoate | 5:00 |
| Dioctyl Butamido Triazone | 2.00 |
| Octyltriazone | 2.00 |
| Titanium Dioxide | 4:00 |
| Aerosil R 972 | 2.00 |
| α-Glucosylrutin | 0:20 |
| Boron Nitride | 1:00 |
| Preservative | 0..50 |
| Glycerin | 5:00 |
| micronized UV absorber of formula (7a), (7b) or (7d) | 5.00 |
| NaCl | 1:00 |
| Water | ad 100.00 |
| Example 2.08: Spray | |
| Glycerinmonostearate | 4.00 |
| Ceteareth-12 | 1.50 |
| Caprylic Acid/Capric Acid Triglyceride | 2.00 |
| Mineral Oil | 5.00 |
| Octocrylene | 1.00 |
| Octyltriazone | 6.00 |
| α-Glucosylrutin | 1.00 |
| Preservative | 0.50 |
| Glycerin | 10.00 |
| micronized UV absorber of formula (7a), (7b) or (7d) | 0.80 |
| Phenylbenzimidazole Sulfonic Acid | 1.00 |
| NaOH 45% | 0.40 |
| Water | ad 100.00 |

3. Dialkylnaphthalates combined with 0.1% to 10% of micro-fine (particle size between 10 nm and 2 μm) naphthalene amidine imide compound

| Example 3.1-3.5 | Example 3.1 O/W 1 | Example 3.2 O/W 2 | Example 3.3 W/O 1 | Example 3.4 W/O 2 | Example 3.5 W/O 3 |
|---|---|---|---|---|---|
| Stearic Acid | 1.50 | | | | |
| Glycerol monostearate | 3.00 | | | | |
| Sorbitan Stearate | | 3.00 | | | |
| Polyglyceryl-3 Methylglucose Distearate | | 1.50 | | | |
| Polyglyceryl-2 Dipolyhydroxystearate | | | 5.00 | | |
| Cetyl Dimethicone copolyol | | | | | 5.00 |
| PEG-30 Dipolyhydroxystearate | | | | 4.00 | |
| Dimethicone | 2.00 | | | | |
| Phenyl Trimethicone | 2.00 | | 5.00 | | 3.00 |
| Vitamin-E Acetate | 0.50 | 0.50 | | 0.50 | |
| Dioctyl Butamido Triazone | 3.00 | | 3.00 | | 5.00 |
| Aniso Triazine | | 3.00 | 2.00 | 5.00 | 2.00 |
| Aerosil R 972 | | | | 0.50 | |
| Diethylhexyl 2,6-Naphthalate (Halbrite TQ) | 6.00 | 8.00 | 5.00 | 4.00 | 7.00 |
| Preservative | 0.50 | 0.50 | 0.50 | 0.50 | 0.50 |
| Glycerin | 3.00 | 10.00 | 5.00 | 10.00 | 5.00 |
| micronized UV absorber of formula (7a), (7b) or (7d) | 0.50 | 0.80 | 1.50 | 2.00 | 3.00 |
| $MgSO_4$ | | | 1.00 | 1.00 | |
| NaCl | | | | | 1.00 |
| Xanthan Gum | 0.30 | | | | |
| Permulen TR1 | | 0.10 | | | |
| NaOH 45% | 0.50 | 1.20 | | | 1.30 |
| Water | ad 100.00 | ad 100.00 | ad 100.00 | ad 100.00 | ad 100.00 |

4. Glycerid-waxes or triglycerid waxes combined with 0.1% to 10% of micro-fine (particle size between 10 nm and 2 μm) naphthalene amidine imide compound

| | % b.w. |
|---|---|
| Example 4.1: O/W Emulsion | |
| Stearic Acid | 1.50 |
| Glycerin Monostearate | 3.00 |
| Caprylic Acid/Capric Acid Triglyceride | 10.00 |
| Dicaprylyl Ether | 5.00 |
| Hydrated Polyisobutene | 2.00 |
| Vitamin-E Acetate | 0.50 |
| Octyltriazone | 2.00 |
| Dioctyl Butamido Triazone | 2.00 |
| Butyl Methoxydibenzoylmethane | 2.00 |
| Titanium Dioxide | 1.00 |
| $C_{18-36}$ Triglyceride | 5.00 |
| micronized UV absorber of formula (7a), (7b) or (7d) | 5.80 |
| Xanthan Gum | 0.30 |
| NaOH 45% | 0.50 |
| Preservative, Perfume, Dyes | q.s. |
| Water | ad 100.00 |
| Example 4.2: Oil Gel | |
| Caprylic Acid/Gapric Acid Triglyceride | 5.00 |
| Dicaprylyl Ether | 5.00 |
| Dimethicone | 5.00 |
| Mineral Oil | 30.00 |
| Isohexadecane | 10.00 |
| Hydrated Polyisobutene | 20.00 |
| Butylene Glycol Dicaprylate/Dicaprate | 5.00 |
| $C_{12-15}$ Alkylbenzoate | 5.00 |
| Vitamin-E Acetate | 0.50 |
| Octyltriazone | 2.00 |

-continued

| | % b.w. |
|---|---|
| Butyl Methoxydibenzoylmethane | 1.00 |
| Aerosil R 972 | 1.00 |
| $C_{18-38}$ Triglyceride | 10.00 |
| micronized UV absorber of formula (7a), (7b) or (7d) | 0.50 |
| Preservative, Parfume, Dyes, Water | q.s. |

5. Octocrylene combined with 0.1% to 10% of micro-fine (particle size between 10 nm and 2 μm) naphthalene amidine imide compound

| | % b.w. |
|---|---|
| Example 5.1: O/W Emulsion | |
| Stearic Acid | 1.50 |
| Glyceryl Monostearate | 3.00 |
| Caprylic Acid/Capric Acid Triglyceride | 10.00 |
| Dicaprylyl Ether | 5.00 |
| Dimethicone | 2.00 |
| Hydrated Polyisobutene | 2.00 |
| Vitamin-E Acetate | 0.50 |
| Octocrylene | 10.00 |
| Bis-Ethlhexyloxyphenol Methoxyphenyl Triazine (Tinosorb S) | 4.00 |
| 4-Methylbenzylidene Camphor | 4.00 |
| Titanium Dioxide | 1.00 |
| Preservative | q.s. |
| Glycerin | 3.00 |
| micronized UV absorber of formula (7a), (7b) or (7d) | 7.50 |
| Xanthan Gum | 0.30 |
| NaOH 45% | 0.50 |
| Water | ad 100.00 |
| Example 5.3: O/W Emulsion | |
| Sorbitan Stearate | 3.00 |
| Polyglyceryl-3 Methylglucose Distearate | 1.50 |
| Octyldodecanol | 10.00 |
| Dicaprylyl Ether | 5.00 |
| Mineral Oil | 5.00 |
| Castor Oil | 2.00 |
| Butylene Glycol Dicaprylate/Dicaprate | 5.00 |
| Vitamin E Acetate | 0.50 |
| Octocrylene | 8.00 |
| Bis-Ethlhexyloxyphenol Methoxyphenyl Triazine (Tinosorb S) | 1.50 |
| Octyltriazone | 4.00 |
| 4-Methylbenzylidene Camphor | 3.00 |
| Butyl Methoxydibenzoylmethane | 4.00 |
| Preservative | q.s. |
| Glycerol | 10.00 |
| micronized UV absorber of formula (7a), (7b) or (7d) | 8.00 |
| Xanthan Gum | 0.20 |
| Acrylates/C10-30 Alkyl Acrylate Crosspolymer (Pemulen TR1) | 2.00 |
| Phenylbenzimidazole Sulfonic Acid | 0.10 |
| NaOH 45% | 1.20 |
| Water | ad 100.00 |
| Polyglyceryl-2 Dipolyhydroxystearate | 5.00 |
| Dimethicone | 2.00 |
| Mineral Oil | 5.00 |
| Isohexadecane | 5.00 |
| Butylene Glycol Dicaprylate/Dicaprate | 5.00 |
| Dioctyl Butamido Triazone | 3.00 |
| Octocrylene | 12.00 |
| Bis-Ethlhexyloxyphenol Methoxyphenyl Triazine (Tinosorb S) | 3.00 |
| 4-Methylbenzylidene Camphor | 2.00 |
| Butyl Methoxydibenzoylmethane | 2.00 |
| Titanium Dioxide | 4.00 |
| Preservative | q.s. |
| Glycerol | 5.00 |
| micronized UV absorber of formula (7a), (7b) or (7d) | 2.00 |
| $MgSO_4$ | 1.00 |
| Water | ad 100.00 |

-continued

| | % b.w. |
|---|---|
| Example 5.4: W/O Emulsion | |
| PEG-30 Dipolyhydroxystearate | 4.00 |
| Caprylic Acid/Capric Acid Triglyceride | 5.00 |
| Octyldodecanol | 5.00 |
| Dicaprylyl Ether | 5.00 |
| Mineral Oil | 5.00 |
| Hydrated Polyisobutene | 5.00 |
| Vitamin E Acetate | 0.50 |
| Dioctyl Butamido Triazone | 1.00 |
| Octocrylene | 6.00 |
| Bis-Ethlhexyloxyphenol Methoxyphenyl Triazine (Tinosorb S) | 2.00 |
| Aerosil R 972 | 0.50 |
| Preservative | 0.50 |
| Glycerol | 10.00 |
| micronized UV absorber of formula (7a), (7b) or (7d) | 1.80 |
| $MgSO_4$ | 1.00 |
| Water | ad 100.00 |
| Example 5.5: W/O Emulsion | |
| Cetyldimethicone Copolyol | 5.00 |
| Dimethicone | 5.00 |
| Mineral Oil | 2.00 |
| Isohexadecane | 2.00 |
| $C_{12-15}$ Alkylbenzoate | 5.00 |
| Octocrylene | 15.00 |
| Bis-Ethlhexyloxyphenol Methoxyphenyl Triazine (Tinosorb S) | 6.00 |
| 4-Methylbenzylidene Camphor | 4.00 |
| Butyl Methoxydibenzoylmethane | 2.00 |
| Titanium Dioxide | 2.00 |
| Preservative | q.s. |
| Glycerol | 5.00 |
| micronized UV absorber of formula (7a), (7b) or (7d) | 1.30 |
| NaCl | 1.00 |
| Phenylbenzimidazole Sulfonic Acid | 4.00 |
| NaOH 45% | 1.30 |
| Water | ad 100.00 |
| Example 5.6: Hydrodispersion | |
| Caprylic Acid/Capric Acid Triglyceride | 10.00 |
| Octyldodecanol | 5.00 |
| Dicaprylyl Ether | 2.00 |
| Dimethicone | 1.00 |
| Vitamin E Acetate | 0.50 |
| Octyltriazone | 2.00 |
| 4-Methylbenzylidene Camphor | 4.00 |
| Butyl Methoxydibenzoylmethane | 2.00 |
| Titanium Dioxide | 1.00 |
| Preservative | q.s. |
| Glycerol | 3.00 |
| micronized UV absorber of formula (7a), (7b) or (7d) | 0.90 |
| Xanthan Gum | 0.40 |
| Acrylates/C10-30 Alkyl Acrylate Crosspolymer (Pemulen TR1) | 0.40 |
| NaOH 45% | 0.40 |
| Water | ad 100.00 |
| Example 5.7: W/O Pickering Emulsion | |
| Caprylic Acid/Capric Acid Triglyceride | 15.00 |
| Hydrated Polyisobutene | 5.00 |
| $C_{12-15}$ Alkylbenzoate | 5.00 |
| Octocrylene | 10.00 |
| Bis-Ethlhexyloxyphenol Methoxyphenyl Triazine (Tinosorb S) | 4.00 |
| Titanium Dioxide | 4.00 |
| Aerosil R 972 | 2.00 |
| Preservative | 0.50 |
| Glycerol | 5.00 |
| micronized UV absorber of formula (7a), (7b), or (7d) | 1.10 |
| NaCl | 1.00 |
| Phenylbenzimidazole Sulfonic Acid | 1.00 |
| NaOH 45% | 0.40 |
| Water | ad 100.00 |

Example 5.8: Spray

| | % b.w. |
|---|---|
| Caprylic Acid/Capric Acid Triglyceride | 4.00 |
| Ceteareth-12 | 1.50 |
| Caprylic Acid/Capric Acid Triglyceride | 2.00 |
| Mineral Oil | 5.00 |
| Octocrylene | 6.00 |
| Bis-Ethylhexyloxyphenol Methoxyphenyl Triazine (Tinosorb S) | 3.00 |
| Octyltriazone | 1.00 |
| Preservative | q.s. |
| Glycerol | 10.00 |
| micronized UV absorber of formula (7a), (7b) or (7d) | 2.30 |
| Phenylbenzimidazole Sulfonic Acid | 1.00 |
| NaOH 45% | 0.40 |
| Water | ad 100.00 |

Example 5.9: Spray

| | % b.w. |
|---|---|
| Glycerol Monostearate SE | 4.50 |
| Ceteareth-20 | 1.00 |
| Dicaprylyl Ether | 5.00 |
| Cetearyl Isononanoate | 5.00 |
| Dimethicone | 2.00 |
| Octocrylene | 8.00 |
| Bis-Ethylhexyloxyphenol Methoxyphenyl Triazine (Tinosorb S) | 4.00 |
| Preservative | q.s. |
| Glycerol | 5.00 |
| micronized UV absorber of formula (7a), (7b) or (7d) | 1.60 |
| Water | ad 100.00 |

6. Oil-free formulation only with liquid UV filters like Ethylhexyl-methoxycinnamate, Isoamyl methoxycinnamate, ethylhexyl Salicylate or octocrylene combined with 0.1% to 10% of micro-fine (particle size between 10 nm and 2 μm) naphthalene amidine imide compound

| Examples 6.1-6.5 | 6.1 | 6.2 | 6.3 | 6.4 | 6.5 |
|---|---|---|---|---|---|
| Stearic Acid | 0.3 | | | | |
| Isostearic Acid | | | | | 0.2 |
| Dilaureth-4 Phosphate | | 0.5 | 0.2 | 0.4 | 0.25 |
| Cetyl Phosphate | 0.1 | | 0.3 | | |
| Dimethicone | | 2.5 | | 2 | |
| Phenyl Trimethicone | 2 | | 3 | | |
| Caprylic Acid/Capric Acid Triglyceride | 5 | 5 | | 5 | 5 |
| $C_{12-15}$ Alkylbenzoate | | 5 | | 5 | |
| Dicaprylyl Ether | | 5 | 5 | | 1.0 |
| Butylene Glycol | | | 5 | | 2 |
| Dicaprylate/Dicaprate | | | | | |
| Mineral Oil | 4 | | | | |
| Vitamin E Acetate | 0.5 | 0.5 | 0.5 | 0.5 | 0.5 |
| Dioctyl Butamido Triazone | 1 | | 1 | | |
| Aniso Triazine | | | | 2 | 2 |
| Ethylhexyl Methoxycinnamate | 1 | | | 5 | 8 |
| Octyltriazone | | 2 | 1 | | c |
| 4-Methylbenzylidene Camphor | 2 | 4 | 2 | | |
| Butyl Methoxydibenzoylmethane | 1 | 2 | | | |
| micronized UV absorber of formula (7a), (7b) or (7d) | 1.50 | 0.18 | 3 | 2 | 1 |
| Titanium Dioxide | 2.5 | 1.0 | 2.0 | 1.5 | 3.0 |
| Preservative | 0.5 | 0.5 | 0.5 | 0.5 | 0.5 |

7. PPG-Caprylate-dicaprate combined with 0.1% to 10% of micro-fine (particle size between 10 nm and 2 μm) naphthalene amidine imide compound

| Examples 7.1-7.4: | Hydrodispersion | W/0-Pickering emulsion | Spray | Spray |
|---|---|---|---|---|
| Glyceemmonostearate | | | 4.00 | |
| Glycerinmonostearate SE | | | | 4.50 |
| Ceteareth-20 | | | | 1.00 |
| Ceteareth-12 | | | 1.50 | |
| Dimethicone | | | | 2.00 |
| Phenyl Trimethicone | | 5.00 | | |
| Vitamin E Acetate | | 0.50 | | |
| Dioctyl Butamido Triazone | 2.00 | 5.00 | | 2.00 |
| Aniso Triazine | 2;00 | 5.00 | 2.00 | 3.00 |
| Ethylhexyl Methoxycinnamate | | | 1 | |
| 4-Methylbenzylidene Camphor | | | | 1 |
| Octocrylene | | 10 | | 8 |
| Ethylhexyl Salicylate | 5 | 5 | | 2 |
| Ethylhexyl Methoxycinnamate | 8 | 10 | 5 | |
| Titanium Dioxideand Aluminaand Simethicone (Eusolex T2000) | | 4.00 | | |
| Aerosil R 972 | | 1.00 | | |
| Diethylhexyl 2,6-Naphthalate (Halbrite TQ) | 8.00 | 4.00 | 5.00 | 6.00 |
| Preservative | 0.50 | 0.50 | 0.50 | 0.50 |
| Glycerin | | 3.00 | 10.00 | 5.00 |
| micronized UV absorber of formula (7a), (7b) or (7d) | 0.80 | 2.50 | 1.50 | 1.00 |
| Xanthan Gum | 0.50 | | | |
| Acrylates/C10-30 Alkyl Acrylate Crosspolymer (Pemulen TR1) | 0.30 | | | |
| NaOH 45% | 0.30 | | 0.40 | |
| Water | ad 100.00 | ad 100.00 | ad 100.0 | ad 100.00 |

8. Lecithin combined with 0.1% to 10% of micro-fine (particle size between 10 nm and 2 μm) naphthalene amidine imide compound

|  | % b.w. |
|---|---|
| Example 8.1: O/W-Lotion | |
| Glycerylstearate SE | 3.50 |
| Stearic Acid | 1.80 |
| Glycerin | 3.00 |
| Celylstearylalcohol | 0.50 |
| Octyidodecanol | 7.00 |
| Dicaprylyl Ether | 8.00 |
| 4,4',4''-(1.3,5-Triazine-2,4,6-triyltriimino)-tris-benzoic acid tris(2-ethyl-hexylester) | 3.00 |
| Butyl Methoxydibenzoylmethane | 2.00 |
| Methylbenzylidencamphor | 1.04 |
| Titanium Dioxide | 2.00 |
| Mixed Iron Oxides | 1.00 |
| micronized UV absorber of formula (7a), (7b) or (7d) | 1.40 |
| Carbomer | 0.20 |
| NaOH 45% | 0.20 |
| Preservative | q.s. |
| Parfum | q.s. |
| Water, demin. | ad 100.00 |
| Example 8.2: Hydrodispersion gel | |
| Crosslinked Acrylic Acid/($C_{10-30}$) Alkyl Acrylate Copolymer | 0.50 |
| Ethanol | 3.50 |
| Glycerin | 3.00 |
| Dimethicone | 1.50 |
| Octyldodecanol | 0.50 |
| Caprylic Acid/Capric Acid Triglyceride | 5.00 |
| Iron mixed Oxide | 2.00 |
| 4,4',4''-(1.3,5-Triazine-2,4,6-triyltriimino)-tris-benzoic acid tris(2-ethyl-hexylester) | 5.00 |
| Carbomer | 0.20 |
| micronized UV absorber of formula (7a), (7b) or (7d) | 1.00 |
| NaOH (45%) | 0.55 |
| Preservative | q.s. |
| Perfume | q.s. |
| Water deionized | ad 100.00 |
| Example 8.3: Emulsifier-free Sunscreen Lotion SPF 30 | |
| Caprylic Acid/Capric Acid Triglyceride | 30.00 |
| 4,4',4''-(1.3,5-Triazine-2,4,6-triyltriimino)-tris-benzoic acid tris(2-ethylhexylester) | 4.00 |
| 4-Methylbenzylidene Camphor | 2.00 |
| Ethylhexyl Salicylate | 6.00 |
| Butyl Methoxydibenzoylmethane | 2.00 |
| Titanium Dioxideand Aluminaand Simethicone (Eusolex T2000) | 4.00 |
| Aerosil R 972 | 2.00 |
| Lecithin | 5.00 |
| micronized UV absorber of formula (7a), (7b) or (7d) | 1.80 |
| Stannous Oxide | 2.50 |
| Cetylhydroxyethylcellulose | 0.50 |
| Glycerin | 10.00 |
| Water | ad 100.00 |
| Example 8.4: O/W-Creme | |
| Glycerylstearate SE | 3.50 |
| Stearic Acid | 3.50 |
| Butyleneglycol | 5.00 |
| Cetylstearyl alcohol | 3.00 |
| $C_{12-15}$ Alkylbenzoate | 10.00 |
| Dioctyl Butamido Triazone | 4:00 |
| Aerosil | 3:00 |
| Lecithin | 2;00 |
| Carbomer | 0;20 |
| NaOH 45% | 0.35 |
| Preservative | q.s. |
| micronized UV absorber of formula (7a), (7b) or (7d) | 8.00 |
| Perfume | q.s. |
| Water, demin. | ad 100.00 |
| Example 8.5: O/W-Lotion | |
| Glycerylstearate SE | 3.50 |
| Stearic Acid | 1.80 |
| Glycerin | 3.00 |
| Celylstearylalcohol | 0.50 |
| Octyisodecanol | 7.00 |
| Dicaprylyl Ether | 8.00 |
| 4,4',4''-(1.3,5-Triazine-2,4,6-triyltriimino)-tris-benzoic acid tris(2-ethlhexylester) | 3.00 |
| Butyl Methoxydibenzoylmethane | 2.00 |
| 4-Methylbenzylidene Camphor | 1.00 |
| Titanium Dioxide | 2.00 |
| Mixed Iron Oxides | 1.00 |
| Carbomer | 0.20 |
| micronized UV absorber of formula (7a), (7b) or (7d) | 1.50 |
| NaOH 45% | 0.20 |
| Preservative | q.s. |
| Parfum | q.s. |
| Water, demin. | ad 100.00 |
| Example 8.6: Hydrodispersion Gel | |
| Acrylate/$C_{10-30}$-Alkyl Acrylate Crosspolymer | 0.50 |
| Ethanol | 3.50 |
| Glycerin | 3.00 |
| Dimethicone | 1.50 |
| Cetyldodecanol | 0.80 |
| Caprylic Acid/Capric Acid Triglyceride | 6.00 |
| Aerosil R 972 | 2.00 |
| Bis-Ethylhexyloxyphenol Methoxyphenyl Triazine (Tinosorb S) | 5.00 |
| Butyl Methoxydibenzoylmethane | 2.00 |
| micronized UV absorber of formula (7a), (7b) or (7d) | 1.90 |
| 4-Methylbenzylidene Camphor | 1.00 |
| Mixed Iron oxide; silanisated | 2.00 |
| Example 8.7: O/W Creme | |
| Glycerylstearate SE | 3.50 |
| Stearic Acid | 3.50 |
| Butylene Gglycol | 5.00 |
| Cetylstearylalcohol | 3.00 |
| $C_{12-15}$ Alkylbenzoate | 10.00 |
| Ethylhexyl Triazone | 4.00 |
| Butyl Methoxydibenzoylmethane | 2.00 |
| 4-Methylbenzylidene Camphor | 1.00 |
| Lecithin | 3.00 |
| micronized UV absorber of formula (7a), (7b) or (7d) | 2.80 |
| Carbomer | 0.20 |
| NaOH 45% | 0.35 |
| Preservative | q.s. |
| Perfume | q.s. |
| Water, demin. | ad 100.00 |
| Example 8.8: W/O-Lotion | |
| Polyglyceryl-2-Polyhydroxystearate | 3.50 |
| Polyglyceryl-3-Diisostearate | 3.50 |
| Butylene Glycol | 5.00 |
| Ceresin | 3.00 |
| $C_{12-15}$ Alkylbenzoate | 10.00 |
| Triazine | 4.00 |
| Lecithin | 2.00 |
| Butyl Methoxydibenzoylmethane | 2.00 |
| 4-Methylbenzylidene Camphor | 1.00 |
| Titanium Dioxide | 2.00 |
| micronized UV absorber of formula (7a), (7b) or (7d) | 1.30 |
| Vaseline | 2.00 |
| NaOH (45% ig) | 0.35 |
| Preservative | q.s. |
| Parfum | q.s. |
| Water | ad 100 |

9. Organosiloxane combined with 0.1% to 10% of micro-fine (particle size between 10 nm and 2 μm) naphthalene amidine imide compound

| Examples 9.1-9.6 | 9.1 OW 1 | 9.2 OW 2 | 9.3 OW 3 | 9.4 W/O 1 | 9.5 W/O 2 | 9.6 W/O 3 |
|---|---|---|---|---|---|---|
| Stearic Acid | 1.50 | 1.50 | | | | |
| Glycerin Monostearate | 3.00 | 3.00 | | | | |
| Sorbtan Stearate | | | 3.00 | | | |
| Polyglyceryl-3 Methylglucose Distearate | | | 1.50 | | | |
| Polyglyceryl-2 Dipolyhydroxystearate | | | | 5.00 | | |
| Cetyl Dimethicone Copolyol | | | | | | 5.00 |
| PEG-30 Dipolyhydroxystearate | | | | | 4.00 | |
| Dimethicone | | | | 2.00 | | 5.00 |
| Phenyl Trimethicone | 2.00 | 2.00 | | | 5.00 | 3.00 |
| Vitamin E-Acetate | 0.50 | 0.50 | 0.50 | | 0.50 | |
| Caprylic Acid/Capric Acid Triglyceride | 5.00 | 5.00 | | 5.00 | | |
| Mineral Oil | | | | 5.00 | 5.00 | |
| C$_{12-15}$ Alkylbenzoate | | 3.00 | 2.00 | | | |
| Butylene Glycol Dicaprylate/Dicaprate | | | 2.00 | | | |
| Dicaprylyl Ether | 3.00 | 3.00 | 5.00 | | | |
| Dioctyl Butamido Triazone | | 1.00 | | 3.00 | | |
| Aniso Triazine | 3.00 | 4.00 | 3.00 | 5.00 | 5.00 | 2.00 |
| Polysilicone-15 | 5.00 | 6.00 | 3.00 | 7.00 | 10.00 | 5.00 |
| Belsil SPG 128VP (Wacker) Glucoside modified silicone | 1.00 | 2.00 | 0.50 | 0.30 | 0.10 | 0.80 |
| Octyltriazone | | 1.00 | | 2.50 | | 1.00 |
| 4-Methylbenzylidene Camphor | | 2.00 | 4.00 | | | 4.00 |
| Octocrylene | | | 4.00 | 2.00 | | 5.00 |
| Ethylhexyl Salicylate | | | | 2.00 | | |
| Ethylhexyl Methoxycinnamate | | | 2 | 2 | | 5 |
| Titanium Dioxide | | 2 | | | 2 | |
| Aerosil R 972 | | | | | 0.50 | |
| Preservative | 0.50 | 0.50 | 0.50 | 0.50 | 0.50 | 0.50 |
| Glycerin | 3.00 | 10.00 | 10.00 | 5.00 | 10.00 | 5.00 |
| micronized UV absorber of formula (7a), (7b) or (7d) | 2.00 | 1.50 | 1.00 | 0.50 | 0.30 | 3.00 |
| Phenylbenzimidazole Sulfonic Acid | | | 3 | | | 3 |
| MgSO$_4$ | | | | 1.00 | 1.00 | |
| NaCl | | | | | | 1.00 |
| Xanthan Gum | 0.30 | 0.30 | | | | |
| Acrylates/C10-30 Alkyl Acrylate Crosspolymer (Pemulen TR1) | | | 0.10 | | | |
| NaOH 45% | 0.50 | 0.50 | 1.20 | | | 1.30 |
| Water | ad 100.00 | ad 100.00 | ad 100.00 | ad 100.00 | ad 100.00 | ad 100.00 |

| Examples 9.7-9.10 | 9.7 Hydro-dispersion | 9.8 W/0-Pickering-Emulsion | 9.9 Spray | 9.10 Spray |
|---|---|---|---|---|
| Glycerin Monostearate | | | 4.00 | |
| Glycerin Monostearate SE | | | | 4.50 |
| Ceteareth-20 | | | | 1.00 |
| Ceteareth-12 | | | 1.50 | |
| Dimethicone | | | | 2.00 |
| Phenyl Trimethicone | 1 | 5.00 | | |
| Vitamin E-Acetate | | 0.50 | | |
| Caprylic Acid/Capric Acid Triglyceride | 3 | | | |
| Mineral Oil | | | | |
| C$_{12-15}$ Alkylbenzoate | 2 | | | 2 |
| Butylene Glycol Dicaprylate/Dicaprate | | 5 | | |
| Dicaprylyl Ether | 2 | | | |
| Dioctyl Butamido Triazone | | 2 | | 2 |
| Aniso Triazine | 2.00 | 5.00 | 2.00 | 3.00 |
| Polysilicone-15 | 5 | 7 | 5 | 5 |
| Octyltriazone | | 1 | 1 | 1 |
| 4-Methylbenzylidene Camphor | | | | 1 |
| Butyl Methoxydibenzoylmethane | 1 | | | 2 |
| Octocrylene | | 5 | | |
| micronized UV absorber of formula (7a), (7b) or (7d) | 5 | 6 | 4 | 4 |
| Ethylhexylmethaxycinnamate | | 5 | 5 | |
| Titanium Dioxide and Alumina and Simethicone (Eusolex T2000) | | 4.00 | | |
| Aerosil R 972 | | 1.00 | | |
| Preservative | 0.50 | 0.50 | 0.50 | 0.50 |

-continued

| | | | | |
|---|---|---|---|---|
| Glycerin | 3.00 | 5.00 | 10.00 | 5.000 |
| Xanthan Gum | 0.50 | | | |
| Acrylates/C10-30 Alkyl Acrylate Crosspolymer (Pemulen TR1) | 0.30 | | | |
| NaOH 45% | 0.30 | | 0.40 | |
| Water | ad 100.00 | ad 100.0 | ad 100.0 | ad 100.0 |

10. Dialkylcarbonate combined with 0.1% to 10% of micro-fine (particle size between 10 nm and 2 μm) naphthalene amidine imide compound 11. Film-forming water soluble polymer combined with 0.1% to 10% of micro-fine (particle size between 10 nm and 2 μm) naphthalene amidine imide compound

| Examples 11.1-11.5: PIT - Sun Sprays | 11.1 | 11.2 | 11.3 | 11.4 | 11.5 |
|---|---|---|---|---|---|
| Glycerin Monostearate SE | 0.50 | | 3.00 | 2.00 | 4.00 |
| Ceteareth-12 | | 5.00 | | 1;00 | 1.50 |
| Ceteareth-20 | | | | 2.00 | |
| Ceteareth-30 | 5.00 | | 1.00 | | |
| Stearyl Alcohol | | | 3.00 | | 0.50 |
| Cetyl Alcohol | 2.50 | 1.00 | | 1.50 | |
| Ethylhexyl Methoxycinnamate | | | | 5.00 | 8.00 |
| Aniso Triazine | | 1.50 | | 2.00 | 2.50 |
| Butyl Methoxydibenzoylmethane | | | 2.00 | | |
| Dioctyl Butamido Triazone | 1.00 | 2.00 | | 2.00 | |
| Ethylhexyl Triazone | 4.00 | | 3.00 | 4.00 | |
| 4-Methylbenzylidene Camphor | | 4.00 | | | 2.00 |
| Octocrylene | | 4.00 | | | 2.50 |
| Bisimidazylate | | | 0.50 | | 1.50 |
| Phenylbenzmidazole Sulfonic Acid | 0.50 | | | 3.00 | |
| $C_{12-15}$ Alkylbenzoate | | 2.50 | | | 5.00 |
| Dicaprylyl Ether | | | 3.50 | | |
| Butylene Glycol Dicaprylate/Dicaprate | 5.00 | | | 6.00 | |
| Dicaprylyl Carbonate | | | 6.00 | | 2.00 |
| Dimethicone | | 0.50 | 1.00 | | |
| Phenyl Trimethicone | 2.00 | | | 0.50 | 0.50 |
| Shea Butter | | 2.00 | | | 0.50 |
| PVP Hexadecene Copolymer | 0.50 | | | 0.50 | 1.00 |
| Glycerin | 3.00 | 7.50 | 5.00 | 7.50 | 2.50 |
| micronized UV absorber of formula (7a), (7b) or (7d) | 2.00 | 1.30 | 2.50 | 3.50 | 0.30 |
| Vitamin E Acetate | 0.50 | | 0.25 | | 1.00 |
| Polyurethane | 0.20 | 0.50 | 1.50 | 0.50 | 0.40 |
| DMDM Hydantoin | 0.60 | | 0.40 | 0.20 | |
| Konkaben LMBO | | 0.20 | | | 0.15 |
| Methylparaben | | 0.50 | 0.26 | 0.15 | |
| Phenoxyethanol | 0.50 | 0.40 | | 1.00 | 0.60 |
| Ethanol | 3.00 | 2.00 | 1.50 | | 1.00 |
| Water | ad 100 | ad 100 | ad 100 | ad 100 | ad 100 |

| Example 11.6-11.12: O/W Sunscreen Emulsion | 11.6 | 11.7 | 11.8 | 11.9 | 11.10 | 11.11 | 11.12 |
|---|---|---|---|---|---|---|---|
| Glycerin Monostearate SE | 0.50 | 1.00 | 3.00 | | | 1.50 | |
| Glyceryl Stearate Citrate | 2.00 | | | 1:00 | 2.00 | | 2.50 |
| Stearic Acid | | 3.00 | | 2.00 | | | |
| PEG-40 Stearate | 0.50 | | | | | 2.00 | |
| Cetyl Phosphate | | | | | 1.00 | | |
| Stearyl Alkohol | | | 3.00 | | | 2.00 | 0.50 |
| Cetyl Alkohol | 2.50 | 1.00 | | 1.50 | 0.50 | | 2.00 |
| Ethylhexyl Methoxycinnamate | | | | 5.00 | 6.00 | | 8.00 |
| Aniso Triazine | | 1.50 | | 2.00 | 2.50 | | 2.50 |
| Butyl Methoxydibenzoyl-methane | 1.00 | | 2.00 | | | 2.00 | |
| Dioctyl Butamido Triazone | | 2.00 | | 2.00 | | 2.00 | |
| Ethylhexyl Triazone | 4.00 | | 3.00 | 4.00 | 4.00 | 2.00 | |
| 4-Methylbenzylidene Camphor | 4.00 | 4.00 | | | 2.00 | 4.00 | 2.00 |
| Octocrylene | | 4.00 | | | | | 2.50 |
| Dioctyl Butamido Triazone | 1.00 | | | 2.00 | 1.00 | | |
| Bisimidazylate | 1.00 | | 0.50 | | | 1.00 | 1.50 |
| Phenylbenzmidazole Sulfonic Acid | 0:50 | | | 3.00 | | | |
| Titanium Dioxide | 1.00 | 1.50 | | 3.00 | 2.00 | | 2.00 |

-continued

| | | | | | | | |
|---|---|---|---|---|---|---|---|
| $C_{12-15}$ Alkylbenzoate | | 2.50 | | | 4.00 | 7.00 | 5.00 |
| Dicaprylyl Ether | | | 3.50 | | 2.00 | | |
| Butylene Glycol Dicaprylate/Dicaprate | 5.00 | | | 6.00 | | | |
| Dicaprylyl Carbonate | | | 6.00 | | | 2.00 | 2.00 |
| Dimethicone | | 0.50 | 1.00 | | 2.00 | | |
| Cetyl Dimethicone | 2.00 | | | 0;50 | | | 0.50 |
| Shea Butter | | 2.00 | | | | | 0.50 |
| PVP Hexadecene Copolymer | 0.50 | | | 0.50 | 1.00 | | 1.00 |
| Xanthan Gum | 3;00 | 7.50 | | 7.50 | 5.00 | | 2.50 |
| micronized UV absorber of formula (7a), (7b) or (7d) | 0.80 | 1.50 | 0.30 | 0.90 | 2.50 | 2.80 | 3.20 |
| Sodium Carbomer | | 0.20 | 0.10 | 0.20 | | | |
| Vitamin E Acetate | 0.50 | | 0.25 | | 0.75 | | 1.00 |
| Polyurethane | 0.50 | 0.20 | 1.50 | 0.50 | 0.60 | 1.00 | 0.40 |
| DMDM Hydantoin | | 0.60 | 0.40 | 0.20 | | | |
| Konkaben LM B 6 | | | | 0.18 | 0.20 | 0.10 | 0.15 |
| Methylparaben | 0.25 | | 0.26 | | 0.50 | | |
| Phenoxyethanol | 1.00 | 0.40 | | 0.40 | 0.60 | 0.40 | 0.60 |
| Ethanol | | 2.00 | 1.50 | | 3.00 | | 1.00 |
| Water | ad.100 | ad.100 | ad. 100 | ad 100 | ad 100 | ad 100 | ad 100 |

| Example 11.13-11.17: Hydrodispersions | 11.13 | 11.14 | 11.15 | 11.16 | 11.17 |
|---|---|---|---|---|---|
| Ceteareth 20 | 1.00 | | | 0.5 | |
| Celyl Alkohol | | | 1.00 | | |
| Sodium Carbomer | | 0.20 | | 0.30 | |
| Acrylates/C10-30 Alkyl Acrylate Crosspolymer | 0.50 | | 0..40 | 0.10 | 0.10 |
| Xanthan Gum | | 0;30 | 0.15 | | 0.50 |
| Ethylhexyl Methoxycinnamate | | | | 5.00 | 8.00 |
| Aniso Triazine | | 1;50 | | 2.00 | 2.50 |
| Butyl Methoxydibenzoylmethane | 1;00 | | 2.00 | | |
| Dioctyl Butamido Triazone | | 2;00 | | 2.00 | 1.00 |
| Ethylhexyl Triazone | 4.00 | | 3.00 | 4.00 | |
| 4-Methylbenzylidene Camphor | 4.00 | 4.00 | | | 2.00 |
| Octocrylene | | 4.00 | 4.00 | | 2.50 |
| micronized UV absorber of formula (7a), (7b) or (7d) | 1.00 | | 1.50 | 3.00 | 4.50 |
| Dioctyl Butamido Triazone | 1.00 | | | 2.00 | |
| Bisimidazylate | 1.00 | | 0.50 | | 2.00 |
| Phenylbenzmidazole Sulfonic Acid | 0.50 | | | 3.00 | |
| Titanium Dioxide | 0.50 | | 2.00 | 3.00 | 1.00 |
| $C_{12-15}$ Alkylbenzoate | 2.00 | 2.50 | | | |
| Dicaprylyl Ether | | 4.00 | | | |
| Butylene Glycol Dicaprylate/Dicaprate | 4.00 | | 2:00 | 6.00 | |
| Dicaprylyl Carbonate | | 2.00 | 6:00 | | |
| Dimethicone | | 0:50 | 1;00 | | |
| Phenyltrimethicone | 2.00 | | | 0.50 | 2.00 |
| Shea Butter | | 2.00 | | | |
| PVP Hexadecene Copolymer | 0:50 | | | 0.50 | 1.00 |
| Octoxyglycerin | | | 1:04 | | 0.50 |
| Glycerin | 3.00 | 7.50 | | 7.50 | 2.50 |
| *Glycine Soja* | | | 1.50 | | |
| Vitamin E Acetate | 0;50 | | 0.25 | | 1.00 |
| Polyurethane | 0.15 | 0.60 | 1.50 | 1.00 | 0.80 |
| DEDM Hydantoin | | 0.60 | 0;40 | 0.20 | |
| Konkaben LM B db | 0:20 | | | | 0.15 |
| Methylparben | 0;50 | | 0.25 | 0.15 | |
| Phenoxyethanal | 0.50 | 0.40 | | 1.00 | 0.60 |
| Ethanol | 3.00 | 2.00 | 1.50 | | 1.00 |
| Water | ad. 100 | ad. 100 | ad. 100 | ad. 100 | ad. 100 |

| Example 11.18-11.24: O/W Sunscreen Emulsions | 11.18 | 11.19 | 11.20 | 11.21 | 11.22 | 11.23 | 11.24 |
|---|---|---|---|---|---|---|---|
| Glycerin Monostearate SE | 0.50 | 1.00 | 3.00 | | | 1.50 | |
| Glyceryl Stearate Citrate | 2.00 | | | 1:00 | 2.00 | | 2.50 |
| Stearic Acid | | 3.00 | | 2.00 | | | |
| PEG-40 Stearate | 0.50 | | | | | 2.00 | |
| Cetyl Phosphate | | | | | 1.00 | | |
| Stearyl Alcohol | | | 3.00 | | | 2.00 | 0.50 |
| Cetyl Alcohol | 2.50 | 1.00 | | 1.50 | 0.50 | | 2.00 |
| Ethylhexyl Methoxycinnamate | | | | 5.00 | 6.00 | | 8.00 |
| Aniso Triazine | | 1.50 | | 2.00 | 2.50 | | 2.50 |
| Butyl Methoxydibenzoyl-methane | 1.00 | | 2.00 | | | 2.00 | |
| Dioctyl Butamido Triazone | | 2.00 | | 2.00 | | | 2.00 |

-continued

| | | | | | | | |
|---|---|---|---|---|---|---|---|
| micronized UV absorber of formula (7a), (7b) or (7d) | 1.00 | 2.30 | 1.50 | 2.50 | 2.80 | 3.50 | 6.00 |
| Ethylhexyl Triazone | 4.00 | | 3.00 | 4.00 | 4.00 | 2.00 | |
| 4-Melhylbenrylidene Camphor | 4.00 | 4.00 | | | 2.00 | 4.00 | 2.00 |
| Octocrylene | | 4.00 | | | | | 2.50 |
| Dioctyl Butamido Triazone | 1.00 | | | 2.00 | 1.00 | | |
| Bisimidazylale | 1.00 | | 0.50 | | | 1.00 | 1.50 |
| Phenylbenzmidazole Sulfonic Acid | 0.50 | | | 3.00 | | | |
| Titanium Dioxide | 1.00 | 1.50 | | 3.00 | 2.00 | 2.00 | |
| C$_{12-15}$ Alkylbenzoate | | 2.50 | | | 4.00 | 7.00 | 5.00 |
| Dicaprylyl Ether | | | 3.50 | | 2.00 | | |
| Butylene Glycol Dicaprylate/Dicaprate | 5.00 | | | 6.00 | | | |
| Dicaprylyl Carbonate | | | 6.00 | | | 2.00 | 2.00 |
| Dimethicone | | 0.50 | 1.00 | | 2.00 | | |
| Cetyl Dimethicone | 2.00 | | | 0.50 | | | 0.50 |
| Shea Butter | | 2.00 | | | | | 0.50 |
| PVP Hexadecene Copolymer | 0.50 | | | 0.50 | 1.00 | | 1.00 |
| Glycerin | 3.00 | 7.50 | | 7.50 | 5.00 | | 2.50 |
| micronized UV absorber of formula (7a), (7b) or (7d) | 2.00 | 1.00 | 5.00 | 2.00 | 1.50 | 0.80 | 0.60 |
| Xanthan Gum | 0.15 | | 0.05 | | | | 0.30 |
| Sodium Carbomer | | 0.20 | 0.10 | 0.20 | | | |
| Vitamin E Acetate | 0.50 | | 0.25 | | 0.75 | | 1.00 |
| Polyurethane | 0.50 | 0.20 | 1.50 | 0.50 | 0.60 | 1.00 | 0.40 |
| DEDM Hydantoin | | 0.60 | 0.40 | 0.20 | | | |
| Konkaben LMB | | | | 0.18 | 0.20 | 0.10 | 0.15 |
| Methylparaben | 0.15 | | 0.25 | | 0.50 | | |
| Phenoxyethanol | 1.00 | 0.40 | | 0.40 | 0.60 | 0.40 | 0.60 |
| Ethanol | | 2.00 | 1.50 | | 3.00 | | 1.00 |
| Water | ad 100 | ad 100 | ad 100 | ad 100 | ad 100 | ad 100 | ad 100 |

| Examples 11.25-11.29: W/O Sunscreen | 11.25 | 11.26 | 11.27 | 11.28 | 11.29 |
|---|---|---|---|---|---|
| Cetyldimethicone Copolyol | | 2.50 | | 4.00 | |
| Polyglyceryl-2 Dipolyhydroxystearate | 5.00 | | | | 4.50 |
| PEG-30 Dipolyhydroxystearate | | | 5.00 | | |
| Ethylhexyl Methoxycinnamate | | 5.00 | | 5.00 | 4.40 |
| Aniso Triazine | 2.00 | 2.50 | | 2.00 | 2.50 |
| Butyl Methoxydibenzoylmethane | | | 2.00 | 1.00 | |
| Dioctyl Butamido Triazone | 3.00 | 1.00 | | | 3.00 |
| Ethylhexyl Triazone | | | 3.00 | 4.00 | |
| 4-Methylbenzylidene Camphor | | 2.00 | | 4.00 | 2.00 |
| Octocrylene | 7.00 | 2.50 | 4.00 | | 2.50 |
| micronized UV absorber of formula (7a), (7b) or (7d) | 7.50 | 2.50 | 1.50 | 1.30 | 4.50 |
| Dioctyl Butamido Triazone | 1.00 | | | 2.00 | |
| Bisimidazylate | 1.00 | 2.00 | 0.50 | | |
| Phenylbenzmidazole Sulfonic Acid | 0.50 | | | 3.00 | 2.00 |
| Titanium Dioxide | | 2.00 | 1.50 | | 1.00 |
| Mineral Oil | | | 10.0 | | 5.00 |
| C$_{12-15}$ Alkylbenzoate | | | | 9.00 | |
| Dicaprylyl Ether | 10.00 | | | | 7.00 |
| Butylene Glycol Dicaprylate/Dicaprate | | | 2.00 | 8.00 | 4.00 |
| Dicaprylyl Carbonate | 5.00 | | 6.00 | | |
| Dimethicone | | 4.00 | 1.00 | 5.00 | |
| Cyclomethicone | 2.00 | 25.00 | | | 2.00 |
| Shea Butter | | | 3.00 | | |
| PVP Hexadecene Copolymer | 0.50 | | | 0.50 | 1.00 |
| Octoxyclycerin | | 0.30 | 1.00 | | 0.50 |
| Glycerin | 3.00 | 7.50 | | 7.50 | 2.50 |
| Glycerin Soya | | 1.00 | 1.50 | | |
| MgSO$_4$ | 1.00 | 0.50 | | 0.5 | |
| MgCl$_2$ | | | 1.00 | | 0.70 |
| Vitamine E Acetate | 0.50 | | 0.25 | | 1.00 |
| micronized UV absorber of formula (7a), (7b) or (7d) | 1.00 | 1.50 | 0.50 | 0.30 | 2.00 |
| Polyurethane | 0.10 | 0.60 | 1.50 | 1.00 | 0.80 |
| DMDM Hydantoin | | 0.60 | 0.40 | 0.20 | |
| Methylparaben | | 0.50 | | 0.25 | 0.15 |
| Phenoxyethanol | | 0.50 | 0.40 | | 1.00 | 0.60 |
| Ethanol | | 3.00 | | 1.50 | 1.00 |
| Water | ad 100 | ad 100 | ad 100 | ad 100 | ad 100 |

12. Saccharoseester combined with 0.1% to 10% of microfine (particle size between 10 nm and 2 μm) naphthalene amidine imide compound

| Examples 12.1-12.7 | 12.1 | 12.2 | 12.3 | 12.4 | 12.5 | 12.8 | 12.7 |
|---|---|---|---|---|---|---|---|
| Sucrose Distearate | 3 | 2.5 | 1.5 | 2 | 3 | 1.5 | 2 |
| Stearyl Alcohol | 2 | | 1 | | 1 | | |
| Cetearyl Alcohol | | | | 3 | | | 4.5 |
| Cetyl Alcohol | 2 | 2.5 | | | | 0.5 | |
| Hydrogenated Cocoglycerides | 1 | 2 | | 3 | 1 | 2 | |
| Shea Butter | 1 | | 1 | | | | |
| C18-36 Triglyceride | | 0.5 | | | | 1.0 | |
| $C_{12-15}$ Alkylbenzoate | 2 | | | 2 | 2 | | |
| Butylene Glycol Dicaprylate/Dicaprate | 5 | 2 | | | 6 | | 5 |
| Dicaprylyl Ether | | 2 | | | | 3 | |
| Dicaprylyl Carbonate | 2 | | | 3 | | 2 | |
| Caprylic Acid/Capric Acid Triglyceride | | 1 | | 1.5 | | | 1.5 |
| Octyldodecanol | | | | 2 | | | |
| Mineral Oil | 2 | | | | | 2 | |
| Cyclomethicone | | | 2 | | | | |
| Dimethicone | 2 | | | | | 2 | 1 |
| Phenyl Trimethicone | | | | 2 | | | 1 |
| Bis-Ethylhexyloxyphenol Methoxyphenyl Triazine (Tinosorb S) | | | | | 1.5 | 2 | |
| Butyl Methoxydibenzoyl-methane | | | | 1.5 | | | 2 |
| micronized UV absorber of formula (7a), (7b) or (7d) | 0.50 | 0.80 | 2.50 | 1.20 | 5.60 | 4.00 | 3.00 |
| Bisimidazylate | 0.5 | 2 | 1 | 0.5 | 2 | 0.5 | 0.5 |
| Octocrylene | | | | | 5 | 10 | |
| Ethyl Salicylate | | | | | 1 | | |
| Ethylhexyl Methoxycinnamate | | | 5 | 7.5 | 5 | | |
| Homosalate | | | 1 | | | | |
| Dioctyl Butamido Triazone | 2 | 1 | 1 | | 1 | 3 | 2 |
| 4-Methylbenzylidene Camphor | 2 | 3 | 2 | | 2 | | 2 |
| Phenylbenzimidazole Sulfonic Acid | | 1 | | | | | |
| Bisoctyltriazol | | 1 | | 2 | 4 | | |
| Titanium Dioxide | 2 | | 1 | 3 | | 2 | 1 |
| Stannous Oxide | | 1 | | 0.5 | | | |
| Trisodium EDTA | 1 | 1 | | 1 | 1 | 1 | 1 |
| PVP/Hexadecene | 1 | | | 0.5 | | 0.5 | |
| Tricontayl PVP | | 0.5 | 0.5 | | 1 | | 1 |
| Polyurethane | 1 | | | 1 | 1 | | |
| Tocopheryl Acetate | 0.5 | 0.5 | | 0.5 | | 1 | 0.5 |
| α-Glucosylrutin + Isoquercitrin | | 0.5 | 0.2 | | | 0.5 | |
| Phenoxyethanol | 0.1 | 0.5 | 0.5 | | 0.5 | | 0.5 |
| Paraben | 0.6 | | | | | | |
| Xanthan Gum | 0.2 | | | 0.5 | 0.2 | 0.15 | |
| Carbomer | | 0.2 | | | 0.1 | 0.3 | 0.3 |
| Alkyl Acryllates Copolymer | | | 0.1 | | | | |
| Cellulose Ether | | | 0.2 | 0.5 | | | |
| Iodopropynyl Butylcarbamate | 0.05 | 0.15 | | 0.2 | | | 0.1 |
| NaOH 45% | 0.3 | 0.5 | 0.5 | | 0.5 | 0.5 | 0.25 |
| Glycerin | 5 | 7.5 | 2.5 | | 5 | | 2 |
| Butylene Glycol | | | 5 | 7.5 | | 3 | 3 |
| Octoxyglycerin | 0.5 | 0.4 | | | | | |
| DMDM Hydantoin | | | 0.5 | | 0.6 | 0.4 | 0.05 |
| Alcohol denat. | | 1 | | 2.5 | 2 | | 3 |
| Colour (water- and/or oil-soluble) | 0.2 | | | | 0.05 | | |
| Distarch Phosphate | | 0.5 | | | | | 5 |
| Parfum | q.s. | q.s. | q.s. | q.s. | q.s. | q.s. | q.s. |
| Water | ad 100 | ad 100 | ad 100 | ad 100 | ad 100 | ad 100 | ad 100 |

13. $C_6$-$C_{24}$-dialkylmaleate combined with 0.1% to 10% of micro-fine (particle size between 10 nm and 2 μm) naphthalene amidine imide compound Example 13.1

| | % b.w. |
|---|---|
| Glycerylstearate | 3.50 |
| Stearic Acid | 1.80 |
| Glycerin | 3.00 |
| Cetylstearyl Alcohol | 0.50 |
| NaOH 45% | 0.20 |
| Octyldodecanol | 7.00 |
| Dicaprylyl Ether | 8.00 |
| Ethylhexyl Triazone | 3.00 |
| micronized UV absorber of formula (7a), (7b) or (7d) | 2.50 |
| Dioctylmaleate | 6.00 |
| Carbomer | 0.20 |
| Preservative | q.s. |
| Parfum | q.s. |
| Water demin. | ad 100 |

Example 13.2: Hydrodispersion Gel

| | % b.w. |
|---|---|
| Crosslinked Acrylic Acid/($C_{10-30}$) Alkyl Acrylate Copolymer | 0.50 |
| Ethanol | 3.50 |
| Glycerin | 3.00 |
| Dimethicone | 1.50 |
| NaOH 45% | 0.55 |
| Octyldodecanol | 0.50 |
| Caprylic Acid/Capric Acid Triglyceride | 5.0 |
| Dioctylmaleate | 5.0 |
| micronized UV absorber of formula (7a), (7b) or (7d) | 4.0 |
| Ethylhexyl Triazone | 5.0 |
| Carbomer | 0.2 |
| Preservative, Parfum | q.s. |
| Water demin. | ad 100 |

Example 13.3: O/W Cream

| | % b.w. |
|---|---|
| Glycerinstearate | 3.50 |
| Stearic Acid | 3.50 |
| Butyleneglycol | 5.00 |
| Cetylstearyl Alcohol | 3.00 |
| micronized UV absorber of formula (7a), (7b) or (7d) | 1.50 |
| NaOH 45% | 0.35 |
| $C_{12-15}$ Alkylbenzoate | 10.0 |
| Octocrylene | 4.0 |
| Ethylhexyl Triazone | 4.0 |
| Dioctylmaleate | 6.0 |
| Carbomer | 0.20 |
| Preservatives | q.s. |
| Parfum | q.s. |
| Water demin. | ad 100 |

Example 13.4: W/O Lotion

| | % b.w. |
|---|---|
| Polyglyceryl-2-Polyhydroxystearate | 3.50 |
| Polyglyceryl-3-Diisostearate | 3.50 |
| Butylene Glycol | 5.00 |
| Ceresin | 3.00 |
| NaOH 45% | 4.5 |
| Alkylbenzoate | 10.00 |
| Ethylhexyl Triazone | 4.0 |
| micronized UV absorber of formula (7a), (7b) or (7d) | 1.50 |
| Phenylbenzimidazole Sulfonic Acid (Eusolex 232) | 2.0 |
| Dioctylmaleate | 6.0 |
| Vaseline | 2.0 |
| Preservatives | q.s. |
| Parfum | q.s. |
| Water demin. | ad 100 |

Example 13.5: O/W Lotion

| | % b.w. |
|---|---|
| Glycerin Sstearate | 3.50 |
| Stearic Acid | 1.80 |
| Cetylstearyl Alcohol | 0.50 |
| NaOH 45% | 0.20 |
| Octyldodecanol | 7.0 |
| Dicaprylyl Ether | 8.0 |
| SMT | 3.00 |
| Titanium Dioxide | 2.00 |
| micronized UV absorber of formula (7a), (7b) or (7d) | 2.60 |
| Butyl Methoxydibenzoylmethane | 2.00 |
| 4-Methylbenzylidene Camphor | 1.00 |
| Dioctylmaleate | 6.00 |
| Carbomer | 0.20 |
| Preservatives | q.s. |
| Parfum | q.s. |
| Water | ad 100 |

Example 13.6: O/W Creme

| | % b.w. |
|---|---|
| Glyceryl Stearate | 3.50 |
| Stearic Acid | 3.5 |
| Butylene Glycol | 5.0 |
| Cetylstearylalcohol | 3.00 |
| micronized UV absorber of formula (7a), (7b) or (7d) | 2.00 |
| NaOH 45% | 0.15 |
| $C_{12-15}$ Alkylbenzoate | 10.0 |
| Ethylhexyl Triazone | 4.0 |
| Octocrylene | 10.0 |
| Titanium Dioxide | 2.00 |
| Butyl Methoxydibenzoylmethane | 2.0 |
| 4-Methylbenzylidene Camphor | 1.0 |
| Dioctylmaleate | 6.00 |
| Carbomer | 0.20 |
| Preservatives | q.s. |
| Parfum | q.s. |
| Water | ad 100 |

Example 13.7: W/O Lotion

| | % b.w. |
|---|---|
| Polyglyceryl-2-Polyhydroxystearate | 3.50 |
| Polyglyceryl-3-Diisostearate | 3.50 |
| Butylene Glycol | 5.00 |
| Ceresin | 3.00 |
| NaOH 45% | 0.35 |
| $C_{12-15}$ Alkylbenzoate | 10.0 |
| Ethylhexyl Triazone | 4.00 |
| Titanium Dioxide | 2.00 |
| Butyl Methoxydibenzoylmethane | 2.00 |
| 4-Methylbenzylidene Camphor | 1.00 |
| micronized UV absorber of formula (7a), (7b) or (7d) | 1.50 |
| Dioctylmaleate | 6.00 |
| Vaseline | 2.00 |
| Preservatives | q.s. |
| Parfum | q.s. |
| Water | ad 100 |

Example 13.8: O/W Lotion

| | % b.w. |
|---|---|
| Glyceryl Stearate | 3.50 |
| Stearic Acid | 1.80 |
| Glycerin | 3.00 |
| Cetylstearyl Alcohol | 0.50 |
| NaOH 45% | 0.20 |
| Octyldodecanol | 7.00 |
| Dicaprylyl Ether | 8.00 |
| micronized UV absorber of formula (7a), (7b) or (7d) | 4.50 |
| ETT | 3.00 |
| Dioctylmaleate | 6.00 |
| Carbomer | 0.20 |
| Preservatives | q.s. |
| Parfum | q.s. |
| Water | ad 100 |

Example 13.9: Hydrodispesion Gel

| | % b.w. |
|---|---|
| Crosslinked Acrylic Acid/($C_{10-30}$) Alkyl Acrylate Copolymer | 0.50 |
| Ethanol | 3.50 |
| Glycerin | 3.00 |
| Dimethicone | 1.50 |
| NaOH 45% | 0.55 |
| Octyldodecanol | 0.50 |
| Caprylic Acid/Capric Acid Triglyceride | 5.00 |
| Dioctylmaleate | 5.00 |
| micronized UV absorber of formula (7a), (7b) or (7d) | 6.50 |
| ETT | 5.00 |
| Carbomer | 0.20 |
| Preservatives | q.s. |
| Parfum | q.s. |
| Water demin. | ad 100 |

14. FeTiOx having a Fe-content of 0 to 50% combined with 0.1% to 10% of micro-fine (particle size between 10 nm and 2 μm) naphthalene amidine imide compound
15. Alkyl carboxylic acid combined with 0.1% to 10% of micro-fine (particle size between 10 nm and 2 μm) naphthalene amidine imide compound
16. Boron nitride (improving of skin sensitivity) combined with 0.1% to 10% of micro-fine (particle size between 10 nm and 2 μm) naphthalene amidine imide compound

| | % b.w. |
|---|---|
| Example 16.1: | |
| Stearic Acid | 1.50 |
| Glycerin Monostearate | 3.50 |
| Bis-Ethylhexyloxyphenol Methoxyphenyl Triazine (Tinosorb S) | 10.00 |
| $C_{12-15}$ Alkylbenzoate | 5.00 |
| Butylene Glycol Dicaprylate/Dicaprate | 5.00 |
| Caprylic Acid/Capric Acid Triglyceride | 5.00 |
| Cetylstearyl Alcohol | 0.50 |
| Preservatives, Dyes | q.s. |
| NaOH 45% | 0.20 |
| Carbomer | 3.00 |
| Glycerin | 3.00 |
| micronized UV absorber of formula (7a), (7b) or (7d) | 1.00 |
| EDTA Solution | 1.00 |
| Water | ad 100 |
| Example 16.2: | |
| Stearic Acid | 1.50 |
| Glycerin Monostearate | 3.50 |
| Bis-Ethylhexyloxyphenol Methoxyphenyl Triazine (Tinosorb S) | 10.00 |
| $C_{12-15}$ Alkylbenzoate | 5.00 |
| Octyldodecanol | 5.00 |
| Cetylstearylalcohol | 1.00 |
| Preservatives, Dyes | q.s. |
| NaOH 45% | 0.20 |
| Carbomer | 3.00 |
| Glycerin | 3.00 |
| micronized UV absorber of formula (7a), (7b) or (7d) | 3.50 |
| EDTA Solution | 1.00 |
| Water | ad 100 |
| Example 16.3: | |
| Stearic Acid | 1.50 |
| Glycerin Monostearate | 0.50 |
| Bis-Ethylhexyloxyphenol Methoxyphenyl Triazine (Tinosorb S) | 4.00 |
| Butylene Glycol Dicaprylate/Dicaprate | 5.0 |
| Stearyl Heptanoate/Caprylate | 2.00 |
| Silicon Oil | 5.00 |
| Isohexadecane | 2.00 |
| 4,4',4''-(1.3,5-Triazine-2,4,6-triyltriimino)-tris-benzoic acid tris(2-ethylhexylester) | 1.0 |
| 4-Methylbenzylidene Camphor | 4.00 |
| Butyl Methoxydibenzoylmethane | 2.00 |
| Cetyl Stearyl Alcohol | 0.50 |
| Vitamine E Acetate | 0.50 |
| Preservatives, Dyes | q.s. |
| NaOH 45% | 0.20 |
| Carbomer | 3.00 |
| Glycerin | 3.00 |
| micronized UV absorber of formula (7a), (7b) or (7d) | 5.80 |
| EDTA Solution | 1.00 |
| Water | ad 100 |
| Example 16.4: | |
| Stearic Acid | 1.50 |
| Glycerin Monostearate | 2.00 |
| Bis-Ethylhexyloxyphenol Methoxyphenyl Triazine (Tinosorb S) | 40.00 |
| Butylene Glycol Dicaprylate/Dicaprate | 3.00 |
| Caprylic Acid/Capric Acid Triglyceride | 3.00 |
| Octyldodecanol | 3.00 |
| Silicon Oil | 1.00 |
| 4,4',4''-(1.3,5-Triazine-2,4,6-triyltriimino)-tris-benzoic acid tris(2-ethylhexylester) | 2.00 |
| Titanium Dioxide | 2.00 |
| micronized UV absorber of formula (7a), (7b) or (7d) | 2.00 |

-continued

| | % b.w. |
|---|---|
| Cetyl Stearyl Alcohol | 1.00 |
| Vitamine E Acetate | 0.50 |
| Preservatives, Dyes | q.s. |
| NaOH 45% | 0.20 |
| Carbomer | 3.00 |
| Glycerin | 5.00 |
| EDTA Solution | 1.00 |
| Water | ad 100 |
| Example 16.5: | |
| Stearic Acid | 1.00 |
| Glycerin Monostearate | 3.00 |
| Bis-Ethylhexyloxyphenol Methoxyphenyl Triazine (Tinosorb S) | 2.00 |
| Alkyl Bbenzoate | 5.00 |
| But glycol Dicaprylate/dicaprate | 5.00 |
| Silicon Oil | 1.00 |
| 4,4',4''-(1.3,5-Triazine-2,4,6-triyltriimino)-tris-benzoic acid tris(2-ethylhexylester) | 2.00 |
| 4-Methylbenzylidene Camphor | 4.00 |
| Titanium Dioxide | 2.00 |
| Cetyl stearyl Alcohol | 0.50 |
| Vitamine E Acetate | 0.50 |
| Preservatives | 0.50 |
| NaOH 45% | 0.20 |
| Carbomer | 0.20 |
| Glycerin | 7.00 |
| micronized UV absorber of formula (7a), (7b) or (7d) | 2.00 |
| EDTA Solution | 1.00 |
| Water | ad 100 |

17. Amide oils as insect repellents combined with 0.1% to 10% of micro-fine (particle size between 10 nm and 2 μm) naphthalene amidine imide compound

| | % b.w. |
|---|---|
| Example 17.1: O/W Emulsion | |
| Stearic Acid | 1.50 |
| Glycerin Monostearate | 3.00 |
| Dimethicone | 2.00 |
| Vitamine E Acetate | 0.50 |
| Aniso Triazine | 4.00 |
| Repellent 3535 | 10.00 |
| Glycerin | 3.00 |
| Xanthan Gum | 0.30 |
| NaOH 45% | 0.50 |
| micronized UV absorber of formula (7a), (7b) or (7d) | |
| Preservatives, Parfum, Dyes | q.s. |
| Water | ad 100 |
| Example 17.2: O/W Emulsion | |
| Stearic Acid | 1.50 |
| Glycerin Monostearate | 3.00 |
| Caprylic Acid/Capric Acid Triglyceride | 5.0 |
| Dicaprylyl Ether | 5.0 |
| Dimethicone | 1.00 |
| Butylene Glycol Dicprylate/dicaprate | 2.00 |
| $C_{12-15}$ Alkylbenzoate | 3.00 |
| Vitamine E Acetate | 0.50 |
| Dioctyl Butamido Triazone | 2.0 |
| Aniso Triazine | 2.00 |
| Repellent 3535 | 5.00 |
| Octyl Triazone | 1.00 |
| 4-Methylbenzylidene Camphor | 4.00 |
| Butyl Methoxy dibenzoylmethane | 2.00 |
| Titanium Dioxide | 1.00 |
| Glycerin | 5.00 |
| micronized UV absorber of formula (7a), (7b) or (7d) | 3.50 |
| Crosslinked Acrylic Acid/($C_{10-30}$) Alkyl Acrylate Copolymer | 0.20 |
| NaOH 45% | 0.7 |
| Preservatives, Parfum, Dyes | q.s. |
| Water | ad 100 |

Example 17.3: O/W Emulsion

| | % b.w. |
|---|---|
| Polyglyceryl-2 Dipolyhydroxystearate | 5.0 |
| Dimethicone | 2.0 |
| Mineral Oil | 5.0 |
| Isohexadecane | 5.0 |
| Butylene Glycol Dicaprylate/Dicaprate | 5.00 |
| Dioctyl Butamido Triazone | 3.00 |
| Aniso Triazine | 1.00 |
| Repellent 3535 | 8.00 |
| Titanium Dioxide | 2.00 |
| Glycerin | 5.00 |
| micronized UV absorber of formula (7a), (7b) or (7d) | 1.50 |
| $MgSO_4$ | 1.00 |
| Preservatives, Parfum, Dyes | q.s. |
| Water | ad 100 |

Example 17.4: O/W Emulsion

| | % b.w. |
|---|---|
| Sorbitan Stearate | 3.00 |
| Polyglyceryl-2 Dipolyhydroxystearate | 1.50 |
| Octyldodecanol | 10.00 |
| Dicaprylyl Ether | 5.00 |
| Cetylstearylisononanoate | 2.00 |
| Butylene Glycol Dicaprylate/Dicaprate | 5.00 |
| Vitamine E Acetate | 0.50 |
| Dioctyl Butamido Triazone | 6.00 |
| Repellent 3535 | 10.00 |
| Octyltriazone | 4.00 |
| Butyl Methoxydibenzoylmethane | 3.00 |
| Glycerin | 10.00 |
| micronized UV absorber of formula (7a), (7b) or (7d) | 1.80 |
| Xanthan Gum | 0.20 |
| Phenylbenzimidazole Sulfonic Acid | 2.00 |
| NaOH 45% | 1.20 |
| Preservatives, Parfum, Dyes | q.s. |
| Water | ad 100 |

Example 17.5: W/O W Emulsion

| | % b.w. |
|---|---|
| PEG-30 Dipolyhydroxystearate | 4.00 |
| Caprylic Acid/Capric Acid Triglyceride | 5.00 |
| Octyldodecanol | 5.00 |
| Dicaprylyl Ether | 5.00 |
| Mineral Oil | 5.00 |
| Isohexadecane | 5.00 |
| Vitamine E Acetate | 0.50 |
| Dioctyl Butamido Triazone | 5.00 |
| Repellent 3535 | 15.00 |
| Aerosil R 972 | 0.50 |
| Glycerin | 10.00 |
| micronized UV absorber of formula (7a), (7b) or (7d) | 1.50 |
| $MgSO_4$ | 1.00 |
| Preservatives, Parfum, Dyes | q.s. |
| Water | ad 100 |

Example 17.6: W/O Emulsion

| | % b.w. |
|---|---|
| Cetyldimethicone Copolyol | 5.00 |
| Dimethicone | 5.00 |
| Isohexadecane | 2.00 |
| Butylene Glycol Dicaprylate/Dicaprate | 8.00 |
| $C_{12-15}$ Alkylbenzoate | 5.00 |
| Dioctyl Butamido Triazone | 2.00 |
| Aniso Triazine | 2.00 |
| Repellent 3535 | 10.00 |
| Octyltriazone | 1.00 |
| 4-Methylbenzylidene Camphor | 4.00 |
| Butyl Methoxydibenzoylmethane | 2.00 |
| Titanium Dioxide | 2.00 |
| micronized UV absorber of formula (7a), (7b) or (7d) | 2.50 |
| Glycerin | 5.00 |
| NaCl | 1.00 |
| Phenylbenzimidazole Sulfonic Acid | 4.00 |
| NaOH 45% | 1.30 |
| Preservatives, Parfum, Dyes | q.s. |
| Water | ad 100 |

Example 17.7: Spray

| | % b.w. |
|---|---|
| Glycerin Monostearate | 4.00 |
| Ceth 12 | 1.50 |
| Caprylic Acid/Capric Acid Triglyceride | 2.00 |
| Mineral Oil | 5.00 |
| Dioctyl Butamido Triazone | 0.50 |
| Repellent 3535 | 2.00 |
| Octyltriazone | 1.00 |
| Butyl Methoxydibenzoylmethane | 1.00 |
| Glycerin | 10.00 |
| micronized UV absorber of formula (7a), (7b) or (7d) | 1.50 |
| Phenylbenzimidazole Sulfonic Acid | 1.00 |
| NaOH 45% | 0.40 |
| Preservatives, Parfum, Dyes | q.s. |
| Water | ad 100 |

Example 17.8: Spray

| | % b.w. |
|---|---|
| Glycerin Monostearate SE | 4.00 |
| Cetheareth-12 | 1.50 |
| Caprylylether | 5.00 |
| Cetylstearylisononanoate | 5.00 |
| Dimethicone | 2.00 |
| Dioctyl Butamido Triazone | 1.00 |
| Aniso Triazine | 1.00 |
| Repellent 3535 | 5.00 |
| Glycerin | 5.00 |
| micronized UV absorber of formula (7a), (7b) or (7d) | 1.20 |
| Preservatives, Parfum, Dyes | q.s. |
| Water | ad 100 |

18. Neo Heliopan AP combined with 0.1% to 10% of microfine (particle size between 10 nm and 2 μm) naphthalene amidine imide compound

| Examples 18.1-18.6 | 18.1 O/W1 | 18.2 O/W2 | 18.3 O/W3 | 18.4 W/O1 | 18.5 W/O2 | 18.6 W/O3 |
|---|---|---|---|---|---|---|
| Stearic Acid | 1.50 | 1.50 | | | | |
| Glyceryl Mono Stearate | 3.00 | 3.00 | | | | |
| Sorbitan Stearate | | | 3.00 | | | |
| Polyglyceryl-3 Methylglucose Distearate | | | 1.5 | | | |
| Polyglyceryl-2 Dipolyhydroxystearate | | | | 5.00 | | |
| Cetyl Dimethicone Copolyol | | | | | | 5.00 |
| PEG-30 Dipolyhydroxystearate | | | | | 4.00 | |
| Dimethicone | | | | 2.00 | | 5.00 |
| Phenyl Trimethicone | 2.00 | | | | 5.00 | 3.00 |
| Vitamine E Acetate | 0.50 | 0.50 | 0.50 | | 0.50 | |
| Caprylic Acid/Capric Acid Triglyceride | 5.00 | | | 5.00 | | |
| Mineral Oil | | | | 8.00 | 5.00 | |
| C$_{12-15}$ Alkylbenzoate | 5.00 | | 2.00 | | 5.00 | |
| Butylene Glycol Dicaprylate/Dicaprate | | | 2.00 | | 7.00 | |
| Dicaprylyl Ether | 3.00 | | 5.00 | | 6.00 | |
| Dioctyl Butamido Triazone | 1.00 | | | 3.00 | | |
| Aniso Triazine | 2.00 | 1.00 | 0.50 | 2.00 | 1.00 | 0.50 |
| Octyl Triazone | 1.00 | | | 2.00 | | 1.00 |
| micronized UV absorber of formula (7a), (7b) or (7d) | 1.00 | 2.00 | 1.00 | 2.50 | 3.50 | 5.00 |
| 4-Methylbenzylidene Camphor | | | | 2.00 | | 5.00 |
| Ethylhexyl Methoxycinnamate | | | 2.00 | 2.00 | | 5.00 |
| Titanium Dioxide | 1.00 | 2.00 | | 2.00 | | |
| Aerosil R 972 | | | | | 0.50 | |
| Preservatives | 0.50 | 0.50 | 0.50 | 0.50 | 0.50 | 0.50 |
| Glycerin | 3.00 | 10.00 | 10.00 | 5.00 | 10.00 | 5.00 |
| Phenylbenzimidazole Sulfonic Acid | | | 3.00 | | | 3.00 |
| Bisoctyltriazol | 0.50 | | | 1.00 | | |
| Phenylbenzimidazole Sulfonic Acid | 1.00 | 0.50 | 0.50 | 5.00 | 4.00 | 5.00 |
| MgSO$_4$ | | | | 1.00 | 1.00 | |
| NaCl | | | | | | 1.00 |
| Xanthan Gum | 0.30 | 0.30 | | | | |
| Crosslinked Acrylic Acid/(C$_{10-30}$) Alkyl Acrylate Copolymer | | | 0.10 | | | |
| NaOH 45% | 0.50 | 0.50 | 1.80 | 2.00 | 3.00 | 2.50 |
| Water | ad 100 | ad 100 | ad 100 | ad 100 | ad 100 | ad 100 |

19. Imido succinic acid or salts thereof (for example. Baypure CX 100) combined with 0.1% to 10% of micro-fine (particle size between 10 nm and 2 μm) naphthalene amidine imide compound 20. PVP-polymers combined with 0.1% to 10% of micro-fine (particle size between 10 nm and 2 μm) naphthalene amidine imide compound

| Examples 20.1-20.6 | 20.1 | 20.2 | 20.3 | 20.4 | 20.5 | 20.6 |
|---|---|---|---|---|---|---|
| Mineral Oil | 5 | | 5 | | | 7 |
| C$_{12-15}$ Alkylbenzoate | 5 | 5 | 10 | | 7 | |
| Caprylic Acid/Capric Acid Triglyceride | 5 | | 5 | 8 | 5 | 7 |
| Butylene Glycol Dicaprylate/Dicaprate | 5 | 5 | | 8 | | |
| C18-36 Triglyceride | 2.5 | | 2 | 1.5 | 2 | 1 |
| Phenyl Trimethicone | 3 | | 3 | 1 | 2 | 5 |
| PVP Hexadecene Copolymer | 2 | 1.5 | 2 | 2.5 | 2 | |
| PVP Eicosene Copolymer | | | | | | 2 |
| Stannous Oxide | 3 | | | | | |
| Titanium Dioxide | 3 | | 1 | | | |
| Octyl Triazone | | 2 | | 2 | | |
| 4-Methylbenzylidene Camphor | | | | 4 | | |
| micronized UV absorber of formula (7a), (7b) or (7d) | 2 | 3 | 9 | 3 | 2 | 1 |
| Ethylhexyl Methoxycinnamate | | 5 | | 4 | 5 | |
| Butyl Methoxydibenzoylmethane | | | | 2 | | |
| Octocrylene | | 5 | | | | 5 |

-continued

| Examples 20.1-20.6 | 20.1 | 20.2 | 20.3 | 20.4 | 20.5 | 20.6 |
|---|---|---|---|---|---|---|
| Dioctyl Butamido Triazone | | | | | 2 | |
| Vitamine E Acetate | 0.5 | 1 | | 0.3 | 0.5 | |
| Phenylbenzimidazole Sulfonic Acid | | | | 1 | | |
| Bisimidazylate | | | | | 2 | |
| NaOH 45% | | | | 0.3 | 0.5 | |
| Glycerin | 10 | 5 | 5 | 3 | 5 | |
| MgSO$_4$ | | 1 | | | | |
| Sodium Lactate | 1 | | | | | 1 |
| Preservatives | 0.5 | 0.5 | 0.5 | 0.5 | 0.5 | 0.5 |
| Water | ad 100 | ad 100 | ad 100 | ad 100 | ad 100 | ad 100 |

21. Hydro-colloids combined with 0.1% to 10% of micro-fine (particle size between 10 nm and 2 μm) naphthalene amidine imide compound

| | % b.w. |
|---|---|
| Example 21.1 | |
| Caprylic Acid/Capric Acid Triglyceride | 10.00 |
| Dicaprylyl Ether | 5.00 |
| Dimethicone | 2.00 |
| Hydrated Polyisobutene | 2.00 |
| Vitamine E Acetate | 0.5 |
| Octyltriazone | 2.00 |
| Dioctyl Butamido Triazone | 2.00 |
| Butyl Methoxydibenzoylmethane | 2.00 |
| Titanium Dioxide | 1.00 |
| C18-36 Triglyceride | 5.00 |
| Glycerin | 3.00 |
| Xanthan Gum | 0.50 |
| Carbopol | 0.10 |
| NaOH 45% | 0.10 |
| Preservatives | q.s. |
| Water | ad 100 |
| Example 21.2 | |
| *Ricinus* Oil | 2.00 |
| Butylene Glycol Dicaprylate/Dicaprate | 10.00 |
| C$_{12-15}$ Alkylbenzoate | 5.00 |
| Octyltriazone | 4.00 |
| 4-Methylbenzylidene Camphor | 4.00 |
| Butyl Methoxydibenzoylmethane | 2.00 |
| micronized UV absorber of formula (7a), (7b) or (7d) | 1.50 |
| C18-36 Triglyceride | 2.00 |
| C16-24 Triglyceride | 2.00 |
| Glycerin | 10.00 |
| Xanthan Gum | 0.20 |
| Crosslinked Acrylic Acid/(C$_{10-30}$) Alkyl Acrylate Copolymer | 0.50 |
| Phenylbenzimidazole Sulfonic Acid | 2.00 |
| NaOH 45% | 1.20 |
| Preservatives, Parfum, Dyes | q.s. |
| Water | ad 100 |
| Example 21.3 | |
| Dimethicone | 5.00 |
| Mineral Oil | 3.00 |
| Isohexadecane | 2.00 |
| Hydrated Polyisobutene | 5.00 |
| Butylene Glycol Dicaprylate/Dicaprate | 5.00 |
| Ethylhexyl Methoxycinnamate | 5.00 |
| C18-36 Triglyceride | 3.00 |
| Glycerin | 5.00 |
| micronized UV absorber of formula (7a), (7b) or (7d) | 0.80 |
| Hydroxypropylmethylcellulose | 0.5 |
| Hectorit | 1.00 |
| Preservatives, Parfum, Dyes | q.s. |
| Water | ad 100 |
| Example 21.4 | |
| Caprylic Acid/Capric Acid Triglyceride | 5.00 |
| Octyldodecanol | 5.00 |

-continued

| | % b.w. |
|---|---|
| Butylene Glycol Dicaprylate/Dicaprate | 5.00 |
| Octyltriazone | 4.00 |
| Dioctyl Butamido Triazone | 4.00 |
| 4-Methylbenzylidene Camphor | 4.00 |
| Butyl Methoxydibenzoylmethane | 4.00 |
| Titanium Dioxide | 2.00 |
| C18-36 Triglyceride | 3.00 |
| C16 Triglyceride | 1.00 |
| Glycerin | 5.00 |
| micronized UV absorber of formula (7a), (7b) or (7d) | 1.50 |
| Xanthan Gum | 0.20 |
| Hydroxypropylmethylcellulose | 0.20 |
| Phenylbenzimidazole Sulfonic Acid | 4.00 |
| NaOH 45% | 1.30 |

22. Non-ionic emulsifiers and silicon emulsifiers combined with 0.1% to 10% of micro-fine (particle size between 10 nm and 2 μm) tris-biphenyl-triazine or tris-terphenyl-triazine

| Examples 22.1-22.3 | 22.1 | 22.2 | 22.3 |
|---|---|---|---|
| Cetyl Dimethicone Copolyol | 5.00 | 6.00 | 3.00 |
| Mineral Oil | 14.00 | 4.00 | 10.00 |
| Caprylic Acid/Capric Acid Triglyceride | 14.00 | 6.00 | 10.00 |
| C$_{12-15}$ Alkylbenzoate | | 5.00 | |
| Butylene Glycol Dicaprylate/Dicaprate | | 10.00 | 10.00 |
| MgSO$_4$ | 0.70 | 0.70 | 0.70 |
| Decylglucoside | 2.50 | 0.20 | 1.50 |
| Butyl Methoxydibenzoylmethane | | 2.00 | |
| 4-Methylbenzylidene Camphor | | 4.00 | |
| BEMBT | 10.00 | 2.00 | 6.0 |
| Titanium Dioxide | | | 6.00 |
| micronized UV absorber of formula (7a), (7b) or (7d) | 2.50 | 3.00 | 3.50 |
| Phenylbenzimidazole Sulfonic Acid | | 1.00 | |
| NaOH 45% | | 0.30 | |
| EDTA Solution | | 1.00 | |
| Preservatives, Parfum, Dyes | q.s. | q.s. | q.s. |
| Water | ad 100 | ad 100 | ad 100 |

| Examples 22.4-22.6 | 22.4 | 22.5 | 22.6 |
|---|---|---|---|
| Cetyl Dimethicone Copolyol | 5.00 | 6.00 | 3.00 |
| Mineral Oil | 14.00 | 4.00 | 10.00 |
| Caprylic Acid/Capric Acid Triglyceride | 14.00 | 6.00 | 10.00 |
| C$_{12-15}$ Alkylbenzoate | | 5.00 | |
| Butylene Glycol Dicaprylate/Dicaprate | | 10.00 | 10.00 |
| Glycerin | 3.00 | 5.00 | 10.00 |
| MgSO$_4$ | 0.70 | 0.70 | 0.70 |
| Cetylstearylglucoside | 2.50 | 0.20 | 1.50 |
| Butyl Methoxydibenzoylmethane | | 2.00 | |
| 4-Methylbenzylidene Camphor | | 4.00 | |
| BEMBT | 10.00 | 2.00 | 6.0 |
| Titanium Dioxide | | | 6.00 |
| micronized UV absorber of formula | 2.50 | 0.50 | 1.50 |

| (7a), (7b) or (7d) | | | |
|---|---|---|---|
| Phenylbenzimidazole Sulfonic Acid | 1.00 | | |
| NaOH 45% | 0.30 | | |
| EDTA Solution | 1.00 | | |
| Preservatives, Parfum, Dyes | q.s. | q.s. | q.s. |
| Water | ad 100 | ad 100 | ad 100 |

23. Amphoteric and ionic emulsifiers combined with 0.1% to 10% of micro-fine (particle size between 10 nm and 2 μm) naphthalene amidine imide compound

| Examples 23.1-23.3 | 23.1 | 23.2 | 23.3 |
|---|---|---|---|
| PEG-30 Dipolyhydroxystearate | 5.00 | 6.00 | 3.00 |
| Cetyl Dimethicone Copolyol | 5.00 | 6.00 | 5.00 |
| Mineral Oil | 14.00 | 4.00 | 10.00 |
| Caprylic Acid/Capric Acid Triglyceride | 14.00 | 6.00 | 10.00 |
| $C_{12-15}$ Alkylbenzoate | | 5.00 | |
| Butylene Glycol Dicaprylate/Dicaprate | | 10.00 | 10.00 |
| Glycerin | 3.00 | 5.00 | 10.00 |
| $MgSO_4$ | 0.70 | 0.70 | 0.70 |
| Laurylethersulfate | 2.50 | 0.20 | 1.50 |
| Butyl Methoxydibenzoylmethane | | 2.00 | |
| micronized UV absorber of formula (7a), (7b) or (7d) | 10.00 | 8.00 | 6.00 |
| 4-Methylbenzylidene Camphor | | 4.00 | |
| BEMBT | 10.00 | 2.00 | 6.0 |
| Titanium Dioxide | | | 6.00 |
| Phenylbenzimidazole Sulfonic Acid | | 1.00 | |
| NaOH 45% | | 0.30 | |
| EDTA Solution | | 1.00 | |
| Preservatives Parfum, Dyes | q.s. | q.s. | q.s. |
| Water | ad 100 | ad 100 | ad 100 |

| Examples 23.4-23.6 | 23.4 | 23.5 | 23.6 |
|---|---|---|---|
| PEG-30 Dipolyhydroxystearate | 5.00 | 6.00 | 3.00 |
| Cetyl Dimethicone Copolyol | 5.00 | 6.00 | 5.00 |
| Mineral Oil | 14.00 | 4.00 | 10.00 |
| Caprylic Acid/Capric Acid Triglyceride | 14.00 | 6.00 | 10.00 |
| $C_{12-15}$ Alkylbenzoate | | 5.00 | |
| Butylene Glycol Dicaprylate/Dicaprate | | 10.00 | 10.00 |
| Glycerin | 3.00 | 5.00 | 10.00 |
| $MgSO_4$ | 0.70 | 0.70 | 0.70 |
| Sodiumisostearoyllactylate | 2.50 | 0.20 | 1.50 |
| Butyl Methoxydibenzoylmethane | | 2.00 | |
| micronized UV absorber of formula (7a), (7b) or (7d) | 5.00 | 4.00 | 3.00 |
| 4-Methylbenzylidene Camphor | | 4.00 | |
| BEMBT | 10.00 | 2.00 | 6.0 |
| Titanium Dioxide | | | 6.00 |
| Phenylbenzimidazole Sulfonic Acid | | 1.00 | |
| NaOH 45% | | 0.30 | |
| EDTA Solution | | 1.00 | |
| Preservatives Parfum, Dyes | q.s. | q.s. | q.s. |
| Water | ad 100 | ad 100 | ad 100 |

24. Emulsifier-free formulation with hydrophobic micro pigments combined with 0.1% to 10% of micro-fine (particle size between 10 nm and 2 μm) naphthalene amidine imide compound
25. Layered silicates or modified layered silicates combined with 0.1% to 10% of micro-fine (particle size between 10 nm and 2 μm) naphthalene amidine imide compound

| Examples 25.1-25.5 | 25.1 | 25.2 | 25.3 | 25.4 | 25.5 |
|---|---|---|---|---|---|
| Aerosil R 972 | | | 0.50 | | |
| Quaternium-18 Hectorite (Bentone 38) | 0.5 | 0.25 | | 0.10 | 0.30 |
| Stearalkonium Hectorite (Bentone 27) | | | 0.20 | 0.10 | |
| Preservatives | 0.50 | 0.50 | 0.50 | 0.50 | 0.50 |
| Glycerin | 5.00 | 5.00 | 10.00 | 10.00 | 5.00 |
| micronized UV absorber of formula (7a), (7b) or (7d) | 4.00 | 2.00 | 3.00 | 1.00 | 5.00 |
| $MgSO_4$ | 1 | 1 | 1 | 1 | |
| NaCl | | | | | 1 |
| Phenylbenzimidazole Sulfonic Acid | | | | | 4 |
| NaOH 45% | | | | | 1.3 |
| Water | ad 100 | ad 100 | ad 100 | ad 100 | ad 100 |

26. K80D from Koster Keunen combined with 0.1% to 10% of micro-fine (particle size between 10 nm and 2 μm) naphthalene amidine imide compound
27. Natural or synthetic bees wax combined with 0.1% to 10% of micro-fine (particle size between 10 nm and 2 μm) naphthalene amidine imide compound

| | % b.w. |
|---|---|
| Example 27.1: Hydrodispersion Gel | |
| Crosslinked Acrylic Acid/($C_{10-30}$) Alkyl Acrylate Copolymer | 0.50 |
| Ethanol | 3.50 |
| Glycerin | 3.00 |
| Dimethicone | 1.50 |
| Octyldodecanol | 0.50 |
| Caprylic Acid/Capric Acid Triglyceride | 5.00 |
| Bees wax | 2.00 |
| Butyl Methoxydibenzoylmethane (Parsol 1789) | 5.00 |
| micronized UV absorber of formula (7a), (7b) or (7d) | 1.50 |
| Carbomer | 0.20 |
| NaOH 45% | 0.55 |
| Preservatives | q.s. |
| Parfum | q.s. |
| Water deion. | ad 100 |
| Example 27.2: W/O Lotion | |
| Glycerylstearate SE | 3.50 |
| Stearic Acid | 1.80 |
| Glycerin | 3.00 |
| Cetearyl Alcohol | 0.50 |
| Octyldodecanol | 7.00 |
| Dicaprylyl Ether | 8.00 |
| Butyl Methoxydibenzoylmethane (Parsol 1789) | 3.00 |
| Synthetic Bees wax | 1.00 |
| micronized UV absorber of formula (7a), (7b) or (7d) | 2.50 |
| Carbomer | 0.20 |
| NaOH 45% | 0.20 |
| Preservatives | q.s. |
| Parfum | q.s. |
| Water deion. | ad 100 |
| Example 27.3: O/W Lotion | |
| Glycerylstearate SE | 3.50 |
| Stearic Acid | 1.80 |
| Glycerin | 3.00 |
| Cetearyl al | 0.50 |
| Octyldodecanol | 7.00 |
| Dicaprylyl Ether | 8.00 |
| Butyl Methoxydibenzoylmethane (Parsol 1789) | 3.00 |
| Synthetic Bees wax | 1.00 |
| micronized UV absorber of formula (7a), (7b) or (7d) | 2.00 |
| Carbomer | 0.20 |
| NaOH 45% | 0.20 |
| Preservatives | q.s. |
| Parfum | q.s. |
| Water deion. | ad 100 |
| Example 27.4: Hydrodispersion Gel | |
| Crosslinked Acrylic Acid/($C_{10-30}$) Alkyl Acrylate Copolymer | 0.50 |
| Ethanol | 3.50 |

-continued

| | % b.w. |
|---|---|
| Glycerin | 3.00 |
| Dimethicone | 1.50 |
| Octyldodecanol | 0.50 |
| Caprylic Acid/Capric Acid Triglyceride | 5.00 |
| Synthetic Bees wax | 2.00 |
| Butyl Methoxydibenzoylmethane (Parsol 1789) | 5.00 |
| micronized UV absorber of formula (7a), (7b) or (7d) | 3.00 |
| Carbomer | 0.20 |
| NaOH 45% | 0.55 |
| Preservatives | q.s. |
| Parfum | q.s. |
| Water deion. | ad 100 |

28. $FeTiO_2$ (T817 from Degussa) combined with 0.1% to 10% of micro-fine (particle size between 10 nm and 2 μm) naphthalene amidine imide compound 29. Organo-modified silicone like Abil EM 90, Abil EM 97, Fluid DC 193 Silicone DC 3225C or Cyclomethicone-dimethicone copolyoles combined with 0.1% to 10% of micro-fine (particle size between 10 nm and 2 μm) naphthalene amidine imide compound

| Example 29.1: W/O Emulsion | [g] |
|---|---|
| Oxyethylenated polydimethyl/methylcetyl methylsiloxane | 2.00 |
| Phenyl Trimethylsiloxy Trisiloxane | 3.00 |
| $C_{12-15}$ Alkylbenzoate | 8.00 |
| Methylene Bis-Benzotriazolyl Tetramethylbutylphenol in micronized form (Tinosorb M) | 5 |
| micronized UV absorber of formula (7a), (7b) or (7d) | |
| Drometrizole Trisiloxane | 2 |
| Bis-Ethylhexyloxyphenol Methoxyphenyl Triazine (Tinosorb S) | 2 |
| Titanium Dioxide | 3 |
| Glycerin | 5 |
| $MgSO_4$ | 0.70 |
| Preservatives | q.s. |
| Demineralized water | ad 100 |

30. Insoluble organic compounds containing benzazole, benzothiophene, benzofurane or indol groups combined with 0.1% to 10% of micro-fine (particle size between 10 nm and 2 μm) tris naphthalene amidine imide compound

| Example 30.1: | [g] |
|---|---|
| Mixture of Mono- and Distearate of Gglycerol/PEG 100 Stearate | 2 |
| Stearyl Alcohol | 1 |
| Stearic Acid of Palme Oil | 2.50 |
| Polydimethylsiloxane | 0.50 |
| $C_{12-15}$ Alkylbenzoate | 20.00 |
| Triethanolamine | 0.50 |
| Aqueous dispersion of 1,4-phenylene-bis(2-benzoxazoyle) (38%) | 13.2 |
| Glycerin | 4 |
| micronized UV absorber of formula (7a), (7b) or (7d) | 4 |
| Hexadecyl Alcohol Phosphate Potassium Salt | 0.5 |
| Triethanolamine | 0.30 |
| Polyacrylic Acid | 0.30 |
| Preservatives | q.s. |
| Water demin. | ad 100 |

31. 4,4-diarylbutadiene combined with 0.1% to 10% of micro-fine (particle size between 10 nm and 2 μm) naphthalene amidine imide compound

| Example 31.1 | [g] |
|---|---|
| Mixture of mono- and distearate of Glycerol/PEG 100 Stearate | 2.00 |
| Stearyl Alcohol | 1.00 |
| Stearic Acid of Palme Oil | 2.50 |
| Polydimethylsiloxane | 0.50 |
| $C_{12-15}$ Alkylbenzoate | 20.00 |
| Triethanolamine | 0.50 |
| Butyl Methoxydibenzoylmethane | 2.00 |
| Glycerin | 4.00 |
| micronized UV absorber of formula (7a), (7b) or (7d) | 0.40 |
| Triethanolamine | 0.30 |
| Polyacrylic acid | 0.30 |
| Preservatives | q.s. |
| Water demin. | ad 100 |

32. Amphiphilic polymer combined with 0.1% to 10% of micro-fine (particle size between 10 nm and 2 μm) naphthalene amidine imide compound

| Example 32.1 | | [g] |
|---|---|---|
| Phase A | Octocrylene | 9.00 |
| | Butyl Methoxydibenzoylmethane | 2.50 |
| | Dromtrizole Trisiloxane | 0.75 |
| | Decylcocoate | 9.00 |
| Phase B | Copolymer of acrylamide-2-methyl-2-propanesulfonic-acid anddodecylamide 3.5%/99.5%) | 1.50 |
| Phase C | Glycerin | 4.00 |
| | Propylene glycol | |
| | EDTA disodium salt | 0.10 |
| | Preservatives | q.s. |
| | 4-Methylbenzylidene Camphor | 1.50 |
| | Triethanolamine | 0.26 |
| | Water | ad 100 |
| Phase D | Coated Titanium Dioxide | 16.7 |
| | micronized UV absorber of formula (7a), (7b) or (7d) | 2.00 |

33. A polymer containing at least one ethylenic unsaturated monomer with a sulfonic group and a hydrophobic part combined with 0.1% to 10% of micro-fine (particle size between 10 nm and 2 μm) naphthalene amidine imide compound

| | [g] |
|---|---|
| Example 33.1 | |
| $C_{12-15}$ Alkylbenzoate | 10.00 |
| Methylene Bis-Benzotriazolyl Tetramethylbutylphenol in micronized form (Tinosorb M) | 2.50 |
| Octocrylene | 5.00 |
| Butyl Methoxydibenzoylmethane | 2.00 |
| Crosslinked Acrylic Acid/($C_{10-30}$) Alkyl Acrylate Copolymer | 0.75 |
| Titanium Dioxide | 3.00 |
| EDTA | 0.10 |
| 4-Methylbenzylidene Camphor | 0.50 |
| Glycerin | 5.00 |
| micronized UV absorber of formula (7a), (7b) or (7d) | 2.50 |
| Triethanolamine | q.s. |
| Water demin. | ad 100 |
| Example 33.2 | |
| $C_{12-15}$ Alkylbenzoate | 8.00 |
| Methylene Bis-Benzotriazolyl Tetramethylbutylphenol (Tinosorb M) | 3.00 |
| Octocrylene | 5.00 |
| Bis-Ethylhexyloxyphenol Methoxyphenyl Triazine (Tinosorb S) | 3.00 |
| Crosslinked Acrylic Acid/($C_{10-30}$) Alkyl Acrylate Copolymer | 5.00 |
| Titanium Dioxide | 3.00 |

-continued

| | [g] |
|---|---|
| Glycerin | 5.00 |
| micronized UV absorber of formula (7a), (7b) or (7d) | 3.00 |
| Triethanolamine | q.s. |
| Water demin. | ad 100 |

33. Triazine derivates or benztriazole and siloxane elastomer combined with 0.1% to 10% of micro-fine (particle size between 10 nm and 2 μm) naphthalene amidine imide compound
34. Hexadecene dicarbonic acid combined with 0.1% to 10% of micro-fine (particle size between 10 nm and 2 μm) naphthalene amidine imide compound
35. Phosphonates combined with 0.1% to 10% of micro-fine (particle size between 10 nm and 2 μm) naphthalene amidine imide compound
36. Acryl amid polymer combined with 0.1% to 10% of micro-fine (particle size between 10 nm and 2 μm) naphthalene amidine imide compound
37. Pickering emulsion combined with 0.1% to 10% of micro-fine (particle size between 10 nm and 2 μm) naphthalene amidine imide compound

| Example 37.1-37.5 | 37.1 | 37.2 | 37.3 | 37.4 | 37.5 |
|---|---|---|---|---|---|
| Emulsion Type | W/O | W/O | W/O | O/W | O/W |
| Titanium Dioxide | 4.00 | 2.00 | | 4.00 | 2.00 |
| Stannous Oxide | | | | | 4 |
| Silica | 0.50 | | 1.00 | | |
| Talcum | | 2.00 | | | |
| Boron Nitride | | | 5.00 | | 2.00 |
| Dioctyl Succinate | | | | 2 | |
| Caprylic Acid/Capric Acid Triglyceride | 5.00 | 5.00 | 5.00 | 20.00 | 12.00 |
| Octyldodecanol | 10.000 | | 5.00 | 20.00 | |
| Mineral Oil | 10.00 | | 5.00 | 20.00 | |
| Butylene Glycol Dicaprylate/Dicaprate | | 10.00 | 10.00 | | 20.00 |
| C$_{12-15}$ Alkylbenzoate | 5.00 | 10.00 | 10.00 | 20.00 | 20.00 |
| Isohexadecane | | 1.00 | | | |
| Dicaprylyl Ether | | 1.00 | | 2.00 | |
| Cyclomethicone | 1.00 | 1.00 | | 2.00 | 2.00 |
| 4-Methylbenzylidene Camphor | | 3.00 | | | 2.00 |
| Octyltriazone | | 1.00 | | | 1.00 |
| Butyl Methoxydibenzoylmethane | | 2 | | | 2 |
| Titanium Dioxide | | | 4 | | |
| micronized UV absorber of formula (7a), (7b) or (7d) | 4.00 | 3.00 | 1.00 | 3.00 | 3.50 |
| Dioctylbutylalcohol | 4.00 | 2.00 | 6.00 | 4.00 | 8.00 |
| C$_{16-18}$ Alkylhydroxy-stearoylstearate | | 1.00 | | | |
| Hydroxyoctacosanylhydroxy-stearate | 2 | | | 2 | |

38. Monascus combined with 0.1% to 10% of micro-fine (particle size between 10 nm and 2 μm) naphthalene amidine imide compound
39. Butyl Methoxydibenzoylmethane and Diethylamino Hydroxybenzoyl Hexyl Benzoate combined with 0.1% to 10% of micro-fine (particle size between 10 nm and 2 μm) naphthalene amidine imide compound
40. Butyl Methoxydibenzoylmethane and Bis-ethylhexyloxyphenol methoxyphenyl triazine combined with 0.1% to 10% of micro-fine (particle size between 10 nm and 2 μm) naphthalene amidine imide compound
41. Butyl Methoxydibenzoylmethane and Octocrylene combined with 0.1% to 10% of micro-fine (particle size between 10 nm and 2 μm) naphthalene amidine imide compound
42. $C_6$-$C_{30}$ Fatty alcohols or acetylated fatty alcohols combined with 0.1% to 10% of micro-fine (particle size between 10 nm and 2 μm) naphthalene amidine imide compound
43. Fatty acid sacrosinate (for example Eldew SL-205 from Ajinomoto Comp.) combined with 0.1% to 10% of micro-fine (particle size between 10 nm and 2 μm) naphthalene amidine imide compound
44. Amphiphilic (block-)copolymers of ethylene oxide, propylene oxide or butylenes oxide (Copolyoles), they even may contain alkyl groups as a hydrophobic part (C6-C50) as described in EP1302197 combined with 0.1% to 10% of micro-fine (particle size between 10 nm and 2 μm) naphthalene amidine imide compound
45. Flavilium Salts of the general formula:

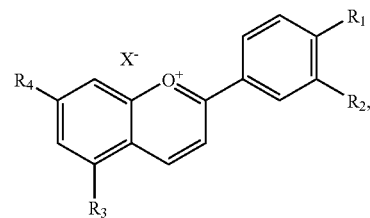

whereas $R_1$, $R_2$, $R_3$, $R_4$ are —OH or $C_1$ to $C_{10}$ alkyl, at least one of $R_1$ to $R_4$ is an —OH and X is an organic or mineral anionic group combined with 0.1% to 10% of micro-fine (particle size between 10 nm and 2 μm) naphthalene amidine imide compound
46. Compound of the formula $R'_1(CO)N(R'_2)CH(R'_3)(CH_2)_n(CO)OR'_4$, whereas n is 0, 1, 2 or 3; $R_1$ $C_5$ $C_{22}$ alkyl, $R_2$ and $R_3$ are a hydrogen or a $C_1$-$C_4$ alkyl group and $R_4$ represents a $C_1$ to $C_{10}$ alkyl or alKenyl-group or a styrene, combined with 0.1% to 10% of micro-fine (particle size between 10 nm and 2 μm) naphthalene amidine imide compound
47. *Vitreoscilla* Ferment combined with 0.1% to 10% of micro-fine (particle size between 10 nm and 2 μm) naphthalene amidine imide compound
48. *Scutellaria Baicalensis* combined with 0.1% to 10% of micro-fine (particle size between 10 nm and 2 μm) naphthalene amidine imide compound
49. *Morus Bombycis* combined with 0.1% to 10% of micro-fine (particle size between 10 nm and 2 μm) naphthalene amidine imide compound The cosmetic or pharmaceutical preparations may be, for example, creams, gels, lotions, alcoholic and aqueous/alcoholic solutions, emulsions, wax/fat compositions, stick preparations, powders or ointments. In addition to the above mentioned UV filters, the cosmetic or pharmaceutical preparations may contain further adjuvants as described below.

As water- and oil-containing emulsions (e.g. W/O, O/W, O/W/O and W/O/W emulsions or microemulsions) the preparations contain, for example, from 0.1 to 30% by weight, preferably from 0.1 to 15% by weight and especially from 0.5 to 10% by weight, based on the total weight of the composition, of one or more UV absorbers, from 1 to 60% by weight, especially from 5 to 50% by weight and preferably from 10 to 35% by weight, based on the total weight of the composition, of at least one oil component, from 0 to 30% by weight, especially from 1 to 30% by weight and preferably from 4 to 20% by weight, based on the total weight of the composition, of at least one emulsifier, from 10 to 90% by weight, especially from 30 to 90% by weight, based on the total weight of the composition, of water, and from 0 to 88.9% by weight, especially from 1 to 50% by weight, of further cosmetically acceptable adjuvants.

The cosmetic or pharmaceutical compositions/preparations according to the invention may also contain one or more additional compounds as described below.

Fatty Alcohols

Guerbet alcohols based on fatty alcohols having from 6 to 18, preferably from 8 to 10 carbon atoms including cetyl alcohol, stearyl alcohol, cetearyl alcohol, oleyl alcohol, octyldodecanol, benzoate of C12-C15 alcohols, acetylated lanolin alcohol, etc.

Esters of Fatty Acids

Esters of linear $C_6$-$C_{24}$ fatty acids with linear $C_3$-$C_{24}$ alcohols, esters of branched $C_6$-$C_{13}$ carboxylic acids with linear $C_6$-$C_{24}$ fatty alcohols, esters of linear $C_6$-$C_{24}$ fatty acids with branched alcohols, especially 2-ethylhexanol, esters of hydroxycarboxylic acids with linear or branched $C_6$-$C_{22}$ fatty alcohols, especially dioctyl malates, esters of linear and/or branched fatty acids with polyhydric alcohols (for example propylene glycol, dimer diol or timer triol) and/or Guerbet alcohols, for example caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and technical-grade mixtures thereof (obtained, for example, in the pressure removal of natural fats and oils, in the reduction of aldehydes from Roelen's oxosynthesis or in the dimerisation of unsaturated fatty acids) with alcohols, for example, isopropyl alcohol, caproic alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linoyl alcohol, linolenyl alcohol, elaeostearyl alcohol, arachidyl alcohol, gadoleyl alcohol, behenyl alcohol, erucyl alcohol and brassidyl alcohol and technical-grade mixtures thereof (obtained, for example, in the high-pressure hydrogenation of technical-grade methyl esters based on fats and oils or aldehydes from Roelen's oxosynthesis and as monomer fractions in the dimerisation of unsaturated fatty alcohols).

Examples of such ester oils are isopropylmyristate, isopropylpalmitate, isopropylstearate, isopropyl isostearate, isopropyloleate, n-butylstearate, n-hexyllaurate, n-decyloleate, isooctylstearate, iso-nonyistearate, isononyl isononanoate, 2-ethylhexylpalmitate, 2-hexyllaurate, 2-hexyldecylstearate, 2-octyldodecylpalmitate, oleyloleate, oleylerucate, erucyloleate, erucyl-erucate, cetearyl octanoate, cetyl palmitate, cetyl stearate, cetyl oleate, cetyl behenate, cetyl acetate, myristyl myristate, myristyl behenate, myristyl oleate, myristyl stearate, myristyl palmitate, myristyl lactate, propylene glycol dicaprylate/caprate, stearyl heptanoate, diisostearyl malate, octyl hydroxystearate, etc.

Natural or Synthetic Triglycerides Including Glyceryl Esters and Derivatives

Di- or tri-glycerides, based on $C_6$-$C_{18}$ fatty acids, modified by reaction with other alcohols (caprylic/capric triglyceride, wheat germ glycerides, etc.). Fatty acid esters of polyglycerin (polyglyceryl-n such as polyglyceryl-4 caprate, polyglyceryl-2 isostearate, etc. or castor oil, hydrogenated vegetable oil, sweet almond oil, wheat germ oil, sesame oil, hydrogenated cottonseed oil, coconut oil, avocado oil, corn oil, hydrogenated castor oil, shea butter, cocoa butter, soybean oil, mink oil, sunflower oil, safflower oil, macadamia nut oil, olive oil, hydrogenated tallow, apricot kernel oil, hazelnut oil, borago oil, etc.

Waxes including esters of long-chain acids and alcohols as well as compounds having wax-like properties, e.g., carnauba wax, beeswax (white or yellow), lanolin wax, candellila wax, ozokerite, japan wax, paraffin wax, microcrystalline wax, ceresin, cetearyl esters wax, synthetic beeswax, etc. Also, hydrophilic waxes as Cetearyl Alcohol or partial glycerides.

Pearlescent Waxes:

Ikylene glycol esters, especially ethylene glycol distearate; fatty acid alkanolamides, especially coco fatty acid diethanolamide; partial glycerides, especially stearic acid monoglyceride; esters of polyvalent, unsubstituted or hydroxy-substituted carboxylic acids with fatty alcohols having from 6 to 22 carbon atoms, especially long-chained esters of tartaric acid; fatty substances, for example fatty alcohols, fatty ketones, fatty aldehydes, fatty ethers and fatty carbonates, which in total have at least 24 carbon atoms, especially laurone and distearyl ether; fatty acids, such as stearic acid, hydroxystearic acid or behenic acid, ring-opening products of olefin epoxides having from 12 to 22 carbon atoms with fatty alcohols having from 12 to 22 carbon atoms and/or polyols having from 2 to 15 carbon atoms and from 2 to 10 hydroxy groups, and mixtures thereof.

Hydrocarbon Oils:

Mineral oil (light or heavy), petrolatum (yellow or white), microcrystalline wax, paraffinic and isoparaffinic compounds, hydrogenated isoparaffinic molecules as polydecenes and polybutene, hydrogenated polyisobutene, squalane, isohexadecane, isododecane and others from plant and animal kingdom.

Silicones or Siloxanes (Organosubstituted Polysiloxanes)

Dimethylpolysiloxanes, methylphenylpolysiloxanes, cyclic silicones, and also amino-, fatty acid-, alcohol-, polyether-, epoxy-, fluorine-, glycoside- and/or alkyl-modified silicone compounds, which at room temperature may be in either liquid or resinous form. Linear polysiloxanes, dimethicone (Dow Corning 200 fluid, Rhodia Mirasil DM), dimethiconol, cyclic silicone fluids, cyclopentasiloxanes volatiles (Dow Corning 345 fluid), phenyltrimethicone (Dow Corning 556 fluid). Also suitable are simethicones, which are mixtures of dimethicones having an average chain length of from 200 to 300 dimethylsiloxane units with hydrogenated silicates. A detailed survey by Todd et al. of suitable volatile silicones may in addition be found in Cosm. Toil. 91, 27 (1976).

Fluorinated or Perfluorinated Oils

Perfluorhexane, dimethylcyclohexane, ethylcyclopentane, polyperfluoromethylisopropyl ether.

Emulsifiers

Any conventionally usable emulsifier can be used for the compositions. Emulsifier systems may comprise for example: carboxylic acids and their salts: alkaline soap of sodium, potassium and ammonium, metallic soap of calcium or magnesium, organic basis soap such as Lauric, palmitic, stearic and oleic acid etc. . . . . . Alkyl phosphates or phosphoric acid esters, acid phosphate, diethanolamine phosphate, potassium cetyl phosphate. Ethoxylated carboxylic acids or polyethyleneglycol esters, PEG-n acylates. Linear fatty alcohols having from 8 to 22 carbon atoms, branched from 2 to 30 mol of ethylene oxide and/or from 0 to 5 mol propylene oxide with fatty acids having from 12 to 22 carbon atoms and with alkylphenols having from 8 to 15 carbon atoms in the alkyl group. Fatty alcohol polyglycolether such as laureth-n, ceteareth-n, stearenth-n, oleth-n. Fatty acid polyglycolether such as PEG-n stearate, PEG-n oleate, PEG-n cocoate. Monoglycerides and polyol esters. C12-C22 fatty acid mono- and di-esters of addition products of from 1 to 30 mol of ethylene oxide with polyols. Fatty acid and polyglycerol ester such as monostearate glycerol, diisostearoyl polyglyceryl-3-diisostearates, polyglyceryl-3-diisostearates, triglyceryl diisostearates, polyglyceryl-2-sesquiisostearates or polyglyceryl dimerates. Mixtures of compounds from a plurality of those substance classes are also suitable. Fatty acid polyglycolesters such as monostearate diethylene glycol, fatty acid and polyethylene glycol esters, fatty acid and saccharose esters such as sucro esters, glycerol and saccharose esters such as sucro glycerides. Sorbitol and sorbitan, sorbitan mono- and di-esters of saturated and unsaturated fatty acids having from 6 to 22 carbon atoms and ethylene oxide addition products. Polysorbate-n series, sorbitan esters such as sesquiisostearate, sorbitan, PEG-(6)-isostearate sorbitan, PEG-(10)-sorbitan laurate, PEG-17-dioleate sorbitan. Glucose derivatives, $C_8$-$C_{22}$ alkyl-mono and oligo-glycosides and ethoxylated analogues with glucose being preferred as the sugar component. O/W emulsifiers such as methyl gluceth-20 sesquistearate, sorbitan stearate/sucrose cocoate, methyl glucose sesquistearate, cetearyl alcohol/cetearyl glucoside. W/O emulsifiers such as methyl glucose dioleate/methyl glucose isostearate. Sulfates and sulfonated derivatives, dialkylsulfosuccinates, dioctyl succinate, alkyl lauryl sulfonate, linear sulfonated parafins, sulfonated tetraproplyne sulfonate, sodium lauryl sulfates, ammonium and ethanolamine lauryl sulfates, lauyl ether sulfates, sodium laureth sulfates, sulfosuccinates, aceyl isothionates, alkanolamide sulfates, taurines, methyl taurines, imidazole sulfates. Amine derivatives, amine salts, ethoxylated amines, oxide amine with chains containing an heterocycle such as alkyl imidazolines, pyridine derivatives, isoquinoteines, cetyl pyridinium chlorure, cetyl pyridinium bromide, quaternary ammonium such as cetyltrimethylbroide amonium broide (CTBA), stearylalkonium. Amide derivatives, alkanolamides such as acylamide DEA, ethoxylated amides such as PEG-n acylamide, oxydeamide. Polysiloxane/polyalkyl/polyether copolymers and derivatives, dimethicone, copolyols, silicone polyethylene oxide copolymer, silicone glycol copolymer. Propoxylated or POE-n ethers (Meroxapols), Polaxamers or poly(oxyethylene)m-block-poly(oxypropylene)n-block(oxyethylene).

Zwitterionic surfactants that carry at least one quaternary ammonium group and at least one carboxylate and/or sulfonate group in the molecule. Zwitterionic surfactants that are especially suitable are betaines, such as N-alkyl-N,N-dimethylammonium glycinates, cocoalkyldimethylammonium glycinate, N-acylaminopropyl-N,N-dimethyl-ammonium glycinates, cocoacylaminopropyldimethylammonium glycinate and 2-alkyl-3-carboxymethyl-3-hydroxyethylimidazolines each having from 8 to 18 carbon atoms in the alkyl or acyl group and also cocoacylaminoethylhydroxyethylcarboxymethylglycinate, N-alkylbetaine, N-alkylaminobetaines. Alkylimidazolines, alkylopeptides, lipoaminoacides, self emulsifying bases and the compounds as described in K. F. DePolo, A short textbook of cosmetology, Chapter 8, Table 8-7, p250-251.

Non ionic emulsifiers such as PEG-6 beeswax (and) PEG-6 stearate (and) polyglyceryl-2-isostearate [Apifac], glyceryl stearate (and) PEG-100 stearate. [Arlacel 165], PEG-5 glyceryl stearate [arlatone 983 S], sorbitan oleate (and) polyglyceryl-3 ricinoleate. [Arlacel 1689], sorbitan stearate and sucrose cocoate [arlatone 2121], glyceryl stearate and laureth-23 [Cerasynth 945], cetearyl alcohol and ceteth-20 [Cetomacrogol Wax], cetearyl alcohol and colysorbate 60 and PEG-150 and stearate-20[Polawax GP 200, Polawax NF], cetearyl alcohol and cetearyl polyglucoside [Emulgade PL 1618], cetearyl alcohol and ceteareth-20 [Emulgade 1000NI, Cosmowax], cetearyl alcohol and PEG-40 castor oil [Emulgade F Special], cetearyl alcohol and PEG-40 castor oil and sodium cetearyl sulfate [Emulgade F], stearyl alcohol and steareth-7 and steareth-10 [Emulgator E 2155], cetearyl alcohol and szeareth-7 and steareth-10 [Emulsifying wax U.S.N.F], glyceryl stearate and PEG-75 stearate [Gelot 64], propylene glycol ceteth-3 acetate. [Hetester PCS], propylene glycol isoceth-3 acetate [Hetester PHA], cetearyl alcohol and ceteth-12 and oleth-12 [Lanbritol Wax N 21], PEG-6 stearate and PEG-32 stearate [Tefose 1500], PEG-6 stearate and ceteth-20 and steareth-20 [Tefose 2000], PEG-6 stearate and ceteth-20 and glyceryl stearate and steareth-20 [Tefose 2561], glyceryl stearate and ceteareth-20 [Teginacid H, C, X].

Anionic emulsifiers such as PEG-2 stearate SE, glyceryl stearate SE [Monelgine, Cutina KD], propylene glycol stearate [regin P], cetearyl Alcohol and Sodium cetearyl sulfate [Lanette N, Cutina LE, Crodacol GP], cetearyl alcohol and sodium lauryl sulfate [Lanette W], trilaneth-4 phopshate and glycol stearate and PEG-2 stearate [Sedefos 75], glyceryl stearate and sodium lauryl Sulfate [Teginacid Special]. Cationic acid bases such as cetearyl alcohol and cetrimonium bromide.

The emulsifiers may be used in an amount of, for example, from 1 to 30% by weight, especially from 4 to 20% by weight and preferably from 5 to 10% by weight, based on the total weight of the composition.

When formulated in O/W emulsions, the preferably amount of such emulsifier system could represent 5% to 20% of the oil phase.

Adjuvants and Additives

The cosmetic/pharmaceutical preparations, for example creams, gels, lotions, alcoholic and aqueous/alcoholic solutions, emulsions, wax/fat compositions, stick preparations, powders or ointments, may in addition contain, as further adjuvants and additives, mild surfactants, super-fatting agents, consistency regulators, thickeners, polymers, stabilisers, biogenic active ingredients, deodorising active ingredients, anti-dandruff agents, film formers, swelling agents, further UV light-protective factors, antioxidants, hydrotropic agents, preservatives, insect repellents, self-tanning agents, solubilisers, perfume oils, colourants, bacteria-inhibiting agents and the like.

Super-Fatting Agents

Substances suitable for use as super-fatting agents are, for example, lanolin and lecithin and also polyethoxylated or acrylated lanolin and lecithin derivatives, polyol fatty acid esters, monoglycerides and fatty acid alkanolamides, the latter simultaneously acting as foam stabilisers.

Surfactants

Examples of suitable mild surfactants, that is to say surfactants especially well tolerated by the skin, include fatty alcohol polyglycol ether sulfates, monoglyceride sulfates, mono- and/or di-alkyl sulfosuccinates, fatty acid isethionates, fatty acid sarcosinates, fatty acid taurides, fatty acid glutamates, α-olefin sulfonates, ethercarboxylic acids, alkyl oligoglucosides, fatty acid glucamides, alkylamidobetaines and/or protein fatty acid condensation products, the latter preferably being based on wheat proteins.

Consistency Regulators/Thickeners and Rheology Modifiers

Silicium dioxide, magnesium silicates, aluminium silicates, polysaccharides or derivatives thereof for example hyaluronic acid, xanthan gum, guar-guar, agar-agar, alginates, carra-ghenan, gellan, pectines, or modified cellulose such as hydroxycellulose, hydroxypropyl-methylcellulose. In addition polyacrylates or homopolymer of reticulated acrylic acids and polyacrylamides, carbomer (carbopol types 980, 981, 1382, ETD 2001, ETD2020, Ultrez 10) or Salcare range such as Salcare SC80(steareth-10 allyl ether/acrylates copolymer), Salcare SC81(acrylates copolymer), Salcare SC91 and Salcare AST(sodium acrylates copolymer/PPG-1 trideceth-6), sepigel 305(polyacrylamide/laureth-7), Simulgel NS and Simulgel EG (hydroxyethyl acrylate/sodium acryloyldimethyl taurate copolymer), Stabilen 30 (acrylates/vinyl isodecanoate crosspolymer), Pemulen TR-1(acrylates/C10-30 alkyl acrylate crosspolymer), Luvigel EM (sodium acrylates copolymer), Aculyn 28 (acrylates/beheneth-25 methacrylate copolymer), etc.

Polymers

Suitable cationic polymers are, for example, cationic cellulose derivatives, for example a quatemised hydroxymethyl cellulose obtainable under the name Polymer JR 400 from Amerchol, cationic starches, copolymers of diallylammonium salts and acrylamides, quaternised vinylpyrrolidone/vinyl imidazole polymers, for example Luviquat® (BASF), condensation products of polyglycols and amines, quatemised collagen polypeptides, for example lauryldimonium hydroxypropyl hydrolyzed collagen (Lamequat® L/Grünau), quatemised wheat polypeptides, polyethyleneimine, cationic silicone polymers, for example amidomethicones, copolymers of adipic acid and dimethylaminohydroxypropyldiethylenetriamine (Cartaretin/Sandoz), copolymers of acrylic acid with dimethyldiallylammonium chloride (Merquat 550/Chem-viron), polyaminopolyamides, as described, for example, in FR-A-2 252 840, and the cross-linked water-soluble polymers thereof, cationic chitin derivatives, for example of quatemised chitosan, optionally distributed as microcrystals; condensation products of dihaloalkyls, for example dibromobutane, with bisdialkylamines, for example bisdimethylamino-1,3-propane, cationic guar gum, for example Jaguar C-17, Jaguar C-16 from Celanese, quatemised ammonium salt polymers, for example Mirapol A-15, Mirapol AD-1, Mirapol AZ-1 from Miranol. As anionic, zwitterionic, amphoteric and non-ionic polymers there come into consideration, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, uncrosslinked polyacrylic acids and polyacrylic acids crosslinked with polyols, acrylamidopropyl-trimethylammonium chloride/acrylate copolymers, octyl acrylamide/methyl methacrylatetert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinyl caprolactam terpolymers and also optionally derivatised cellulose ethers and silicones. Furthermore the polymers as described in EP 1093796 (pages 3-8, paragraphs 17-68) may be used.

Biogenic Active Ingredients

Biogenic active ingredients are to be understood as meaning, for example, tocopherol, tocopherol acetate, tocopherol palmitate, ascorbic acid, deoxyribonucleic acid, retinol, bisabolol, allantoin, phytantriol, panthenol, AHA acids, amino acids, ceramides, pseudoceramides, essential oils, plant extracts and vitamin complexes.

Deodorising Active Ingredients

As deodorising active ingredients there come into consideration, for example, anti-perspirants, for example aluminium chlorohydrates (see J. Soc. Cosm. Chem. 24, 281 (1973)). Under the trade mark Locron® of Hoechst AG, Frankfurt (FRG), there is available commercially, for example, an aluminium chlorohydrate corresponding to formula $Al_2(OH)_5Cl\times2.5H_2O$, the use of which is especially preferred (see J. Pharm. Pharmacol. 26, 531 (1975)). Besides the chlorohydrates, it is also possible to use aluminium hydroxyacetates and acidic aluminium/zirconium salts. Esterase inhibitors may be added as further deodorising active ingredients. Such inhibitors are preferably trialkyl citrates, such as trimethyl citrate, tripropyl citrate, triisopropyl citrate, tributyl citrate and especially triethyl citrate (Hydagen CAT, Henkel), which inhibit enzyme activity and hence reduce odour formation. Further substances that come into consideration as esterase inhibitors are sterol sulfates or phosphates, for example lanosterol, cholesterol, campesterol, stigmasterol and sitosterol sulfate or phosphate, dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester and hydroxycarboxylic acids and esters thereof, for example citric acid, malic acid, tartaric acid or tartaric acid diethyl ester. Antibacterial active ingredients that influence the germ flora and kill or inhibit the growth of sweat-decomposing bacteria can likewise be present in the preparations (especially in stick preparations). Examples include chitosan, phenoxyethanol and chlorhexidine gluconate. 5-chloro-2-(2,4-dichlorophenoxy)-phenol (Triclosan, Irgasan, Ciba Specialty Chemicals Inc.) has also proved especially effective.

Anti-Dandruff Agents

As anti-dandruff agents there may be used, for example, dimbazole, octopirox and zinc pyrithione. Customary film formers include, for example, chitosan, microcrystalline chitosan, quaternised chitosan, polyvinylpyrrolidone, vinylpyrrolidone/vinyl acetate copolymers, polymers of quaternary cellulose derivatives containing a high proportion of acrylic acid, collagen, hyaluronic acid and salts thereof and similar compounds.

Antioxidants

In addition to the primary light-protective substances it is also possible to use secondary light-protective substances of the antioxidant kind that interrupt the photochemical reaction chain triggered when UV radiation penetrates the skin or hair. Typical examples of such anti-oxidants are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotinoids, carotenes, lycopene and derivatives thereof, chlorogenic acid and derivatives thereof, lipoic acid and derivatives thereof (e.g. dihydrolipoic acid), aurothioglycose, propylthiouracil and other thiols (e.g. thioredoxin, glutathione, cysteine, cystine, cystamine and the glycosyl, N-acetyl, methyl, ethyl, propyl, amyl, butyl, lauryl, palmitoyl, oleyl, linoleyl, cholesteryl and glyceryl esters thereof) and also salts thereof, dilauryl thiodipropionate, distearyl thiodipropionate, thiodipropionic acid and derivatives thereof (esters, ethers, peptides, lipids, nucleotides, nucleosides and salts) and also sulfoximine compounds (e.g. buthionine sulfoximines, homocysteine sulfoximine, buthionine sulfones, penta-, hexa-, heptathionine sulfoximine), also (metal) chelating agents (e.g. hydroxy fatty acids, palmitic acid phytic acid, lactoferrin), hydroxy acids (e.g. citric acid, lactic acid, malic acid), humic acid, bile acid, bile extracts, bilirubin, biliverdin, EDTA, EDDS, EGTA and derivatives thereof, unsaturated fatty acids and derivatives thereof (e.g. linolenic acid, linoleic acid, oleic acid), folic acid and derivatives thereof, ubiquinone and ubiquinol and derivatives thereof, vitamin C and derivatives (e.g. ascorbyl palmitate, magnesium ascorbyl phosphate, ascorbyl acetate), tocopherols and derivatives (e.g. vitamin E acetate), vitamin A and derivatives (e.g. vitamin A palmitate) and also coniferyl benzoate of benzoin resin, rutinic acid and derivatives thereof, glycosylrutin, ferulic acid, furfurylidene glucitol, carnosine, butyl hydroxytoluene, butyl hydroxyanisole, nordihydroguaiaretic acid, trihydroxybutyrophenone, uric acid and derivatives thereof, mannose and derivatives thereof, superoxide dismutase, N-[3-(3,5-di-tert-butyl-4-hydroxy-phenyl)propionyl]sulfanilic acid (and salts thereof, for example the disodium salts), zinc and derivatives thereof (e.g. ZnO, $ZnSO_4$), selenium and derivatives thereof (e.g. selenium methionine), stilbene and derivatives thereof (e.g. stilbene oxide, trans-stilbene oxide) and the derivatives suitable according to the invention (salts, esters, ethers, sugars, nucleotides, nucleosides, peptides and lipids) of those mentioned active ingredients. HALS (="Hindered Amine Light Stabilizers") compounds may also be mentioned.

Further synthetic and natural antioxidants are listed e.g. in patent WO 0025731: Structures 1-3 (page 2), structure 4 (page 6), structures 5-6 (page 7) and compounds 7-33 (page 8-14).

The amount of antioxidants present is usually from 0.001 to 30% by weight, preferably from 0.01 to 3% by weight, based on the weight of the UV absorber of formula (1).

Hydrotropic Agents

To improve the flow behaviour it is also possible to employ hydrotropic agents, for example ethoxylated or non ethoxylated mono-alcohols, diols or polyols with a low number of carbon atoms or their ethers (e.g. ethanol, isopropanol, 1,2-dipropanediol, propyleneglycol, glyerin, ethylene glycol, ethylene glycol monoethylether, ethylene glycol monobutylether, propylene glycol monomethylether, propylene glycol monoethylether, propylene glycol monobutylether, diethylene glycol monomethylether; diethylene glycol monoethylether, diethylene glycol monobutylether and similar products). The polyols that come into consideration for that purpose have preferably from 2 to 15 carbon atoms and at least two hydroxy groups. The polyols may also contain further functional groups, especially amino groups, and/or may be modified with nitrogen. Typical examples are as follows: glycerol, alkylene glycols, for example ethylene glycol, diethylene glycol, propylene glycol, butylene glycol, hexylene glycol and also polyethylene glycols having an average molecular weight of from 100 to 1000 Dalton; technical oligoglycerol mixtures having an intrinsic degree of condensation of from 1.5 to 10, for example technical diglycerol mixtures having a diglycerol content of from 40 to 50% by weight; methylol compounds, such as, especially, trimethylolethane, trimethylolpropane, trimethylolbutane, pentaerythritol and dipentaerythritol; lower alkyl-glucosides, especially those having from 1 to 8 carbon atoms in the alkyl radical, for example methyl and butyl glucoside; sugar alcohols having from 5 to 12 carbon atoms, for example sorbitol or mannitol; sugars having from 5 to 12 carbon atoms, for example glucose or saccharose; amino sugars, for example glucamine; dialcohol amines, such as diethanolamine or 2-amino-1,3-propanediol.

Preservatives and Bacteria-Inhibiting Agents

Suitable preservatives include, for example, Methyl-, Ethyl-, Propyl-, Butyl-parabens, Benzalkonium chloride, 2-Bromo-2-nitro-propane-1,3-diol, Dehydroacetic acid, Diazolidinyl Urea, 2-Dichloro-benzyl alcohol, DMDM hydantoin, Formaldehyde solution, Methyldibromoglutanitrile, Phenoxyethanol, Sodium Hydroxymethylglycinate, Imidazolidinyl Urea, Triclosan and further substance classes listed in the following reference: K. F. DePolo—A short textbook of cosmetology, Chapter 7, Table 7-2, 7-3, 7-4 and 7-5, p210-219.

Bacteria-Inhibiting Agents

Typical examples of bacteria-inhibiting agents are preservatives that have a specific action against gram-positive bacteria, such as 2,4,4'-trichloro-2'-hydroxydiphenyl ether, chlorhexidine (1,6-di(4-chlorophenyl-biguanido)hexane) or TCC (3,4,4'-trichlorocarbanilide). A large number of aromatic substances and ethereal oils also have antimicrobial properties. Typical examples are the active ingredients eugenol, menthol and thymol in clove oil, mint oil and thyme oil. A natural deodorising agent of interest is the terpene alcohol farnesol (3,7,11-trimethyl-2,6,10-dodecatrien-1-ol), which is present in lime blossom oil. Glycerol monolaurate has also proved to be a bacteriostatic agent. The amount of the additional bacteria-inhibiting agents present is usually from 0.1 to 2% by weight, based on the solids content of the preparations.

Perfume Oils

There may be mentioned as perfume oils mixtures of natural and/or synthetic aromatic substances. Natural aromatic substances are, for example, extracts from blossom (lilies, lavender, roses, jasmine, neroli, ylang-ylang), from stems and leaves (geranium, patchouli, petitgrain), from fruit (aniseed, coriander, carraway, juniper), from fruit peel (bergamot, lemons, oranges), from roots (mace, angelica, celery, cardamom, costus, iris, calmus), from wood (pinewood, sandalwood, guaiacum wood, cedarwood, rosewood), from herbs and grasses (tarragon, lemon grass, sage, thyme), from needles and twigs (spruce, pine, Scots pine, mountain pine), from resins and balsams (galbanum, elemi, benzoin, myrrh, olibanum, opoponax). Animal raw materials also come into consideration, for example civet and castoreum. Typical synthetic aromatic substances are, for example, products of the ester, ether, aldehyde, ketone, alcohol or hydrocarbon type. Aromatic substance compounds of the ester type are, for example, benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate and benzyl salicylate. The ethers include, for example, benzyl ethyl ether; the aldehydes include, for example, the linear alkanals having from 8 to 18 hydrocarbon atoms, citral, citronellal, citronellyl oxyacetaldehyde, cyclamen aldehyde, hydroxycitronellal, lilial and bourgeonal; the ketones include, for example, the ionones, isomethylionone and methyl cedryl ketone; the alcohols include, for example, anethol, citronellol, eugenol, isoeugenol, geraniol, linalool, phenyl ethyl alcohol and terpinol; and the hydrocarbons include mainly the terpenes and balsams. It is preferable, however, to use mixtures of various aromatic substances that together produce an attractive scent. Ethereal oils of relatively low volatility, which are chiefly used as aroma components, are also suitable as perfume oils, e.g. sage oil, camomile oil, clove oil, melissa oil, oil of cinnamon leaves, lime blossom oil, juniper berry oil, vetiver oil, olibanum oil, galbanum oil, labolanum oil and lavandin oil. Preference is given to the use of bergamot oil, dihydromyrcenol, lilial, lyral, citronellol, phenyl ethyl alcohol, hexyl cinnamaldehyde, geraniol, benzyl acetone, cyclamen aldehyde, linalool, boisambrene forte, ambroxan, indole, hedione, sandelice, lemon oil, tangerine oil, orange oil, allyl amyl glycolate, cyclovertal, lavandin oil, muscatel sage oil, damascone, bourbon geranium oil, cyclohexyl salicylate, vertofix coeur, iso-E-Super, Fixolide NP, evemyl, iraldein gamma, phenylacetic acid, geranyl acetate, benzyl acetate, rose oxide, romillat, irotyl and floramat alone or in admixture with one another.

Colourants

There may be used as colourants the substances that are suitable and permitted for cosmetic purposes, as compiled, for example, in the publication "Kosmetische Färbemittel" of the Farbstoffkommission der Deutschen Forschungsgemeinschaft, Verlag Chemie, Weinheim, 1984, pages 81 to 106. The colourants are usually used in concentrations of from 0.001 to 0.1% by weight, based on the total mixture.

Polymeric Beads or Hollow Spheres as SPF Enhancers

The combination of the UV-absorbers and UV-absorber combinations, listed above, with SPF enhancers, such as non-active ingredients like Styrene/acrylates copolymer, silica beads, spheroidal magnesium silicate, crosslinked Polymethylmethacrylates (PMMA; Micopearl M305 Seppic), can maximize better the UV protection of the sun products. Holosphere additives (Sunspheres® ISP, Silica Shells Kobo.) deflect radiation and the effective path length of the photon is therefore increased.(EP0893119). Some beads, as mentioned previously, provide a soft feel during spreading. Moreover, the optical activity of such beads, e.g.Micropearl M305, cans modulate skin shine by eliminating reflection phenomena and indirectly may scatter the UV light.

Other Adjuvants alpha glucosylrutin (CAS No. 130603-71-3), 2-butyloctyl o-hydroxybenzoate (CAS No. 190085-41-7), vitamin E (CAS No. 1406-18-4), vitamin E acetate (CAS No. 58-95-7), diethyl hexyl 2,6-naphthalate, di-n-butyl adipate, di(2-ethylhexyl)-adipate, di(2-ethylhexyl)-succinate and diisotridecyl acelaat, and also diol esters, such as ethylene glycol dioleate, ethylene glycol diisotridecanoate, propylene glycol di(2-ethylhexanoate), propylene glycol diisostearate, propylene glycol dipelargonate, butanediol diisostearate and neopentyl glycol dicaprylate. Esters of $C_6$-$C_{24}$ fatty alcohols and/or Guerbet alcohols with aromatic carboxylic acids, saturated and/or unsaturated, especially benzoic acid, esters of $C_2$-$C_{12}$dicarboxylic acids with linear or branched alcohols having from 1 to 22 carbon atoms or polyols having from 2 to 10 carbon atoms and from 2 to 6 hydroxy groups, or iminodisuccinic acid and imiondisuccinic acid salts [CAS 7408-20-0] or latex particles, aloe vera, chamomile, ginko biloba, ginseng, coenzyme Q10, *laminaria ochroleuca* extract, *magnolia oborata* extract, *melalenca altemifolia* leaf oil, *rubus idaeus* seed oil, *vaccinium macrocarpon* seed oil, pumpkin seed extract, pumpkin seed oil, grape seed extract, carnosine, alpha-arbutin, madecassoside, termino-laside, tetrahydrocurcuminoids (THC), mycosporines, mycosporine like amino acids from the red alga *porphyra umbilicalis*, mycosporine-like amino acids (as described in WO2002039974), cis-9-octadecenedioic acid, lipoic acid, laurimino dipropiomic acid tocopheryl phosphates (LDTP), microcrystalline cellulose (MCC), polycarbonates as described in WO 0341676, sterols (cholesterol, lanosterol, phytosterols), as described in WO0341675 and linear poly-alpha-glucans as described in U.S. Pat. No. 6,616,935

Cosmetic or Pharmaceutical Preparations

Cosmetic or pharmaceutical formulations are contained in a wide variety of cosmetic preparations. There come into consideration, for example, especially the following preparations:

skin-care preparations, e.g. skin-washing and cleansing preparations in the form of tablet-form or liquid soaps, soapless detergents or washing pastes, bath preparations, e.g. liquid (foam baths, milks, shower preparations) or solid bath preparations, e.g. bath cubes and bath salts;

skin-care preparations, e.g. skin emulsions, multi-emulsions or skin oils;

cosmetic personal care preparations, e.g. facial make-up in the form of day creams or powder creams, face powder (loose or pressed), rouge or cream make-up, eye-care preparations, e.g. eyeshadow preparations, mascara, eyeliner, eye creams or eye-fix creams; lip-care preparations, e.g. lipsticks, lip gloss, lip contour pencils, nail-care preparations, such as nail varnish, nail varnish removers, nail hardeners or cuticle removers;

foot-care preparations, e.g. foot baths, foot powders, foot creams or foot balsams, special deodorants and antiperspirants or callus-removing preparations;

light-protective preparations, such as sun milks, lotions, creams or oils, sunblocks or tropicals, pre-tanning preparations or after-sun preparations;

skin-tanning preparations, e.g. self-tanning creams;

depigmenting preparations, e.g. preparations for bleaching the skin or skin-lightening preparations;

insect-repellents, e.g. insect-repellent oils, lotions, sprays or sticks;

deodorants, such as deodorant sprays, pump-action sprays, deodorant gels, sticks or roll-ons;

antiperspirants, e.g. antiperspirant sticks, creams or roll-ons;

preparations for cleansing and caring for blemished skin, e.g. synthetic detergents (solid or liquid), peeling or scrub preparations or peeling masks;

hair-removal preparations in chemical form (depilation), e.g. hair-removing powders, liquid hair-removing preparations, cream- or paste-form hair-removing preparations, hair-removing preparations in gel form or aerosol foams;

shaving preparations, e.g. shaving soap, foaming shaving creams, non-foaming shaving creams, foams and gels, preshave preparations for dry shaving, aftershaves or aftershave lotions;

fragrance preparations, e.g. fragrances (eau de Cologne, eau de toilette, eau de parfum, parfum de toilette, perfume), perfume oils or perfume creams;

cosmetic hair-treatment preparations, e.g. hair-washing preparations in the form of shampoos and conditioners, hair-care preparations, e.g. pretreatment preparations, hair tonics, styling creams, styling gels, pomades, hair rinses, treatment packs, intensive hair treatments, hair-structuring preparations, e.g. hair-waving preparations for permanent waves (hot wave, mild wave, cold wave), hair-straightening preparations, liquid hair-setting preparations, hair foams, hairsprays, bleaching preparations, e.g. hydrogen peroxide solutions, lightening shampoos, bleaching creams, bleaching powders, bleaching pastes or oils, temporary, semi-permanent or permanent hair colourants, preparations containing self-oxidising dyes, or natural hair colourants, such as henna or camomile.

Presentation Forms

The final formulations listed may exist in a wide variety of presentation forms, for example:

in the form of liquid preparations as a W/O, O/W, O/W/O, W/O/W or PIT emulsion and all kinds of microemulsions, in the form of a gel, in the form of an oil, a cream, milk or lotion, in the form of a powder, a lacquer, a tablet or make-up, in the form of a stick, in the form of a spray (spray with propellent gas or pump-action spray) or an aerosol, in the form of a foam, or in the form of a paste.

Of special importance as cosmetic preparations for the skin are light-protective preparations, such as sun milks, lotions, creams, oils, sunblocks or tropicals, pretanning preparations or after-sun preparations, also skin-tanning preparations, for example self-tanning creams. Of particular interest are sun protection creams, sun protection lotions, sun protection milk and sun protection preparations in the form of a spray.

Of special importance as cosmetic preparations for the hair are the above-mentioned preparations for hair treatment, especially hair-washing preparations in the form of shampoos, hair conditioners, hair-care preparations, e.g. pretreatment preparations, hair tonics, styling creams, styling gels, pomades, hair rinses, treatment packs, intensive hair treatments, hair-straightening preparations, liquid hair-setting preparations, hair foams and hairsprays. Of special interest are hair-washing preparations in the form of shampoos.

A shampoo has, for example, the following composition: from 0.01 to 5% by weight of a UV absorber according to the invention, 12.0% by weight of sodium laureth-2-sulfate, 4.0% by weight of cocamidopropyl betaine, 3.0% by weight of sodium chloride, and water ad 100%.

For example, especially the following hair-cosmetic formulations may be used:

a$_1$) spontaneously emulsifying stock formulation, consisting of the UV absorber according to the invention, PEG-6-C$_{10}$oxoalcohol and sorbitan sesquioleate, to which water and any desired quaternary ammonium compound, for example 4% minkamidopropyl dimethyl-2-hydroxyethylammonium chloride or Quaternium 80 is added;

a$_2$) spontaneously emulsifying stock formulation consisting of the UV absorber according to the invention, tributyl citrate and PEG-20-sorbitan monooleate, to which water and any desired quaternary ammonium compound, for example 4% minkamidopropyl dimethyl-2-hydroxyethylammonium chloride or Quaternium 80 is added;

b) quat-doped solutions of the UV absorber according to the invention in butyl triglycol and tributyl citrate;

c) mixtures or solutions of the UV absorber according to the invention with n-alkylpyrrolidone.

Other typical ingredients in such formulations are preservatives, bactericides and bacteriostatic agents, perfumes, dyes, pigments, thickening agents, moisturizing agents, humectants, fats, oils, waxes or other typical ingredients of cosmetic and personal care formulations such as alcohols, poly-alcohols, polymers, electrolytes, organic solvents, silicon derivatives, emollients, emulsifiers or emulsifying surfactants, surfactants, dispersing agents, antioxidants, anti-irritants and anti-inflammatory agents etc.

Examples of Cosmetic and Pharmaceutical Preparations (X=Preferred Combinations)

| O/W systems: | | | | | | | | |
|---|---|---|---|---|---|---|---|---|
| Ingredients | 1 | 2 | 3 | 4 | 5 | 6 | 7 | 8 |
| Emulsifiers | | | | | | | | |
| Potassium Cetyl Phosphate 2%-5% | X | | | | | | | |
| Cetearyl Alcohol/Dicetyl Phosphate/Ceteth-10 Phosphate 2%-6% | | X | | | | | | |
| Sodium Stearyl Phtalamate 1%-2% | | | X | | | | | |
| Cetearyl Alcohol/Behentrimonium Methosulfate 1%-5% | | | | X | | | | |
| Quaternium-32 1%-5% | | | | | X | | | |
| Dimethicone copolyol/Caprylic/Capric Triglyceride (1%-4%) | | | | | | X | | |
| Steareth-2/Steareth-21 2%-5% | | | | | | | X | |
| Polyglyceryl Methyl Glucose Distearate 1%-4% | | | | | | | | X |
| Lipophilic emollient/dispersant oil 15%-20% | X | X | X | X | X | X | X | X |
| Fatty Alcohols and/or Waxes 1%-5% | X | X | X | X | X | X | X | X |
| Thickeners (water swellable thickeners) 0.5%-1.5% | X | X | X | X | X | X | X | X |
| Preservatives 0.5%-1% | X | X | X | X | X | X | X | X |
| Chelating agents (such as EDTA) 0%-0.2% | X | X | X | X | X | X | X | X |
| Antioxidants 0.05%-0.2% | X | X | X | X | X | X | X | X |
| Water deionized Qs 100% | X | X | X | X | X | X | X | X |
| Perfume oils 0.1%-0.4% | X | X | X | X | X | X | X | X |
| UV-absorber according to the invention 0.1%-20% | X | X | X | X | X | X | X | X |
| UV-absorber as described in table 1-3 0%-30% | X | X | X | X | X | X | X | X |

| W/O systems | | | | | |
|---|---|---|---|---|---|
| Ingredients | 1 | 2 | 3 | 4 | 5 |
| Emulsifiers | X | X | X | X | X |
| Polyglyceryl-2 Dipolyhydroxystearate 2%-4% | X | X | X | X | X |
| PEG-30 Dipolyhydroxystearate 2%-4% | | X | | | |
| Rapeseed Oil Sorbitol Esters 1%-5% | | | X | | |
| PEG-45/Dodecyl Glycol Copolymer 1%-5% | | | | X | |
| Sorbitan Oleate/Polycerol-3 ricinoleate 1%-5% | | | | | X |
| Lipophilic emollient/dispersant oil 10%-20% | X | X | X | X | X |
| Fatty Alcohols and/or Waxes 10%-15% | X | X | X | X | X |
| Electrolytes (NaCl, MgSO$_4$) 0.5%-1% | X | X | X | X | X |
| Polyol phase (Propylene glycol, glycerin) 1%-8% | X | X | X | X | X |
| Preservatives 0.3%-0.8% | X | X | X | X | X |
| Perfume oils 0.1%-0.4% | X | X | X | X | X |
| Chelating agents (such as EDTA) 0%-0.2% | X | X | X | X | X |
| Antioxidants 0.05%-0.2% | X | X | X | X | X |
| Water deionized Qs 100% | X | X | X | X | X |
| UV-absorber according to the invention 0.1%-20%. | X | X | X | X | X |
| UV-absorber as described in table 1-3 0%-30%. | X | X | X | X | X |

| W/Silicone systems | | | | |
|---|---|---|---|---|
| Ingredients | 1 | 2 | 3 | 4 |
| Dimethicone Copolyol/Cyclomethicone 5%-10% | X | | X | |
| Laurylmethicone Copolyol 5%-10% | | X | | X |
| Cyclopentasiloxane 15%-25% | X | | | X |
| Dimethicone 15%-25% | | | X | X |
| Dimethicone/Vinyldimethicone Crosspolymer 1%-10% | X | X | X | X |

W/Silicone systems -continued

| Ingredients | 1 | 2 | 3 | 4 |
|---|---|---|---|---|
| Humectant/polyols (Propylene glycol, glycerin . . . ) 2%-8% | X | X | X | X |
| Chelating agents (such as EDTA) 0%-0.2% | X | X | X | X |
| Antioxidants 0.05%-0.2% | X | X | X | X |
| Preservatives 0.3%-0.8% | X | X | X | X |
| Perfume oils 0.1%-0.4% | X | X | X | X |
| Water deionized Qs 100% | X | X | X | X |
| UV-absorber according to the invention 0.1%-20% | X | X | X | X |
| UV-absorber as described in table 1-3 0%-30% | X | X | X | X |

O1/W/O2 emulsions -continued

| Ingredients | 1 | 2 | 3 | 4 | 5 | 6 | 7 | 8 |
|---|---|---|---|---|---|---|---|---|
| Silicone oils |  |  |  |  |  | X |  | X |
| Preservatives 0.3%-0.8% | X | X | X | X | X | X | X | X |
| Water deionized Qs 100% | X | X | X | X | X | X | X | X |
| Non ionic multifunctional W/O emulsifier 2%-5% | X | X | X | X | X | X | X | X |
| Waxes 1%-5% | X | X | X | X | X | X | X | X |
| Oil phase 20%-30% | X | X | X | X | X | X | X | X |
| Silicone oils |  |  |  |  |  |  |  |  |
| Primary emulsion O1/W 15% | X | X | X | X | X | X | X |  |

Multiple emulsions

| Ingredients | 1 | 2 | 3 | 4 | 5 | 6 | 7 | 8 | 9 | 10 | 11 | 12 |
|---|---|---|---|---|---|---|---|---|---|---|---|---|
| PEG-30 Dipolyhydroxystearate (2%-6%) | X |  |  |  |  |  |  |  |  | X | X |  |
| Cetyl Dimethicone Copolyol 1%-3% |  | X |  |  |  |  |  |  | X |  |  |  |
| PEG-30 Dipolyhydroxystearate/ Steareth-2/Steareth-21 4%-6% |  |  | X |  |  |  |  | X |  |  |  |  |
| Polyglyceryl-2 Dipolyhydroxy-stearate 1%-3% |  |  |  | X |  |  | X |  |  |  |  |  |
| Polyglyceryl-6 Ricinoleate 1%-3% |  |  |  |  | X | X |  |  |  |  | X |  |
| Oil phase 15%-30% |  |  |  |  |  |  |  |  |  |  |  |  |
| Fatty acid esters | X | X | X | X | X |  |  |  |  |  | X | X |
| Natural and synthetic Triglycerides |  |  |  |  |  | X | X | X | X | X | X | X |
| Hydrocarbon oils | X | X | X | X | X |  |  |  |  |  | X | X |
| Silicone oils |  |  |  |  |  | X | X | X | X | X | X | X |
| Preservatives 0.3%-0.8% | X | X | X | X | X | X | X | X | X | X | X | X |
| Water Deioniz. qs 100% | X | X | X | X | X | X | X | X | X | X | X | X |
| Sorbitan Stearate/Sucrose Cocoate 3%-7% | X |  |  |  |  |  |  | X |  |  |  | X |
| Sucrose Laurate 3%-7% |  | X |  |  |  |  |  | X |  |  | X |  |
| Lauryl sarcosinate (as described in FR 2 796 550) | x |  | x | x | x |  | x |  |  | x | x | x |
| Poloxamer 407 3%-7% |  |  | X |  |  | X |  |  | X |  |  |  |
| Polyoxyethylene(20)Sorbate Monoleate 3%-5% |  |  |  | X | X |  |  |  |  | X |  |  |
| Primary emulsion W1/O 50% | X | X | X | X | X | X | X | X | X | X | X | X |
| Thickeners (water swellable polymers) 0.3%-1% | X | X | X | X | X | X | X | X | X | X | X | X |
| Water deionized Qs 100% | X | X | X | X | X | X | X | X | X | X | X | X |
| Perfume oils 0.1%-0.4% | X | X | X | X | X | X | X | X | X | X | X | X |
| UV-absorber according to the invention 0.1%-20% | X | X | X | X | X | X | X | X | X | X | X | X |
| UV-absorber as described in table 1-3 0%-30% | X | X | X | X | X | X | X | X | X | X | X | X |

O1/W/O2 emulsions

| Ingredients | 1 | 2 | 3 | 4 | 5 | 6 | 7 | 8 |
|---|---|---|---|---|---|---|---|---|
| Primary emulsion O1/W |  |  |  |  |  |  |  |  |
| PEG-60 Hydrogenated Castor Oil 25% | X |  |  | X | X |  |  | X |
| Steareth-25 25% |  | X | X |  |  | X | X |  |
| Oil phase 75% |  |  |  |  |  |  |  |  |
| Fatty acid esters | X |  | X |  |  |  |  |  |
| Natural and synthetic Triglycerides |  | X |  | X |  |  |  |  |
| Hydrocarbon oils |  |  |  |  |  | X |  | X |

O1/W/O2 emulsions -continued

| Ingredients | 1 | 2 | 3 | 4 | 5 | 6 | 7 | 8 |
|---|---|---|---|---|---|---|---|---|
| Electrolytes (NaCl, MgSO$_4$) 0.1%-0.5% | X | X | X | X | X | X | X | X |
| Water deionized Qs 100% | X | X | X | X | X | X | X | X |
| Perfume oils 0.1%-0.4% | X | X | X | X | X | X | X | X |
| UV-absorber according to the invention 0.1%-20% | X | X | X | X | X | X | X | X |
| UV-absorber as described in table 1-3 0%-30% | X | X | X | X | X | X | X | X |

| Microemulsions | | | | | | | | | | |
|---|---|---|---|---|---|---|---|---|---|---|
| Ingredients | 1 | 2 | 3 | 4 | 5 | 6 | 7 | 8 | 9 | 10 |
| PEG-8 Caprylic/Capric Glycerides 10%-25% | X | | | X | X | | | X | X | |
| PPG-5-ceteth-20 10%-25% | | X | X | | | X | X | | | X |
| Polyglyceryl-6 Isostearate 5%-15% | X | | X | | | | | | | |
| Polyglyceryl-3 Diisostearate 5%-15% | | X | | X | | | | | | |
| Polyglyceryl-6 Dioleate 5%-15% | | | | | X | | X | | | |
| PPG-10 Cetyl Ether 5%-15% | | | | | | X | | X | | |
| Ethoxydiglycol 5%-15% | | | | | | | | | X | X |
| Oil phase 10%-80% | X | X | X | X | X | X | X | X | X | X |
| Isostearyl Benzoate | X | X | X | X | X | X | X | X | X | X |
| Isostearyl Isostearate | X | X | X | X | X | X | X | X | X | X |
| PEG-7 Glyceryl Cocoate | X | X | X | X | X | X | X | X | X | X |
| Cyclomethicone | X | X | X | X | X | X | X | X | X | X |
| Polyalcohols/Humectants 1%-10% | X | X | X | X | X | X | X | X | X | X |
| Preservatives 0.3-0.8% | X | X | X | X | X | X | X | X | X | X |
| Perfume oils 0.1%-0.4% | X | X | X | X | X | X | X | X | X | X |
| Water Deioniz. qs 100% | X | X | X | X | X | X | X | X | X | X |
| UV-absorber according to the invention 0.1%-20% | X | X | X | X | X | X | X | X | X | X |
| UV-absorber as described in table 1-3 0%-30% | X | X | X | X | X | X | X | X | X | X |

| O/W Spray emulsions | | | | | | |
|---|---|---|---|---|---|---|
| Ingredients | 1 | 2 | 3 | 4 | 5 | 6 |
| Alkyl Phosphates 0.1%-5% | X | | | X | X | |
| Glucosidic derivatives 0.1%-5% | | X | X | | | X |
| Solubilisants | | | | | | |
| Ethoxylated Glyceryl ethers 0.1%-1% | X | | X | | | |
| Polysorbates 0.1%-1% | | X | | X | | |
| Ethoxylated Oleyl ethers 0.1%-1% | | | | | X | X |
| PVP/VA Coplymer 1%-10% | X | | X | | X | |
| PVM/MA Copolymer 1%-10% | | X | | X | | X |
| Oil phase 5%-20% | X | X | X | X | X | X |
| Natural oils (Meadowfoam, Jojoba, Macadamia . . . ) | X | X | X | X | X | X |
| Fatty acids esters | X | X | X | X | X | X |
| Mineral oils | X | X | X | X | X | X |
| Silicone oils | X | X | X | X | X | X |
| Alcohol 0%-50% | X | X | X | X | X | X |
| Thickeners 0.1%-0.5% | X | X | X | X | X | X |
| Polyacrylates | X | X | X | X | X | X |
| Aluminium/Magnesium Silicates | X | X | X | X | X | X |
| Gums | X | X | X | X | X | X |
| Neutralizing agents 0%-1% | X | X | X | X | X | X |
| Polyalcohols/Humectants 1%-5% | X | X | X | X | X | X |
| Chelating agents (such as EDTA) 0%-0.2% | X | X | X | X | X | X |
| Antioxidants 0.05%-0.2% | X | X | X | X | X | X |
| Water Deioniz. qs 100% | X | X | X | X | X | X |
| Perfume oils 0.1%-0.5% | X | X | X | X | X | X |
| Preservatives 0.4%-1% | X | X | X | X | X | X |
| UV-absorber according to the invention 0.1%-20% | X | X | X | X | X | X |
| UV-absorber as described in table 1-3 0%-30% | X | X | X | X | X | X |

| G - Aqueous | | | | | | | | | | | | |
|---|---|---|---|---|---|---|---|---|---|---|---|---|
| Ingredients | 1 | 2 | 3 | 4 | 5 | 6 | 7 | 8 | 9 | 10 | 11 | 12 |
| Thickeners | | | | | | | | | | | | |
| Natural Thickener 1%-5% | X | | | | X | X | | | | | | X |
| Semi-synthetic Thickener 1%-5% | | X | | X | | | X | | X | | | |
| Synthetic Thickener 0.3%-1.3% | | | X | X | | | | X | X | | | |
| Neutralizing Agents 0.5%-1.5% | X | X | X | X | X | X | X | X | X | X | X | X |
| Polyols - Humectants 5%-50% | X | X | X | X | X | X | X | X | X | X | X | X |
| Polyquaternium series 1%-5% | X | X | X | | | | X | X | X | | | |
| PVM/MA Copolymer 1%-5% | | | | X | X | X | | | | X | X | X |
| Preservatives 0.5%-1% | X | X | X | X | X | X | X | X | X | X | X | X |
| Chelating Agents (as EDTA) <0.1% | X | X | X | X | X | X | X | X | X | X | X | X |
| Water Deioniz. qs 100% | X | X | X | X | X | X | X | X | X | X | X | X |
| Perfume oils 0.05%-0.4% | X | X | X | X | X | X | X | X | X | X | X | X |
| Ethoxylated Glyceryl ethers 0.1%-5% | X | X | X | | | | | | | | | |
| Polysorbates 0.1%-5% | | | | X | X | X | | | | | | |
| Ethoxylated Oleyl ethers 0.1%-5% | | | | | | | X | X | X | X | X | X |

-continued

| G - Aqueous | | | | | | | | | | | | |
|---|---|---|---|---|---|---|---|---|---|---|---|---|
| Ingredients | 1 | 2 | 3 | 4 | 5 | 6 | 7 | 8 | 9 | 10 | 11 | 12 |
| UV-absorber according to the invention 0.1%-20% | X | X | X | X | X | X | X | X | X | X | X | X |
| UV-absorber as described in table 1-3 0%-30% | X | X | X | X | X | X | X | X | X | X | X | X |

| Oleogels | | | | | | | | | | | |
|---|---|---|---|---|---|---|---|---|---|---|---|
| Ingredients | 1 | 2 | 3 | 4 | 5 | 6 | 7 | 8 | 9 | 10 |
| Hydrogenated Lecithin 1%-10% | X | | | | | | | | | X |
| Silica Dimethyl Silylate 1%-10% | | X | | | | | | | X | |
| Silica 1%-5% | | | X | | | | | X | | |
| $C_{24-28}$ Alkyl Dimethicone 1%-5% | | | | X | | | X | | | |
| Aluminium or Magnesium Stearate 1%-5% | | | | | X | X | | | | |
| Polyols - Humectants 5%-70% | X | X | X | X | X | X | X | X | X | X |
| Oil phase 20%-90% | | | | | | | | | | |
| Dicaprylyl Ether | X | | | | | X | | X | | |
| Phenyl Trimethicone | | X | | | | | | X | | |
| Hydrogenated Polyisobutene | | | | X | | | | | | |
| Isopropyl Isostearate | | | | | X | | | | X | |
| Oleogel basis (Mineral oil and hydrogenated Butylene/Ethylene or Ethylene/Propylene Styrene Copolymer) | | | | | | X | | | | X |
| Silicone wax 1%-10% | X | X | X | X | X | X | X | X | X | X |
| Dimethiconol Behenate | X | X | X | X | X | X | X | X | X | X |
| Dimethiconol Stearate | X | X | X | X | X | X | X | X | X | X |
| Perfume oils 0.1%-0.5% | X | X | X | X | X | X | X | X | X | X |
| Antioxidants 0.05%-0.2% | X | X | X | X | X | X | X | X | X | X |
| UV-absorber according to the invention 0.1%-20% | X | X | X | X | X | X | X | X | X | X |
| UV-absorber as described in table 1-3 0%-30%) | X | X | X | X | X | X | X | X | X | X |

| Light/dry cosmetic oils | | | | |
|---|---|---|---|---|
| Ingredients | 1 | 2 | 3 | 4 |
| Hydrocarbon oils 30%-70% | X | | | X |
| Fatty acid esters branched or not 10%-50% | | X | X | |
| Silicones/Siloxanes 0%-10% | X | | | X |
| Perfluorinated oils and Perfluoroethers 0%-10% | | X | | X |
| Viscosifying agents 0%-10% | X | X | X | X |
| Esters of long chain acids and alcohols 0%-2% | X | X | X | X |
| Antioxidants 0.1-1% | X | X | X | X |
| Solubilisants/dispersing agents 0%-5% | X | X | X | X |
| Perfume oils 0.1%-0.5% | X | X | X | X |
| UV-absorber according to the invention 0.1%-20%. | X | X | X | X |
| UV-absorber as described in table 1-3 0%-30% | X | X | X | X |

| Foaming/mousse products | |
|---|---|
| Ingredients | 1 |
| SD Alcohol 40 0%-8% | X |
| Propellant 8%-15% | X |
| Nonionic Emulsifier/Surfactant 0.5%-3% | X |
| Corrosion Inhibitor 0%-1% | X |
| Perfume oils 0.1%-0.5% | X |
| Preservatives 0.1%-1% | X |
| Miscellaneous 0%-1% | X |

-continued

| Foaming/mousse products | |
|---|---|
| Ingredients | 1 |
| UV-absorber according to the invention 0.1%-20%. | X |
| UV-absorber as described in table 1-3 0%-30% | X |

| Stick products | |
|---|---|
| Ingredients | 1 |
| Waxes 15%-30% | X |
| Natural and silicone oils 20%-75% | X |
| Lanoline derivatives 5%->50% | X |
| Esters of lanolin | x |
| Acetylated lanolin | x |
| Lanolin oil | x |
| Colorants and pigments 10%-15% | X |
| Antioxidants 0.1%-0.8% | X |
| Perfume oils 0.1%-2% | X |
| Preservatives 0.1%-0.7% | X |
| UV-absorber according to the invention 0.1%-20% | X |
| UV-absorber as described in table 1-3 0%-30% | X |

| Liquid and compact | | |
|---|---|---|
| Ingredients | 1 | 2 |
| Liquid foundation | | |
| Powder phase 10%-15% | X | |
| Oil phase 30%-40%; 75% (only for anhydrous form) | X | |
| Thickener/suspending agents1%-5% | X | |
| Film forming polymers 1%-2% | X | |
| Antioxidants 0.1%-1% | X | |
| Perfume oils 0.1%-0.5% | X | |
| Preservatives 0.1%-0.8% | X | |
| Water deionized Qs 100% | X | |
| Compact powder | | |
| Powder phase 15%-50% | | X |
| Oil phase 15%-50% | | X |
| Polyol phase 5%-15% | | X |
| Antioxidants 0.1%-1% | | X |
| Perfume oils 0.1%-0.5% | | X |
| Preservatives 0.1%-0.8% | | X |
| For the two product forms | | |
| UV-absorber according to the invention 0.1%-20% | X | X |
| UV-absorber as described in table 1-3 0%-30% | X | X |

| Conditioning Shampoos | |
|---|---|
| Ingredients | 1 |
| Primary surfactants (listed previously) 5%-10% | X |
| Secondary surfactants (listed previously) 5%-15% | X |
| Foam Stabilizers (listed previously) 0%-5% | X |
| Water deionized 40%-70% | X |
| Actives 0-10% | X |
| Conditioners | x |
| Refatting agents | x |
| Moisturizing agents | x |
| Thickeners/Rheology mofifiers 0%-3% | X |
| Humectants 0%-2% | X |
| PH adjusting agents 0%-1% | X |
| Preservatives 0.05%-1% | X |
| Perfume oils 0.1%-1% | X |
| Antioxidants 0.05%-0.20% | X |
| Chelating Agents (EDTA) 0%-0.2% | X |
| Opascifying agents 0%-2% | X |
| UV-absorber according to the invention 0.1%-20% | X |
| UV-absorber as described in table 1-3 0%-30% | X |

The cosmetic preparation according to the invention is distinguished by excellent protection of human skin against the damaging effect of sunlight.

The naphthalene amidine amides according to the present invention may also be used for different purposes:
- as pigments: for example in glue-bound distempers like watercolors and colors for ink-jet-printers and other colors for painting; in lacquers like acryl- or vinylresins, polyester lacquers, novolacquers or natural materials like cellulose lacquers.
- as fluorescent dyes: for example for labeling of devices for mechanical recognition of these devices; in anylytics, in szintillators, in optical lightcollecting systems, in fluorescence-solar-collectors, in fluorescent-active devices, for testing materials, for investigation of mixro structures of integrated semiconductor devices, in photoconductors, in fotogaric procedures, in chemiluminescence systems in signal colors;
- for decorative purposes;
- in data storage units;
- in illuminating diodes;
- in photovoltaic devices;
- for internal dyeing of polymers;
- as vat dyes;
- for dyeing of natural materials;
- for security labelling;
- for labeling of devices for mechanical recognition of these devices;
- for light frequency translation;
- as starting material for superconductive materials;
- for tracer purposes;
- as dyes in color lasers as Q-Switcher;
- as active for non-linear optics.
- as rheology enhancer.
- for leakage test in a closed circuit.

EXAMPLES

Example 1

Preparation of a Micronized UV Absorber 100 parts of the compound of formula (7a), (7b), or (7d) respectively are milled together with zirconium silicate bells (diameter: 0.1 to 4 mm) as grinding aids, a dispersing agent (15 parts of $C_8$-$C_{16}$polyglucoside) and water (85 parts) in a ball mill to a mean particle size of $d_{50}$=130 nm.

With this method a micropigment dispersion of a UV absorber is obtained.

Example 2

Preparation of a Micronized UV Absorber 100 parts of the compound of formula (7a), (7b), or (7d) respectively are milled together with zirconium silicate bells (diameter: 0.1 to 4 mm) as grinding aids, a dispersing agent (15 parts $C_{12}$gyceride-PEG10) and water (85 parts) in a ball mill to a mean particle size of $d_{50}$=130 nm.

With this method a micropigment dispersion of a UV absorber is obtained.

According to example 1 additional micropigment dispersions are prepared:

Example 3

| | Sparingly soluble micronized substance | Dispersing agent | water | Thickening agent |
|---|---|---|---|---|
| | Compound of formula (7a) 40% | Decylpoly-glucoside 7.5% | 52% | xanthan gum (0.2% + 0.3% propylene glycol) |
| Results for Example 3: | UV absorption between 300-400 nm | | | |

Example 4

| | Sparingly soluble micronized substance | Dispersing agent | water | Thickening agent |
|---|---|---|---|---|
| | Compound of formula (7b) 50% | Laurylether sulfate 3.5% | 56% | xanthan gum (0.2% + 0.3% propylene glycol) |
| Results for Example 4: | UV absorption between 300-400 nm | | | |

Example 5

| Sparingly soluble micronized substance | Dispersing agent | water | Thickening agent |
|---|---|---|---|
| Compound of formula (7a) 50% | Myrystylehter (EO3) sulfate 5% | 54.5% | xanthan gum (0.2% + 0.3% propylene glycol) |
| Results for Example 5: | UV absorption between 300-400 nm | | |

Example 6

UV-A/UV-B Every Day Protection Lotion O/W

| | INCI-Name | % w/w (as supplied) |
|---|---|---|
| Part A | Glyceryl Dilaurate | 2.00 |
| | Ethylhexyl Palmitate | 6.00 |
| | Cetyl Alcohol | 1.00 |
| | Glyceryl Stearate | 2.00 |
| | Laureth-23 | 1.00 |
| | Isopropyl Palmitate | 2.00 |
| | Tribehenin | 0.80 |
| | Beeswax | 1.50 |
| | Lanolin Oil | 1.00 |
| Part B | Water | qs to 100 |
| | Propylene Glycol | 4.00 |
| | Water (and) Titanium Dioxide (and) Alumina (and) Sodium Meta-phosphate (and) Phenoxyethanol (and) Sodium Methylparaben | 4.00 |
| Part C | Steareth-10 Allyl Ether/Acrylates Copolymer | 1.00 |
| Part D | Phenoxyethanol (and) Methylparaben (and) Ethylparaben (and) Butylparaben (and) Propylparaben (and) Isobutylparaben | 1.00 |
| | UV-absorber of formula (7c) or (7e) | 8.00 |
| Part E | Water (and) Sodium Hydroxide | qs |

Manufacturing Instruction:

Part A and part B are heated separately up to 80° C. Part A is poured into part B while stirring and homogenized with an Ultra Turrax by 11000 rpm for 30 sec. After cooling down to 60° C. part C is incorporated. At 40° C. part D is added slowly under continuous stirring. The pH is adjusted with part E between 6.50-7.00.

Example 7

UVA/UVB Sun Protection Lotion, O/W Type

| | INCI-Name | % w/w (as supplied) |
|---|---|---|
| Part A | Potassium Cetyl Phosphate | 2.00 |
| | Tricontanyl PVP | 1.00 |
| | Caprylic/Capric Triglyceride | 5.00 |
| | C12-15 Alkyl Benzoate | 5.00 |
| | Cetearyl Isononanoate | 5.00 |
| | Glyceryl Stearate | 3.00 |
| | Cetyl Alcohol | 1.00 |
| | Dimethicone | 0.10 |
| | Ethylhexyl Methoxycinnamate | 5.00 |
| Part B | Water | qs to 100 |
| | Glycerin | 3.00 |
| Part C | Steareth-10 Allyl Ether/Acrylates Copolymer | 0.50 |
| Part D | UV-absorber of formula (7c) or (7e) | 8.00 |
| Part E | Phenoxyethanol (and) Methylparaben (and) Ethylparaben (and) Butylparaben (and) Propylparaben (and) Isobutylparaben | 1.00 |
| Part F | Water (and) Sodium Hydroxide | qs to pH 7.00 |
| Part G | Fragrance | qs |

Manufacturing Instruction:

Part A and part B are heated separately up to 80° C. Part B is poured into part A under moderate stirring. The mixture is homogenized with an Ultra Turrax at 11000 rpm for 1 minute. After cooling down to 70° C. part C is added under stirring. After cooling further down to 50° C. part D is incorporated very slowly. At 40° C. part E is added. At room temperature the pH is adjusted with part F to 7.00 and part G is added.

Example 8

UVA/UVB Sun Protection Lotion, O/W Type

| | INCI-Name | % w/w (as supplied) |
|---|---|---|
| Part A | Potassium Cetyl Phosphate | 2.00 |
| | Tricontanyl PVP | 1.00 |
| | Caprylic/Capric Triglyceride | 5.00 |
| | C12-15 Alkyl Benzoate | 5.00 |
| | Cetearyl Isononanoate | 5.00 |
| | Glyceryl Stearate | 3.00 |
| | Cetyl Alcohol | 1.00 |
| | Dimethicone | 0.10 |
| | Ethylhexyl Methoxycinnamate | 5.00 |
| Part B | Water | qs to 100 |
| | Glycerin | 3.00 |
| Part C | Steareth-10 Allyl Ether/Acrylates Copolymer | 0.50 |
| Part D | UV-absorber of formula (7c) or (7e) | 20.00 |
| Part E | Phenoxyethanol (and) Methylparaben (and) Ethylparaben (and) Butylparaben (and) Propylparaben (and) Isobutylparaben | 1.00 |
| Part F | Water (and) Sodium Hydroxide | qs to pH 7.00 |
| Part G | Fragrance | qs |

Manufacturing Instruction:

Part A and part B are heated separately up to 80° C. Part B is poured into part A under moderate stirring. The mixture is homogenized with an Ultra Turrax at 11000 rpm for 1 minute. After cooling down to 70° C. add part C is added under stirring. After cooling further down to 50° C. part D is incorporated very slowly. At 40° C. part E is added. At room temperature the pH is adjusted with part. F to 7.00 and part G is added.

Example 9

W/O Sunscreen Lotion

| | INCI-Name | % w/w (as supplied) |
|---|---|---|
| Part A | PEG-7 Hydrogenated Castor Oil | 3.00 |
| | Polyglyceryl-3 Diisostearate | 4.00 |
| | Microcrystalline Wax | 1.00 |
| | Magnesium Stearate | 1.50 |

-continued

|  | INCI-Name | % w/w (as supplied) |
|---|---|---|
|  | Propylparaben | 0.10 |
|  | Mineral Oil | 15.00 |
|  | Octyldodecanol | 8.00 |
|  | Ethylhexyl Triazone | 1.00 |
|  | Ethylhexyl Methoxycinnamate | 2.00 |
| Part B | Water | qs to 100 |
|  | Water (and) Citric Acid | 0.05 |
|  | Methylparaben | 0.15 |
|  | Magnesium Sulfate | 0.50 |
| Part C | UV-absorber of formula (7c) or (7e) | 9.00 |
|  | Fragrance | qs |

Manufacturing Instruction:

Part A is heated to 80° C. whilst stirring. Part B is added into part A and homogenized with an Ultra Turrax at 11 000 rpm for one minute. After cooling down to 30° C. part C is incorporated.

Example 5

Skin Protection Lotion O/W

|  | INCI-Name | % w/w (as supplied) |
|---|---|---|
| Part A | Polyglyceryl-2 Dipolyhydroxystearate | 3.00 |
|  | Glyceryl Oleate | 3.00 |
|  | Cetearyl Isononanoate | 7.00 |
|  | Hexyl Laurate | 6.00 |
|  | Dicaprylyl Ether | 6.00 |
|  | Propylparaben | 0.10 |
|  | Hexyldecanol | 3.00 |
|  | Magnesium Stearate | 1.00 |
|  | Beeswax | 1.00 |
|  | Ethylhexyl Methoxycinnamate | 4.00 |
| Part B | Water | qs to 100 |
|  | Methylparaben | 0.15 |
|  | Magnesium Sulfate | 1.00 |
| Part C | UV-absorber of formula (7c) or (7e) | 6.00 |

Manufacturing Instruction:

Part A is heated separately to 80° C. under gentle stirring. Part B is added to part A and homogenized for one minute at 11000 rpm. After cooling down to 30° C. part C is added under continuous stirring.

Example 10

O/W Emulsion

|  | INCI-Name | % w/w (as supplied) |
|---|---|---|
| Part A | UV-absorber of formula (7c) or (7e) | 3 g |
|  | sesame oil | 10 g |
|  | glyceryl stearate | 4 g |
|  | stearic acid | 1 g |
|  | cetyl alcohol | 0.5 g |
|  | polysorbate 20 | 0.2 g |
| Part B | propylene glycol | 4 g |
|  | propylparaben | 0.05 g |
|  | methylparaben | 0.15 g |
|  | triethanolamine | 0.1 g |
|  | carbomer 934 | 0.1 g |
|  | water | ad 100 ml |

Preparation of the Emulsion

Phase (A):

Firstly, the UV absorber is dissolved in sesame oil. The other components of (A) are added thereto and combined.

Phase (B):

Propylparaben and methylparaben are dissolved in propylene glycol. 60 ml of water are then added, heating to 70° C. is carried out and then carbomer 934 is emulsified therein.

Emulsion:

(A) is slowly added to (B) with vigorous application of mechanical energy. The volume is adjusted to 100 ml by the addition of water.

Example 11

Daily Care Cream, Type O/W

|  | INCI name | % w/w (as used) |
|---|---|---|
| Part A | Glyceryl stearate (and) cetearyl alcohol (and) cetyl palmitate (and) cocoglycerides | 4.0 |
|  | Ceteareth-12 | 4.0 |
|  | Cetearyl alcohol | 2.0 |
|  | Dicaprylyl ether | 4.5 |
|  | Ethylhexyl stearate | 4.0 |
|  | Hexyl laurate | 3.5 |
|  | Ethylhexyl triazone | 1.0 |
|  | Benzylidene malonate polysiloxane | 2.0 |
|  | HDI/trimethylol hexyl-lactone crosspolymer (and) silica | 5.0 |
|  | Stearyl dimethicone | 1.0 |
|  | Dimethicone | 2.0 |
|  | Cetyl alcohol | 0.8 |
|  | UV-absorber of formula (7c) or (7e) | 2.0 |
| Part B | Water | q.s. to 100 |
|  | Water (and) scleroglucan (and) phenoxyethanol | 2.0 |
|  | Glycerol | 2.0 |
| Part C | Steareth-10 allyl ether/acrylate copolymer | 0.45 |
|  | Phenoxyethanol (and) methylparaben (and) ethylparaben (and) butylparaben (and) propylparaben (and) isobutylparaben | 0.7 |
| Part D | Aqua (and) tocopheryl acetate (and) caprylic/capric triglyceride (and) polysorbate 80 (and) lecithin | 4.0 |
| Part E | Water (and) sodium hydroxide | q.s. |
|  | Fragrance | q.s. |

Preparation Procedure:

Part A and part B are heated separately to 80° C. Part A is poured into part B, whilst stirring continuously. Afterwards the mixture is homogenized with an Ultra Turrax at 11 000 rpm for 20 sec. The mixture is cooled to 60° C. and part C is added. At a temperature below 30° C., part D is added and the pH value is adjusted with sodium hydroxide to between 6.5 and 7.0. Finally, fragrance is added.

Example 12

Sun-Protection Cream, Type O/W

|  | INCI name | % w/w (as used) |
|---|---|---|
| Part A | Polyglyceryl-3 methylglucose distearate | 2.0 |
|  | Decyl oleate | 5.7 |
|  | Isopropyl palmitate | 5.8 |
|  | Caprylic/capric triglyceride | 6.5 |
|  | UV-absorber of formula (7c) or (7e) | 2.0 |
|  | Ethylhexyl methoxycinnamate | 5.0 |
|  | Cetyl alcohol | 0.7 |
| Part B | Glycerol | 3.0 |
|  | Carbomer | 0.3 |
|  | Water | q.s. to 100 |

-continued

| | INCI name | % w/w (as used) |
|---|---|---|
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure

Part A and part B are heated separately to 75° C. Part A is poured into part B whilst stirring. The mixture is homogenised with an Ultra Turrax at 11 000 rpm for 15 sec. The mixture is cooled to 60° C. and part C and part D are incorporated. The mixture is homogenised again for a short time (5 sec./11 000 rpm) and further cooled, with moderate stirring. At room temperature, the pH is adjusted with sodium hydroxide solution to between 5.5 and 6.0. Finally, fragrance is added.

Example 13

Daily Care UV-Protection Lotion

| | INCI name | % w/w (as used) |
|---|---|---|
| Part A | Oleth-3 phosphate | 0.6 |
| | Steareth-21 | 2.5 |
| | Steareth-2 | 1.0 |
| | Cetyl alcohol | 0.8 |
| | Stearyl alcohol | 1.5 |
| | Tribehenin | 0.8 |
| | Isohexadecane | 8.0 |
| | UV-absorber of formula (7c) or (7e) | 5.0 |
| Part B | Water | q.s. to 100 |
| | Glycerol | 2.0 |
| | Methylene bis-benzotriazolyl tetramethylbutylphenol (and) aqua (and) decyl glucoside (and) propylene glycol (and) xanthan gum | 3.0 |
| | Disodium EDTA | 0.1 |
| Part C | Water | 20.0 |
| | Diazolidinyl urea (and) iodopropynyl butytcarbamate | 0.15 |
| | Propylene glycol | 4.0 |
| Part D | Sodium acrylate copolymer (and) liquid paraffin (and) PPG-1 trideceth-6 | 1.5 |
| | Cyclopentasiloxane | 4.5 |
| | PEG-12 dimethicone | 2.0 |
| | Tocopheryl acetate | 0.45 |
| | Water (and) citric acid | q.s. |
| Part E | Fragrance | q.s. |

Preparation Procedure

Heat part A and part B separately to 75° C. Pour part A into part B, whilst stirring continuously. Immediately after emulsification, incorporate in the mixture SF 1202 and SF 1288 from part D. Afterwards homogenise with an Ultra Turrax at 11 000 rpm for 30 sec. Allow to cool to 65° C. and incorporate SALCARE® SC91. At a temperature below 50° C., add part C. At 35° C. or below, incorporate vitamin E acetate and subsequently adjust the pH with citric acid. At room temperature, add part E.

Example 14

Sun-Protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | UV-absorber of formula (7c) or (7e) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure:

Part A and part B are heated separately to 75° C. Part A is poured into part B whilst stirring. The mixture is homogenised with an Ultra Turrax at 11 000 rpm for 15 sec. The mixture is cooled to 60° C., and part C and part D are incorporated. The mixture is homogenised again for a short time (5 sec./11 000 rpm). After further cooling, with moderate stirring, the pH is adjusted with sodium hydroxide at room temperature. A solution between pH 5.50 and 6.00 is obtained. Finally, fragrance is added.

Example 15

Sun-Protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | Mixture of the compound of UV-absorber of formula (7c) or (7e) (50%) and Uvinul A Plus CAS Reg. No. 302776-68-7 (50%) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure:

Part A and part B are heated separately to 75° C. Part A is poured into part B whilst stirring. The mixture is homogenised with an Ultra Turrax at 11 000 rpm for 15 sec. After cooling 60° C., part C and part D are incorporated. The mixture is homogenised again for a short time (5 sec./11 000 rpm). After further cooling, with moderate stirring, the pH is adjusted at room temperature with sodium hydroxide solution to between 5.50 and 6.00. Finally, fragrance is added.

Example 16

Sun-Protection Cream, Type O/W

| | INCI name | % w/w (as used) |
|---|---|---|
| Part A | Polyglyceryl-3 methylglucose distearate | 2.0 |
| | Decyl oleate | 5.7 |
| | Isopropyl palmitate | 5.8 |
| | Caprylic/capric triglyceride | 6.5 |
| | Mixture of the compound of UV-absorber of formula (7c) or (7e) (50%) and Uvinul A Plus CAS Reg. No. 302776-68-7 (50%) | 2.0 |
| | Ethylhexyl methoxycinnamate | 5.0 |
| | Cetyl alcohol | 0.7 |
| Part B | Glycerol | 3.0 |
| | Carbomer | 0.3 |
| | Water | q.s. to 100 |
| Part C | Phenoxyethanol (and) methylparaben (and) ethylparaben (and) butylparaben (and) propylparaben (and) isobutylparaben | 0.5 |
| Part D | Methylene bis-benzotriazolyl tetramethylbutylphenol (and) aqua (and) decyl glucoside (and) propylene glycol (and) xanthan gum | 8.0 |
| | Water | 20.0 |
| Part E | Water (and) sodium hydroxide | q.s. |
| | Fragrance | q.s. |

Preparation Procedure

Part A and part B are heated separately to 75° C. Part A is poured into part B whilst stirring. The mixture is homogenised with an Ultra Turrax at 11 000 rpm for 15 sec. After cooling to 60° C., part C and part D are incorporated. The mixture is homogenised again for a short time (5 sec./11 000 rpm). After further cooling, with moderate stirring, the pH is adjusted at room temperature with sodium hydroxide. A solution between pH 5.50 and 6.00 is obtained. Finally, fragrance is added.

The invention claimed is:

1. A method for protecting the skin and hair of humans and animals from the harmful effects of UV radiation wherein the method comprises applying to the hair and skin an effective amount of at least one compound of formula (7)

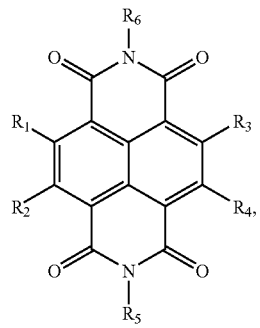

(7)

wherein $R_1$, $R_2$, $R_3$, $R_4$, $R_5$, and $R_6$ independently from each other are hydrogen; or C1-C37 alkyl.

2. A method according to claim 1 wherein the compound of formula (7) is selected from the group consisting of

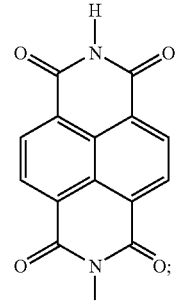

(7a)

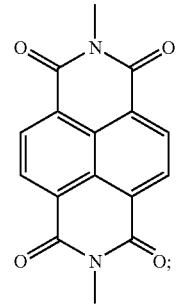

(7b)

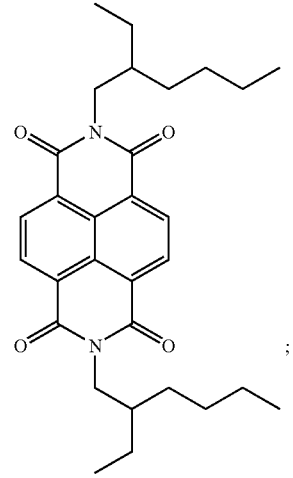

(7c)

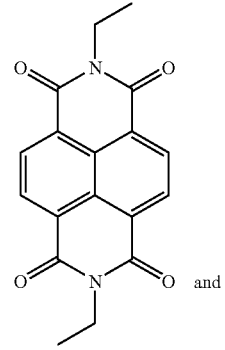

(7d)

and (7e)
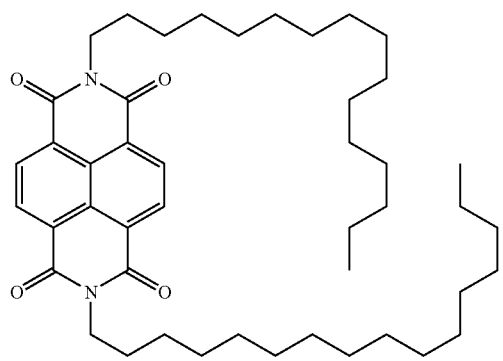
3. A sunscreen preparation comprising 0.05-40% weight, based on the total weight of the preparation, of at least one compound of formula (7)
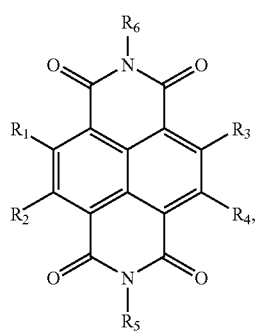
(7)
wherein
$R_1$, $R_2$, $R_3$, $R_4$, $R_5$, and $R_6$ independently from each other are hydrogen; or C1-C3 alkyl.
4. A sunscreen preparation according to claim 3 wherein the compound of formula (7) is selected from the group consisting of
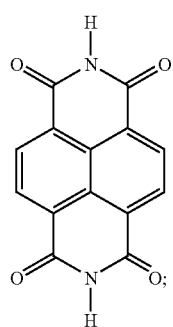
(7a)
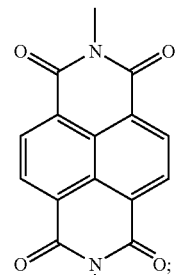
(7b)
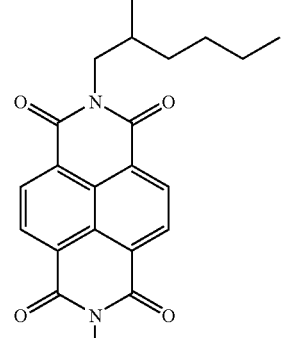
(7c)
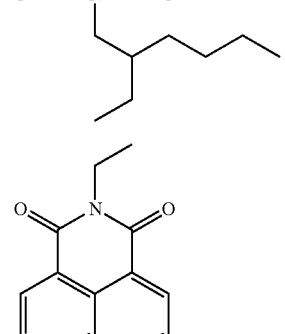
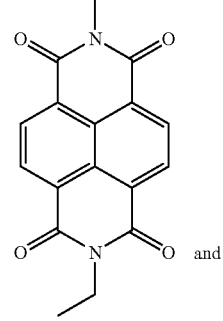
(7d)
and
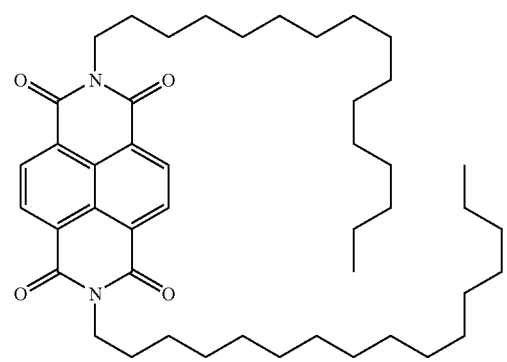
(7e)
* * * * *